(12) United States Patent
Salahieh et al.

(10) Patent No.: US 11,052,226 B2
(45) Date of Patent: Jul. 6, 2021

(54) STEERABLE MEDICAL DEVICES, SYSTEMS, AND METHODS OF USE

(71) Applicant: Kalila Medical, Inc., Campbell, CA (US)

(72) Inventors: Amr Salahieh, Saratoga, CA (US); Jonah Lepak, Santa Cruz, CA (US); Emma Lepak, Santa Cruz, CA (US); Tom Saul, Moss Beach, CA (US); Jean-Pierre Dueri, Los Gatos, CA (US); Joseph Creagan Trautman, Sunnyvale, CA (US); Christopher T. Cheng, Los Altos, CA (US); Richard Joseph Renati, Los Gatos, CA (US); Colin Mixter, Santa Clara, CA (US); Marc Bitoun, Santa Cruz, CA (US)

(73) Assignee: Kalila Medical, Inc., Campbell, CA (US)

( * ) Notice: Subject to any disclaimer, the term of this patent is extended or adjusted under 35 U.S.C. 154(b) by 1179 days.

(21) Appl. No.: 15/138,050

(22) Filed: Apr. 25, 2016

(65) Prior Publication Data
US 2017/0080186 A1   Mar. 23, 2017

Related U.S. Application Data

(60) Provisional application No. 62/152,741, filed on Apr. 24, 2015.

(51) Int. Cl.
*A61M 25/01* (2006.01)
*A61B 1/00* (2006.01)
(Continued)

(52) U.S. Cl.
CPC ....... *A61M 25/0147* (2013.01); *A61B 1/0052* (2013.01); *A61B 1/0055* (2013.01);
(Continued)

(58) Field of Classification Search
CPC ............ A61M 25/005; A61M 25/0141; A61M 25/0138; A61M 25/0147;
(Continued)

(56) References Cited

U.S. PATENT DOCUMENTS

| | | | |
|---|---|---|---|
| 3,552,384 A | 1/1971 | Pierie et al. | |
| 4,031,713 A | 6/1977 | Driver | |

(Continued)

FOREIGN PATENT DOCUMENTS

| | | |
|---|---|---|
| DE | 4104092 A1 | 8/1991 |
| EP | 0521595 A2 | 1/1993 |

(Continued)

OTHER PUBLICATIONS

Lepak et al.; U.S. Appl. No. 15/663,523 entitled "Energy delivery devices," filed Jul. 28, 2017.
(Continued)

*Primary Examiner* — Nathan R Price
*Assistant Examiner* — John A Doubrava
(74) *Attorney, Agent, or Firm* — Inskeep IP Group, Inc.

(57) ABSTRACT

Steerable medical devices and methods of use. In some embodiments, the steerable medical devices can be steered bi-directionally. In some embodiments the steerable medical devices include a first flexible tubular member and a second flexible tubular member secured together at a location distal to a steerable portion of the steerable medical device.

9 Claims, 53 Drawing Sheets

(51) Int. Cl.
*A61B 1/005* (2006.01)
*A61M 25/00* (2006.01)

(52) U.S. Cl.
CPC ..... *A61B 1/00147* (2013.01); *A61M 25/0053* (2013.01); *A61M 25/0136* (2013.01); *A61M 25/0138* (2013.01); *A61M 25/005* (2013.01); *A61M 25/0012* (2013.01); *A61M 25/0141* (2013.01); *A61M 2025/0004* (2013.01)

(58) Field of Classification Search
CPC ...... A61M 2025/0004; A61M 25/0053; A61M 25/0144; A61M 25/012; A61M 37/00; A61B 1/0055; A61B 1/0056
See application file for complete search history.

(56) References Cited

U.S. PATENT DOCUMENTS

| | | |
|---|---|---|
| 4,353,358 A | 10/1982 | Emerson |
| 4,448,188 A | 5/1984 | Loeb |
| 4,547,193 A | 10/1985 | Rydell |
| 4,580,551 A | 4/1986 | Siegmund et al. |
| 4,634,432 A | 1/1987 | Kocak |
| 4,692,139 A | 9/1987 | Stiles |
| 4,726,382 A | 2/1988 | Boehmer et al. |
| 4,890,623 A | 1/1990 | Cook et al. |
| 4,911,148 A | 3/1990 | Sosnowski et al. |
| 5,005,587 A | 4/1991 | Scott |
| 5,010,895 A | 4/1991 | Maurer et al. |
| 5,041,089 A | 8/1991 | Mueller et al. |
| 5,052,404 A | 10/1991 | Hodgson |
| 5,069,674 A | 12/1991 | Fearnot et al. |
| 5,180,376 A | 1/1993 | Fischell |
| 5,209,741 A | 5/1993 | Spaeth |
| 5,228,441 A | 7/1993 | Lundquist |
| 5,228,442 A | 7/1993 | Imran |
| 5,235,964 A | 8/1993 | Abenaim |
| 5,284,128 A | 2/1994 | Hart |
| 5,299,562 A | 4/1994 | Heckele et al. |
| 5,309,910 A | 5/1994 | Edwards et al. |
| 5,311,866 A | 5/1994 | Kagan et al. |
| 5,315,996 A | 5/1994 | Lundquist |
| 5,322,064 A | 6/1994 | Lundquist |
| 5,325,845 A | 7/1994 | Adair |
| 5,329,923 A | 7/1994 | Lundquist |
| 5,334,145 A | 8/1994 | Lundquist et al. |
| 5,343,860 A | 9/1994 | Metzger et al. |
| 5,366,490 A | 11/1994 | Edwards et al. |
| 5,370,675 A | 12/1994 | Edwards et al. |
| 5,372,587 A | 12/1994 | Hammerslag et al. |
| 5,381,782 A | 1/1995 | DeLaRama et al. |
| 5,385,544 A | 1/1995 | Edwards et al. |
| 5,391,200 A | 2/1995 | KenKnight et al. |
| 5,395,329 A | 3/1995 | Fleischhacker et al. |
| 5,409,453 A | 4/1995 | Lundquist et al. |
| 5,421,819 A | 6/1995 | Edwards et al. |
| 5,435,805 A | 7/1995 | Edwards et al. |
| 5,443,470 A | 8/1995 | Stern et al. |
| 5,454,787 A | 10/1995 | Lundquist |
| 5,456,662 A | 10/1995 | Edwards et al. |
| 5,470,308 A | 11/1995 | Edwards et al. |
| 5,470,309 A | 11/1995 | Edwards et al. |
| 5,480,382 A | 1/1996 | Hammerslag et al. |
| 5,505,730 A | 4/1996 | Edwards |
| 5,515,848 A | 5/1996 | Corbett, III et al. |
| 5,524,338 A | 6/1996 | Martyniuk et al. |
| 5,540,679 A | 7/1996 | Fram et al. |
| 5,558,672 A | 9/1996 | Edwards et al. |
| 5,562,720 A | 10/1996 | Stern et al. |
| 5,569,218 A | 10/1996 | Berg |
| 5,569,241 A | 10/1996 | Edwards |
| 5,571,088 A | 11/1996 | Lennox et al. |
| 5,573,520 A | 11/1996 | Schwartz et al. |
| 5,575,772 A | 11/1996 | Lennox |
| 5,575,788 A | 11/1996 | Baker et al. |
| 5,609,606 A | 3/1997 | O'Boyle |
| 5,630,837 A | 5/1997 | Crowley |
| 5,681,308 A | 10/1997 | Edwards et al. |
| 5,715,825 A | 2/1998 | Crowley |
| 5,718,701 A | 2/1998 | Shai et al. |
| 5,735,846 A | 4/1998 | Panescu et al. |
| 5,741,429 A | 4/1998 | Donadio, III et al. |
| 5,769,846 A | 6/1998 | Edwards et al. |
| 5,772,641 A | 6/1998 | Wilson |
| 5,779,698 A | 7/1998 | Clayman et al. |
| 5,836,874 A | 11/1998 | Swanson et al. |
| 5,846,196 A | 12/1998 | Siekmeyer et al. |
| 5,846,238 A | 12/1998 | Jackson et al. |
| 5,846,239 A | 12/1998 | Swanson et al. |
| 5,851,212 A | 12/1998 | Zirps et al. |
| 5,853,411 A | 12/1998 | Whayne et al. |
| 5,860,974 A | 1/1999 | Abele |
| 5,871,483 A | 2/1999 | Jackson et al. |
| 5,879,348 A | 3/1999 | Owens et al. |
| 5,888,577 A | 3/1999 | Griffin, III et al. |
| 5,904,651 A | 5/1999 | Swanson et al. |
| 5,911,715 A | 6/1999 | Berg et al. |
| 5,938,660 A | 8/1999 | Swartz et al. |
| 5,961,513 A | 10/1999 | Swanson et al. |
| 5,991,650 A | 11/1999 | Swanson et al. |
| 6,004,269 A | 12/1999 | Crowley et al. |
| 6,012,457 A | 1/2000 | Lesh |
| 6,024,740 A | 2/2000 | Lesh et al. |
| 6,048,339 A | 4/2000 | Zirps et al. |
| 6,052,607 A | 4/2000 | Edwards et al. |
| 6,053,922 A | 4/2000 | Krause et al. |
| 6,093,177 A | 7/2000 | Javier, Jr. et al. |
| 6,123,718 A | 9/2000 | Tu et al. |
| 6,142,993 A | 11/2000 | Whayne et al. |
| 6,163,726 A | 12/2000 | Wolf |
| 6,164,283 A | 12/2000 | Lesh |
| 6,197,015 B1 | 3/2001 | Wilson |
| 6,206,912 B1 | 3/2001 | Goldsteen et al. |
| 6,246,914 B1 | 6/2001 | de la Rama et al. |
| 6,292,689 B1 | 9/2001 | Wallace et al. |
| 6,402,746 B1 | 6/2002 | Whayne et al. |
| 6,460,545 B2 | 10/2002 | Kordis |
| 6,500,174 B1 | 12/2002 | Maguire et al. |
| 6,511,471 B2 | 1/2003 | Rosenman et al. |
| 6,514,249 B1 | 2/2003 | Maguire et al. |
| 6,551,271 B2 | 4/2003 | Nguyen |
| 6,558,378 B2 | 5/2003 | Sherman et al. |
| 6,572,612 B2 | 6/2003 | Stewart et al. |
| 6,585,718 B2 | 7/2003 | Hayzelden et al. |
| 6,595,989 B1 | 7/2003 | Schaer |
| 6,602,262 B2 | 8/2003 | Griego et al. |
| 6,652,515 B1 | 11/2003 | Maguire et al. |
| 6,660,002 B1 | 12/2003 | Edwards et al. |
| 6,685,679 B2 | 2/2004 | Merdan |
| 6,736,811 B2 | 5/2004 | Panescu et al. |
| 6,743,226 B2 | 6/2004 | Cosman et al. |
| 6,749,560 B1 | 6/2004 | Konstorum et al. |
| 6,771,996 B2 | 8/2004 | Bowe et al. |
| 6,780,183 B2 | 8/2004 | Jimenez, Jr. et al. |
| 6,808,524 B2 | 10/2004 | Lopath et al. |
| 6,814,730 B2 | 11/2004 | Li |
| 6,869,431 B2 | 3/2005 | Maguire et al. |
| 6,872,183 B2 | 3/2005 | Sampson et al. |
| 6,872,206 B2 | 3/2005 | Edwards et al. |
| 6,887,235 B2 | 5/2005 | O'Connor et al. |
| 6,911,027 B1 | 6/2005 | Edwards et al. |
| 6,945,956 B2 | 9/2005 | Waldhauser et al. |
| 6,978,174 B2 | 12/2005 | Gelfand et al. |
| 6,979,312 B2 | 12/2005 | Shimada |
| 7,001,369 B2 | 2/2006 | Griffin et al. |
| 7,048,733 B2 | 5/2006 | Hartley et al. |
| 7,101,362 B2 | 9/2006 | Vanney |
| 7,105,003 B2 | 9/2006 | Hiltebrandt |
| 7,115,122 B1 | 10/2006 | Swanson et al. |
| 7,137,395 B2 | 11/2006 | Fried et al. |
| 7,150,745 B2 | 12/2006 | Stern et al. |
| 7,162,303 B2 | 1/2007 | Levin et al. |
| 7,226,448 B2 | 6/2007 | Bertolero et al. |
| 7,232,437 B2 | 6/2007 | Berman et al. |

(56) References Cited

U.S. PATENT DOCUMENTS

| | | |
|---|---|---|
| 7,238,179 B2 | 7/2007 | Brucker et al. |
| 7,238,180 B2 | 7/2007 | Mester et al. |
| 7,267,674 B2 | 9/2007 | Brucker et al. |
| 7,276,062 B2 | 10/2007 | McDaniel et al. |
| 7,286,866 B2 | 10/2007 | Okerlund et al. |
| 7,291,146 B2 | 11/2007 | Steinke et al. |
| 7,310,150 B2 | 12/2007 | Guillermo et al. |
| 7,346,381 B2 | 3/2008 | Okerlund et al. |
| 7,365,859 B2 | 4/2008 | Yun et al. |
| 7,366,376 B2 | 4/2008 | Shishkov et al. |
| 7,371,231 B2 | 5/2008 | Rioux et al. |
| 7,382,949 B2 | 6/2008 | Bouma et al. |
| 7,396,355 B2 | 7/2008 | Goldman et al. |
| 7,402,151 B2 | 7/2008 | Rosenman et al. |
| 7,406,970 B2 | 8/2008 | Zikorus et al. |
| 7,413,568 B2 | 8/2008 | Swanson et al. |
| 7,418,169 B2 | 8/2008 | Tearney et al. |
| 7,429,260 B2 | 9/2008 | Underwood et al. |
| 7,429,261 B2 | 9/2008 | Kunis et al. |
| 7,445,618 B2 | 11/2008 | Eggers et al. |
| 7,447,408 B2 | 11/2008 | Bouma et al. |
| 7,452,358 B2 | 11/2008 | Stern et al. |
| 7,468,062 B2 | 12/2008 | Oral et al. |
| 7,469,700 B2 | 12/2008 | Baran |
| 7,472,705 B2 | 1/2009 | Baran |
| 7,473,251 B2 | 1/2009 | Knowlton et al. |
| 7,481,808 B2 | 1/2009 | Koyfman et al. |
| 7,481,809 B2 | 1/2009 | Stern et al. |
| 7,489,969 B2 | 2/2009 | Knudson et al. |
| 7,507,236 B2 | 3/2009 | Eggers et al. |
| 7,510,555 B2 | 3/2009 | Kanzius |
| 7,519,096 B2 | 4/2009 | Bouma et al. |
| 7,529,393 B2 | 5/2009 | Peszynski et al. |
| 7,538,859 B2 | 5/2009 | Tearney et al. |
| 7,617,005 B2 | 11/2009 | Demarais et al. |
| 7,620,451 B2 | 11/2009 | Demarais et al. |
| 7,653,438 B2 | 1/2010 | Deem et al. |
| 7,669,309 B2 | 3/2010 | Johnson et al. |
| 7,691,095 B2 | 4/2010 | Bednarek et al. |
| 7,711,148 B2 | 5/2010 | Slabaugh et al. |
| 7,756,583 B2 | 7/2010 | Demarais et al. |
| 7,819,857 B2 | 10/2010 | Ponzi et al. |
| 7,853,333 B2 | 12/2010 | Demarais |
| 8,295,902 B2 | 10/2012 | Salahieh et al. |
| 8,323,239 B2 | 12/2012 | Bednarek et al. |
| 8,323,241 B2 | 12/2012 | Salahieh et al. |
| 8,435,229 B2 | 5/2013 | Frassica et al. |
| 8,500,733 B2 | 8/2013 | Watson |
| 8,708,953 B2 | 4/2014 | Salahieh et al. |
| 8,805,466 B2 | 8/2014 | Salahieh et al. |
| 8,840,601 B2 | 9/2014 | Salahieh et al. |
| 8,858,495 B2 | 10/2014 | Tegg et al. |
| 8,920,369 B2 | 12/2014 | Salahieh et al. |
| 8,992,470 B2 | 3/2015 | Barenboym et al. |
| 9,039,676 B2 | 5/2015 | Klima |
| 9,132,258 B2 | 9/2015 | Bednarek et al. |
| 9,333,031 B2 | 5/2016 | Salahieh et al. |
| 2001/0034514 A1 | 10/2001 | Parker |
| 2002/0002384 A1 | 1/2002 | Gilson et al. |
| 2002/0082585 A1 | 6/2002 | Carroll et al. |
| 2002/0095147 A1 | 7/2002 | Shadduck |
| 2002/0156460 A1 | 10/2002 | Ye et al. |
| 2003/0236443 A1 | 12/2003 | Cespedes et al. |
| 2004/0102719 A1 | 5/2004 | Keith et al. |
| 2005/0131343 A1 | 6/2005 | Abrams et al. |
| 2005/0159728 A1 | 7/2005 | Armour et al. |
| 2005/0245892 A1 | 11/2005 | Elkins et al. |
| 2006/0041277 A1 | 2/2006 | Deem et al. |
| 2006/0100618 A1 | 5/2006 | Chan et al. |
| 2006/0100687 A1 | 5/2006 | Fahey et al. |
| 2006/0206150 A1 | 9/2006 | Demarais et al. |
| 2006/0212076 A1 | 9/2006 | Demarais et al. |
| 2006/0212078 A1 | 9/2006 | Demarais et al. |
| 2006/0241564 A1 | 10/2006 | Corcoran et al. |
| 2006/0247701 A1 | 11/2006 | Zacouto |
| 2006/0265014 A1 | 11/2006 | Demarais et al. |
| 2006/0265015 A1 | 11/2006 | Demarais et al. |
| 2006/0271111 A1 | 11/2006 | Demarais et al. |
| 2006/0276852 A1 | 12/2006 | Demarais et al. |
| 2007/0078507 A1 | 4/2007 | Zacouto |
| 2007/0112422 A1 | 5/2007 | Dehdashtian |
| 2007/0129760 A1 | 6/2007 | Demarais et al. |
| 2007/0135875 A1 | 6/2007 | Demarais et al. |
| 2007/0225634 A1 | 9/2007 | Ferren et al. |
| 2007/0244501 A1 | 10/2007 | Horn et al. |
| 2007/0250036 A1 | 10/2007 | Kornkven et al. |
| 2008/0021405 A1 | 1/2008 | Jacobsen et al. |
| 2008/0065011 A1 | 3/2008 | Marchand et al. |
| 2008/0086854 A1 | 4/2008 | Boyd et al. |
| 2008/0140053 A1 | 6/2008 | Partlett |
| 2008/0183128 A1 | 7/2008 | Morriss et al. |
| 2008/0188800 A1* | 8/2008 | Bencini .............. A61M 25/0141 604/95.01 |
| 2008/0188912 A1 | 8/2008 | Stone et al. |
| 2008/0188928 A1 | 8/2008 | Salahieh et al. |
| 2008/0275445 A1 | 11/2008 | Kelly et al. |
| 2008/0281312 A1 | 11/2008 | Werneth et al. |
| 2008/0281322 A1 | 11/2008 | Sherman et al. |
| 2008/0296152 A1 | 12/2008 | Voss |
| 2009/0024195 A1 | 1/2009 | Rezai et al. |
| 2009/0156998 A1 | 6/2009 | Arana et al. |
| 2009/0227885 A1 | 9/2009 | Lowery et al. |
| 2009/0240249 A1 | 9/2009 | Chan et al. |
| 2009/0254142 A1 | 10/2009 | Edwards et al. |
| 2009/0287187 A1 | 11/2009 | Legaspi et al. |
| 2009/0312696 A1 | 12/2009 | Copa et al. |
| 2009/0312698 A1 | 12/2009 | Farrell et al. |
| 2009/0312754 A1 | 12/2009 | Lenihan et al. |
| 2010/0004633 A1 | 1/2010 | Rothe et al. |
| 2010/0268234 A1 | 10/2010 | Aho et al. |
| 2010/0324506 A1 | 12/2010 | Pellegrino et al. |
| 2012/0116438 A1 | 5/2012 | Salahieh et al. |
| 2012/0123327 A1* | 5/2012 | Miller ............... A61M 25/0012 604/95.04 |
| 2013/0116705 A1* | 5/2013 | Salahieh ............ A61B 1/00135 606/130 |
| 2013/0138082 A1 | 5/2013 | Salahieh et al. |
| 2014/0058197 A1 | 2/2014 | Salahieh et al. |
| 2014/0107623 A1* | 4/2014 | Salahieh ............ A61M 25/0105 604/528 |
| 2014/0135576 A1 | 5/2014 | Hebert |
| 2014/0135736 A1 | 5/2014 | Herbert |
| 2014/0236120 A1 | 8/2014 | Tsai et al. |
| 2014/0357956 A1 | 12/2014 | Salahieh et al. |
| 2015/0073341 A1 | 3/2015 | Salahieh et al. |
| 2015/0094656 A1 | 4/2015 | Salahieh et al. |
| 2016/0051321 A1 | 2/2016 | Salahieh et al. |
| 2017/0296266 A1 | 10/2017 | Salahieh et al. |

FOREIGN PATENT DOCUMENTS

| | | |
|---|---|---|
| EP | 0637943 B1 | 4/1998 |
| EP | 0723467 B1 | 4/2002 |
| EP | 0693955 B1 | 1/2003 |
| EP | 1382366 A1 | 1/2004 |
| EP | 1927375 A2 | 6/2008 |
| EP | 2135634 A1 | 12/2009 |
| GB | 2331933 A | 6/1999 |
| JP | S49-97484 U | 8/1974 |
| JP | H05-76554 A | 3/1993 |
| JP | H06-86822 A | 3/1994 |
| JP | H08-506259 | 7/1996 |
| JP | H09-28808 A | 2/1997 |
| JP | H09-504445 A | 5/1997 |
| JP | 2001-9042 A | 1/2001 |
| JP | 2006158788 | 6/2006 |
| JP | 2007530163 | 11/2007 |
| WO | WO 99/00060 A1 | 1/1999 |
| WO | WO 00/66014 A1 | 11/2000 |
| WO | WO02/083228 A2 | 10/2002 |
| WO | WO2004/105849 A1 | 12/2004 |
| WO | WO 2006/012668 A1 | 2/2006 |
| WO | WO 2006/122155 A1 | 11/2006 |

(56) References Cited

FOREIGN PATENT DOCUMENTS

| WO | WO2007/149841 A2 | 12/2007 |
| WO | WO 2009/067695 A1 | 5/2009 |
| WO | WO2009/125575 A1 | 10/2009 |
| WO | WO 2009/132137 A1 | 10/2009 |
| WO | WO2009/137712 A1 | 11/2009 |
| WO | WO 2010/151698 A2 | 12/2010 |
| WO | WO11/46002 | 4/2011 |
| WO | WO 2013/049601 A2 | 4/2013 |

OTHER PUBLICATIONS

Salahieh et al.; U.S. Appl. No. 15/339,724 entitled "Ablation catheters," filed Oct. 31, 2016.

Salahieh et al.; U.S. Appl. No. 15/339,745 entitled "Ablation catheters," filed Oct. 31, 2016.

Salahieh et al.; U.S. Appl. No. 15/375,027 entitled "Steerable medical devices, systems, and methods of use," filed Dec. 9, 2017.

Salahieh et al.; U.S. Appl. No. 15/167,509 entitled "Intravascular tissue disruption," filed May 27, 2016.

Claude et al.; U.S. Appl. No. 15/194,444 entitled "Tissue mapping and visualization systems," filed Jun. 27, 2016.

Salahieh et al.; U.S. Appl. No. 15/452,413 entitled "Steerable delivery sheaths," filed Mar. 7, 2017.

Salahieh et al.; U.S. Appl. No. 15/375,027 entitled "Steerable medical devices, systems, and methods of use," filed Dec. 9, 2016.

DRAFTS, Bill; Acoustic wave technology sensors; Sensors Weekly (Questex Media Group); 10 pgs.; Oct. 1, 2000 (http://www.sensorsmag.com/sensors/acoustic-ultrasound/acoustic-wave-technology-sensors-936).

Salahieh et al.; U.S. Appl. No. 13/830,624 entitled "Local Sympathectomy for PVD," filed Mar. 14, 2013.

Salahieh et al.; U.S. Appl. No. 61/622,495 entitled "Energy Delivery Device with Rapid Exchange Features," filed Apr. 10, 2012.

Salahieh et al.; U.S. Appl. No. 61/624,206 entitled "Energy delivery device and methods of use," filed Apr. 13, 2012.

Salahieh et al.; U.S. Appl. No. 15/082,923 entitled "Steerable medical devices, systems, and methods of use," filed Mar. 28, 2016.

Salahieh et al.; U.S. Appl. No. 15/092,442 entitled "Intravascular tissue disruption," filed Apr. 6, 2016.

Lepak et al.; U.S. Appl. No. 15/769,354 entitled "Steering assemblies for medical devices, and methods of use," filed Apr. 19, 2018.

* cited by examiner

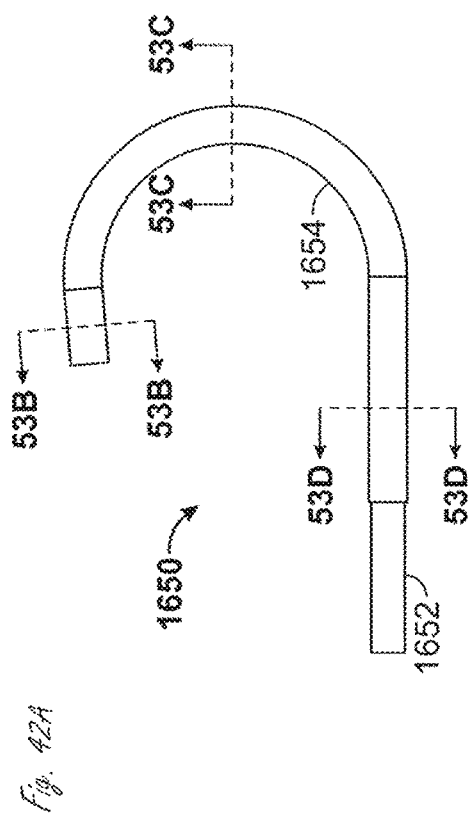
Fig. 42A
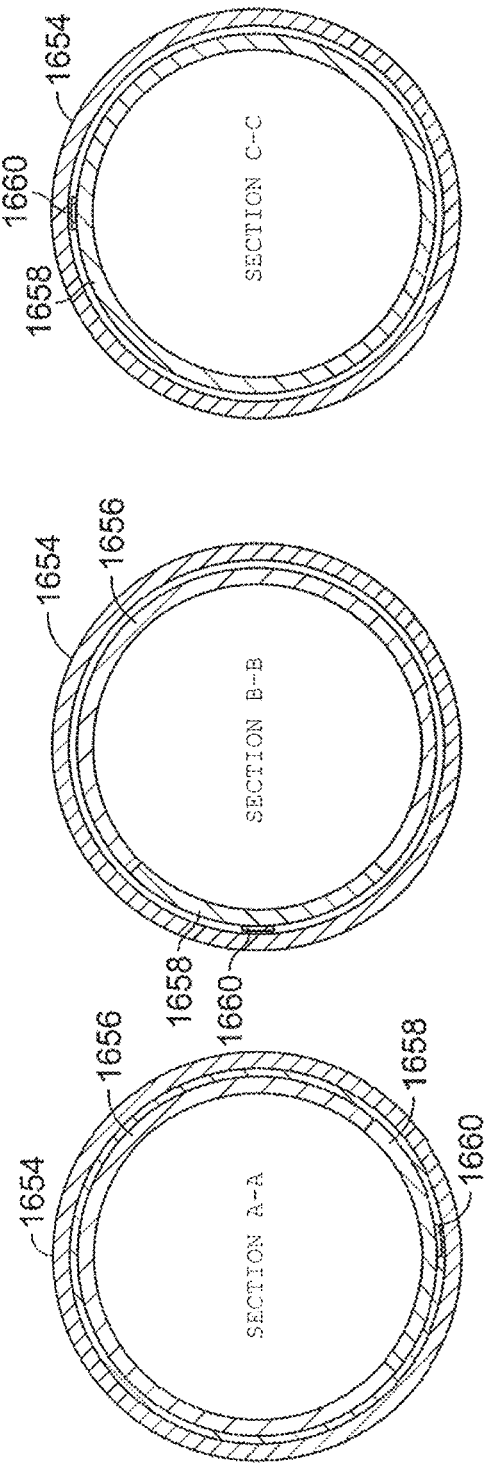
Fig. 42D
Fig. 42C
Fig. 42B

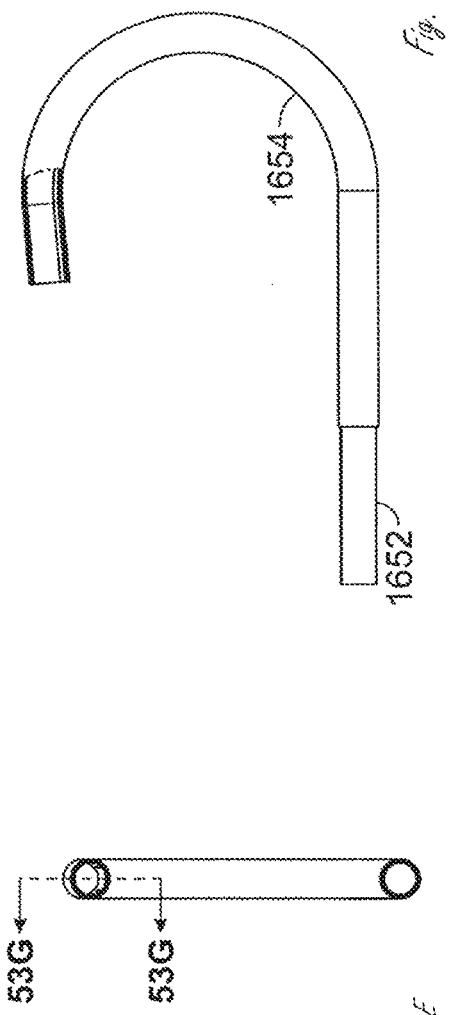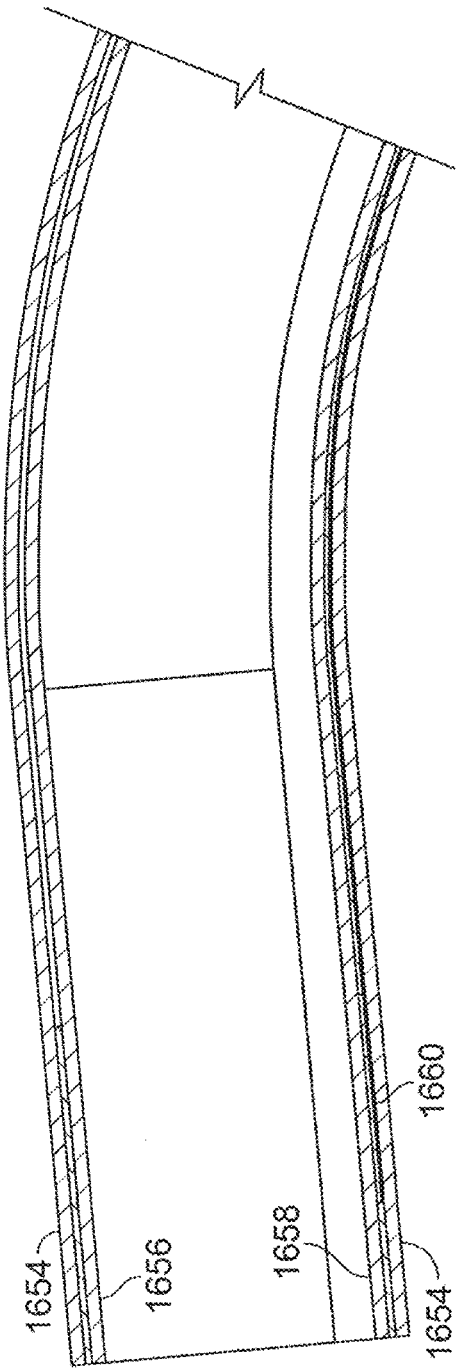

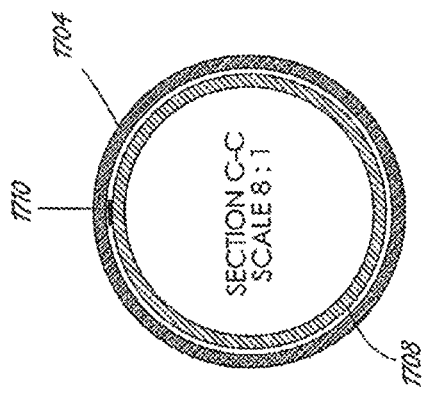
Fig. 43A
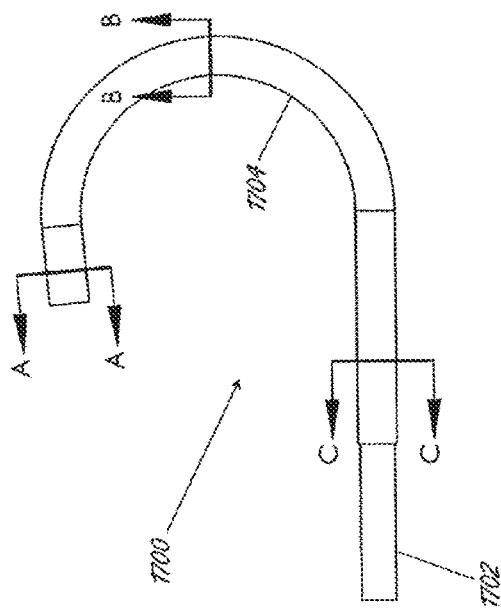
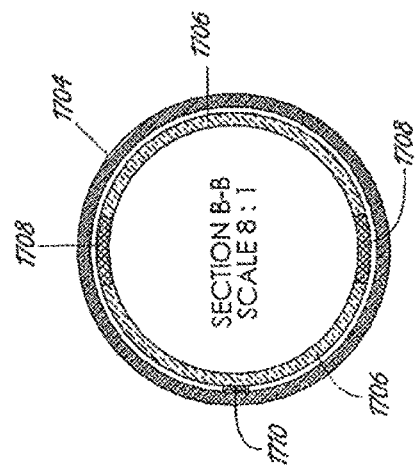
Fig. 43C
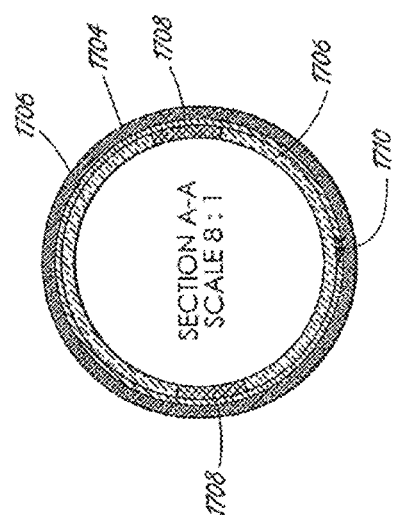
Fig. 43B

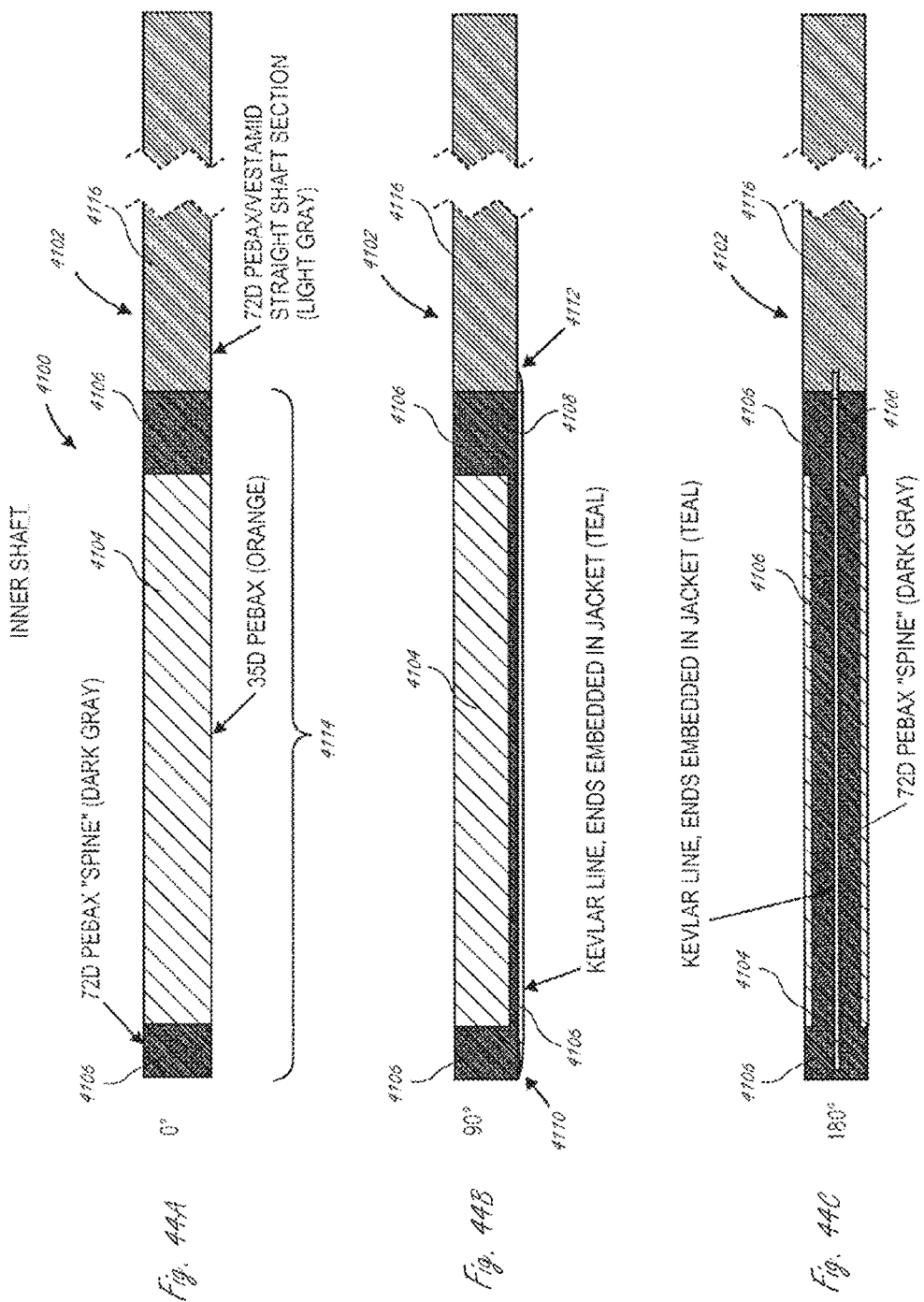

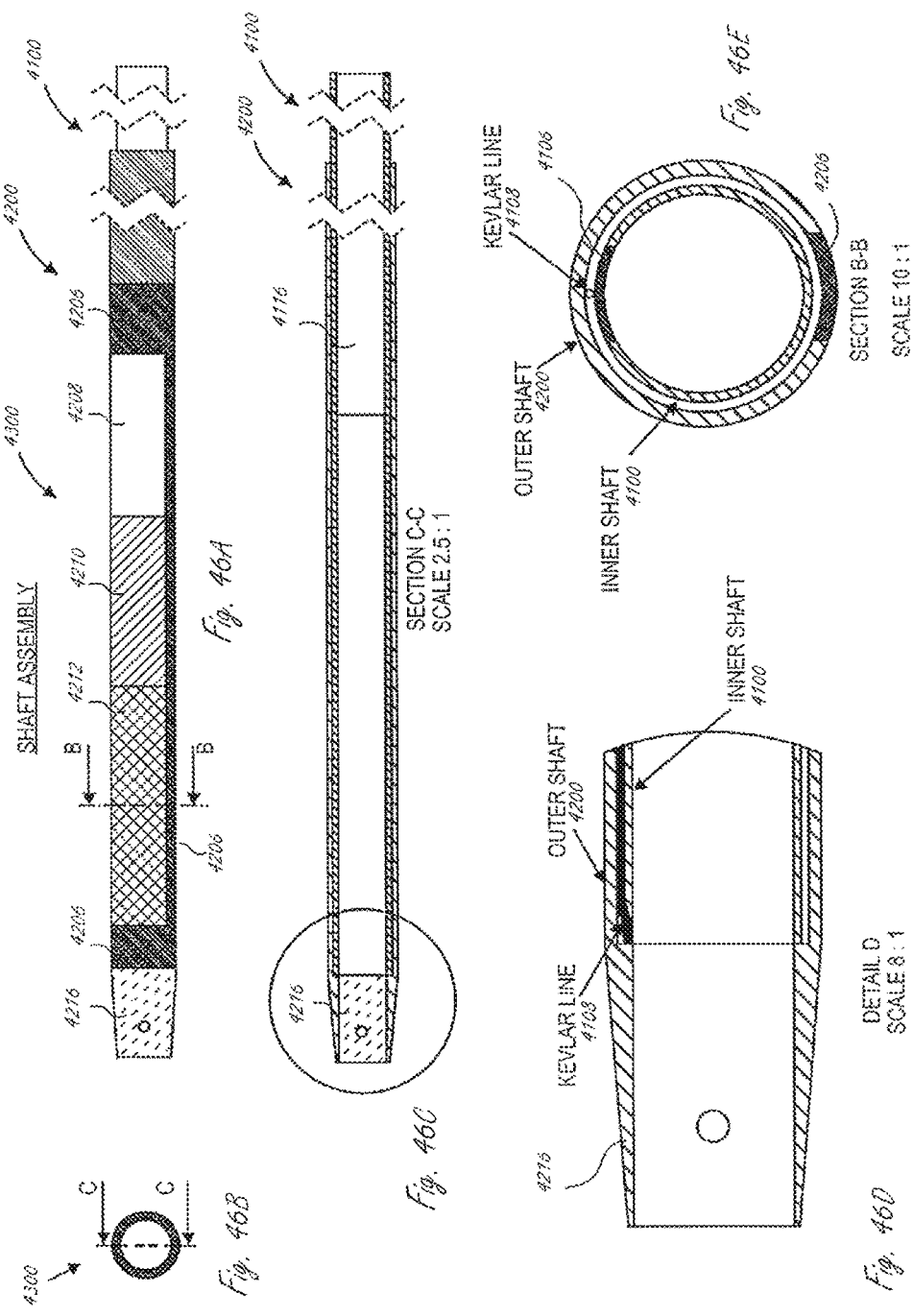

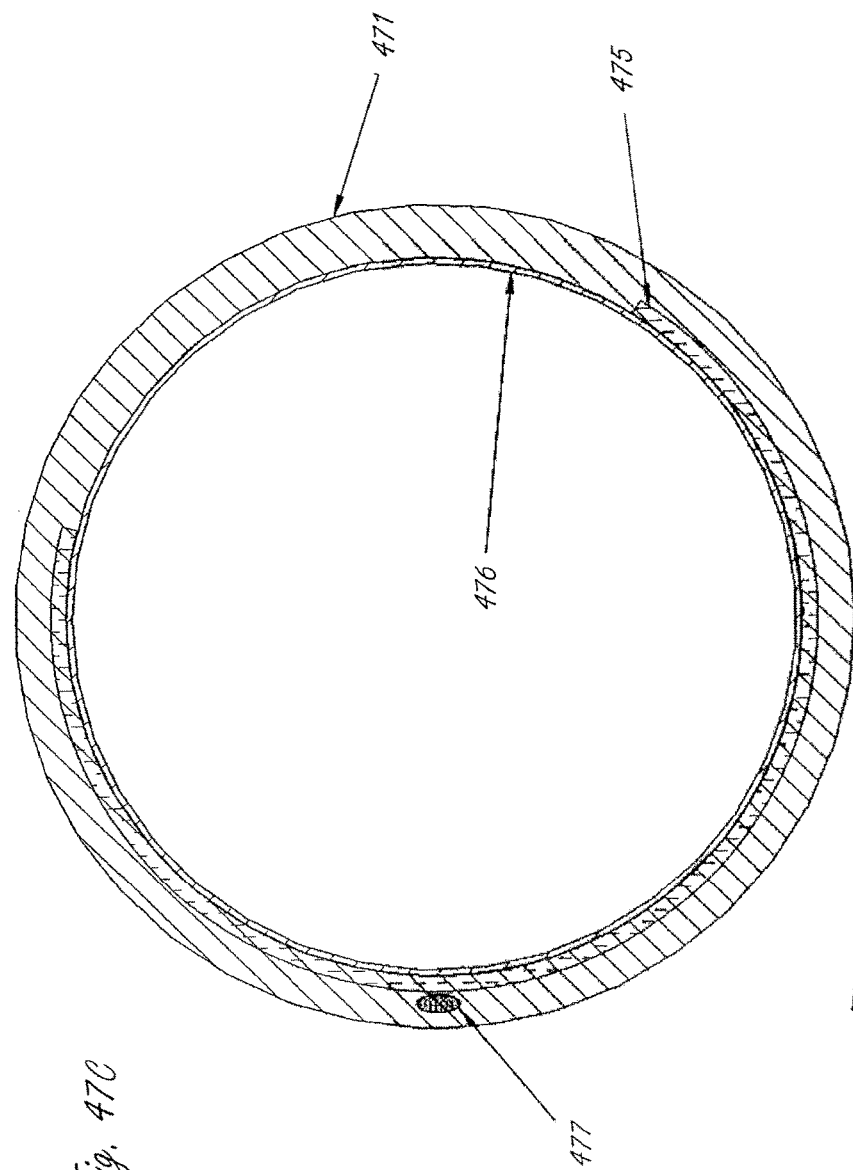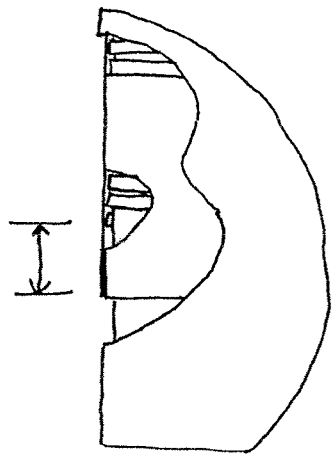

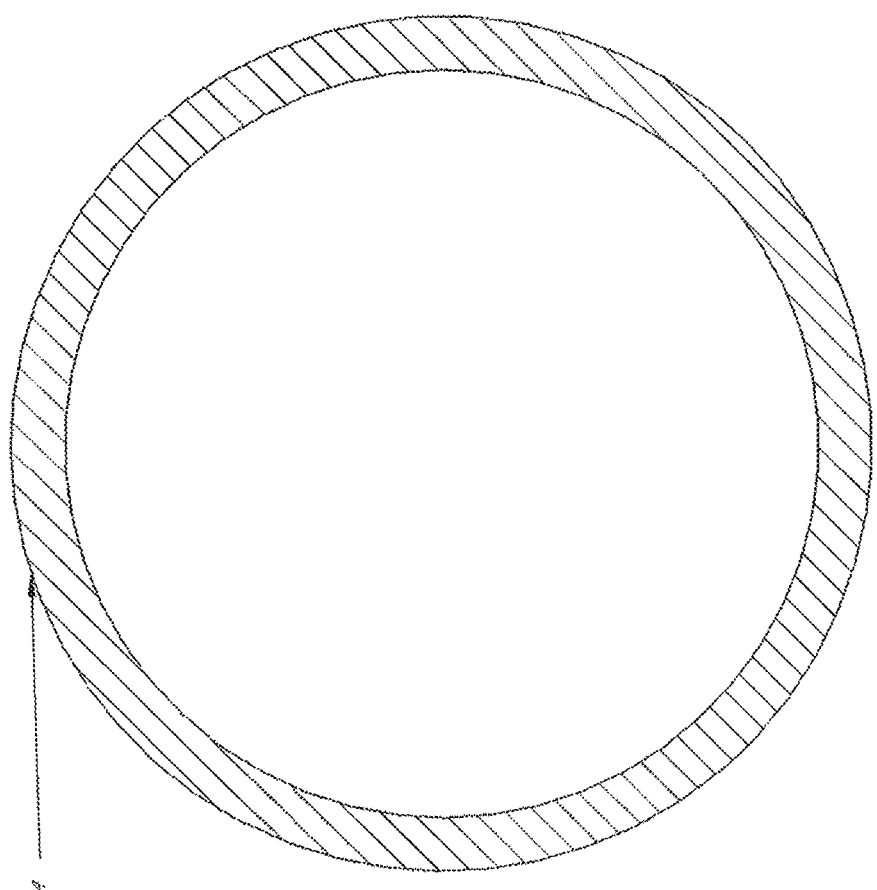

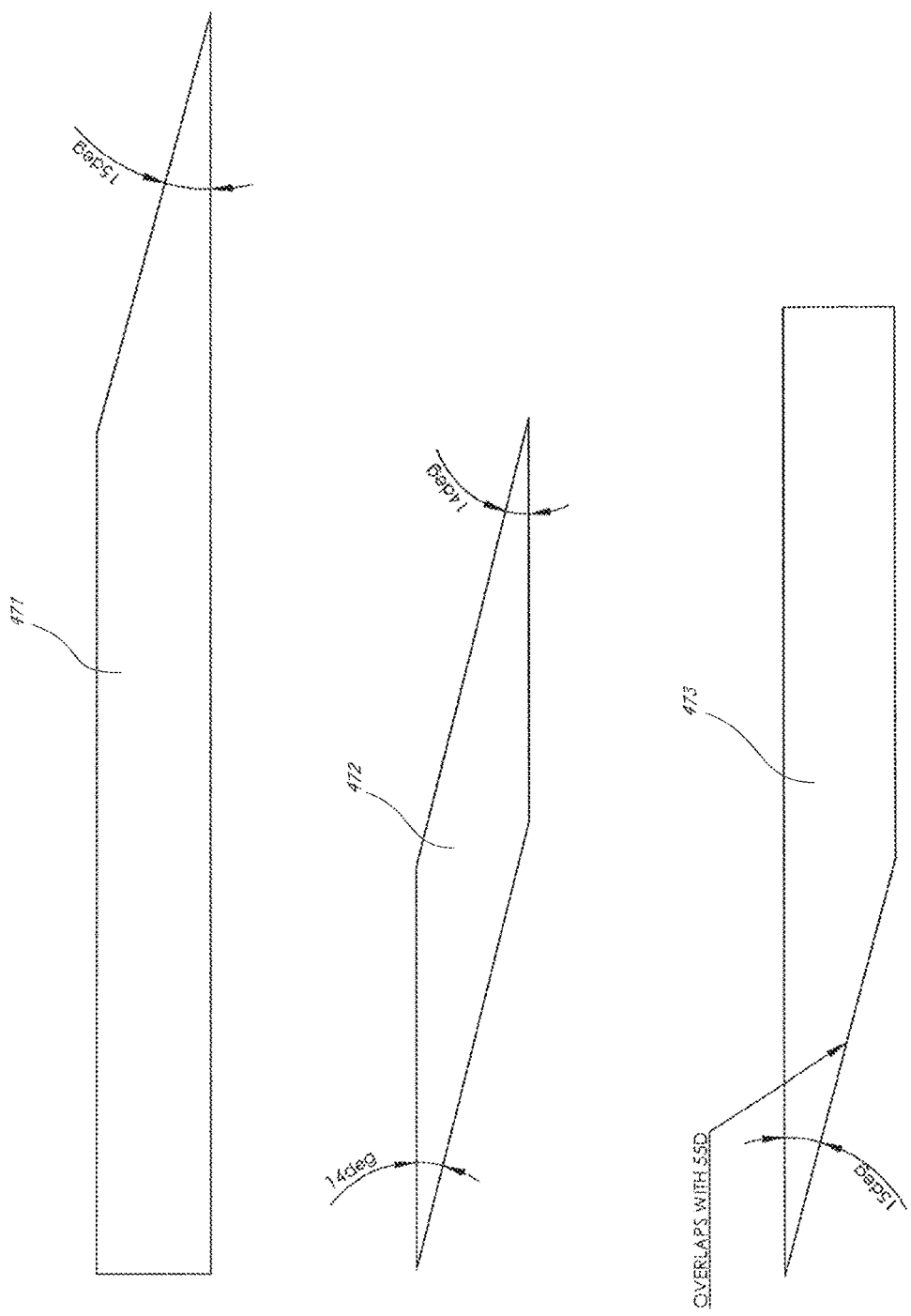

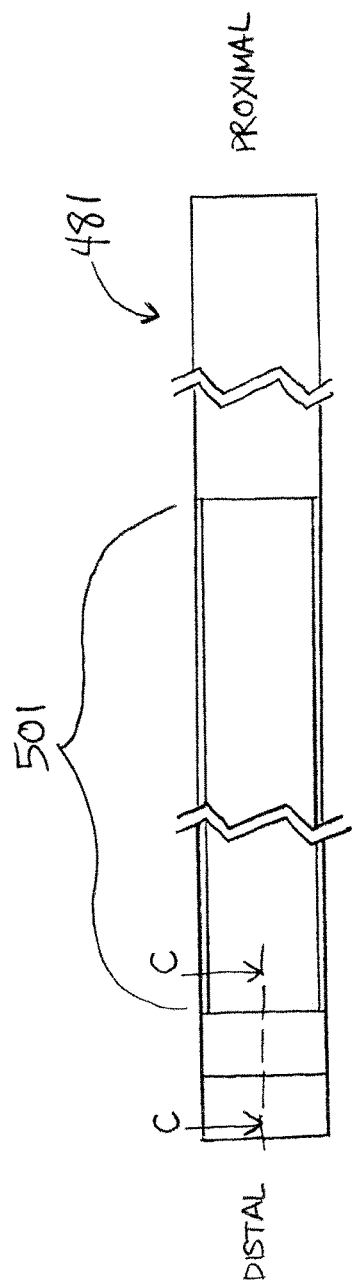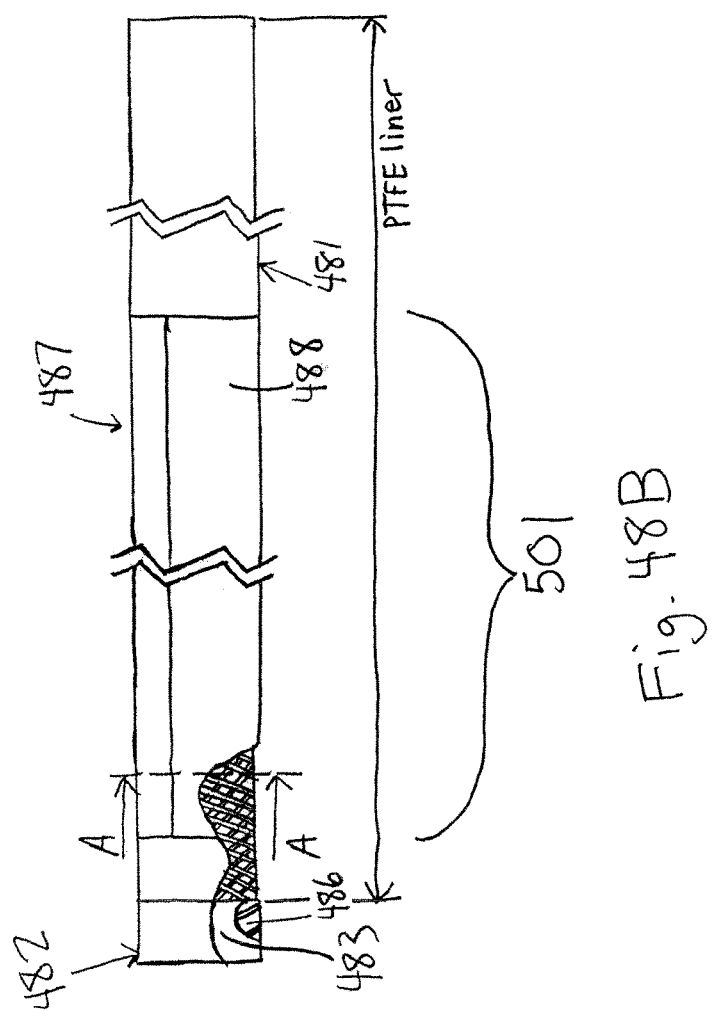
Fig. 48A
Fig. 48B

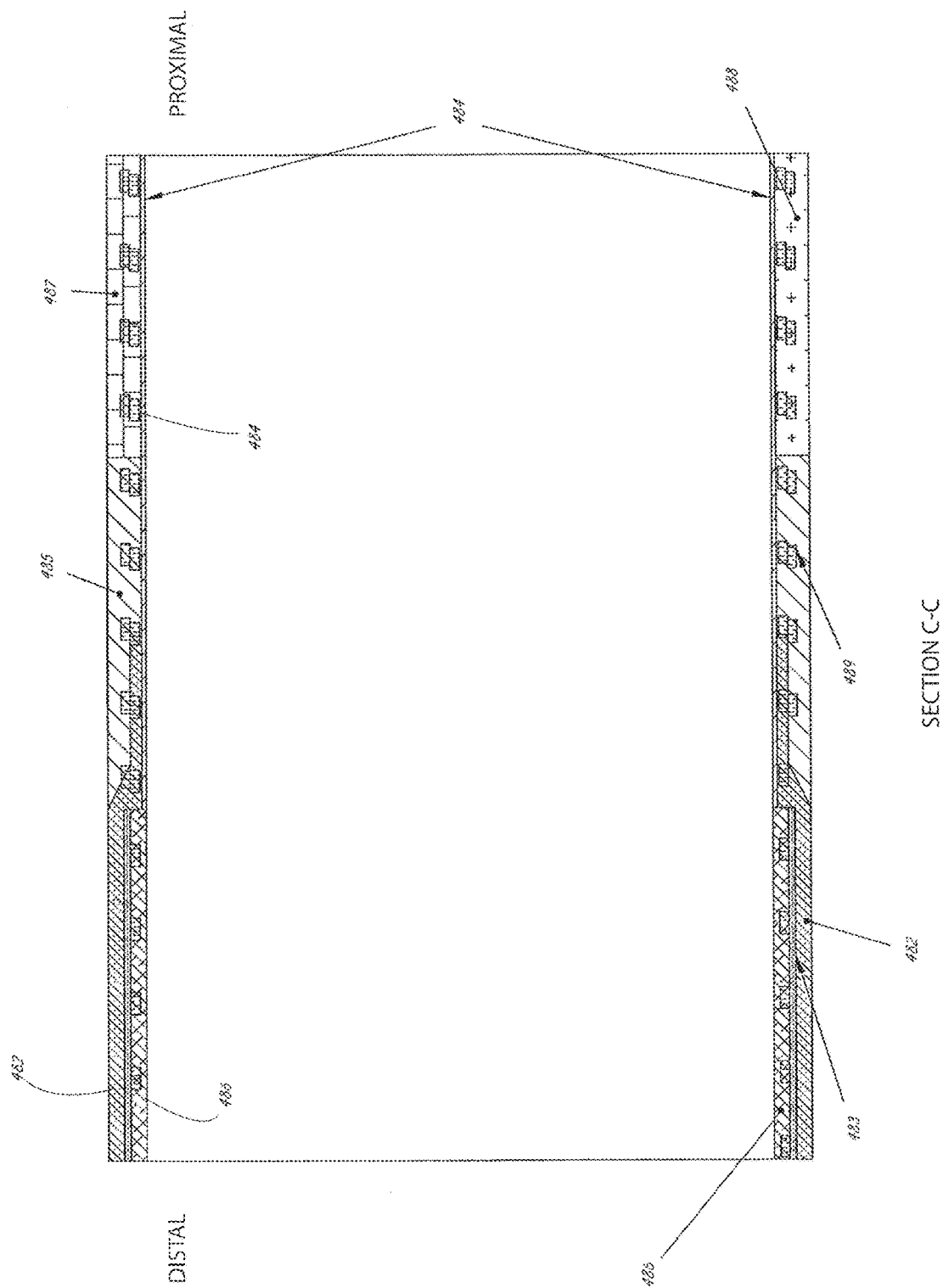

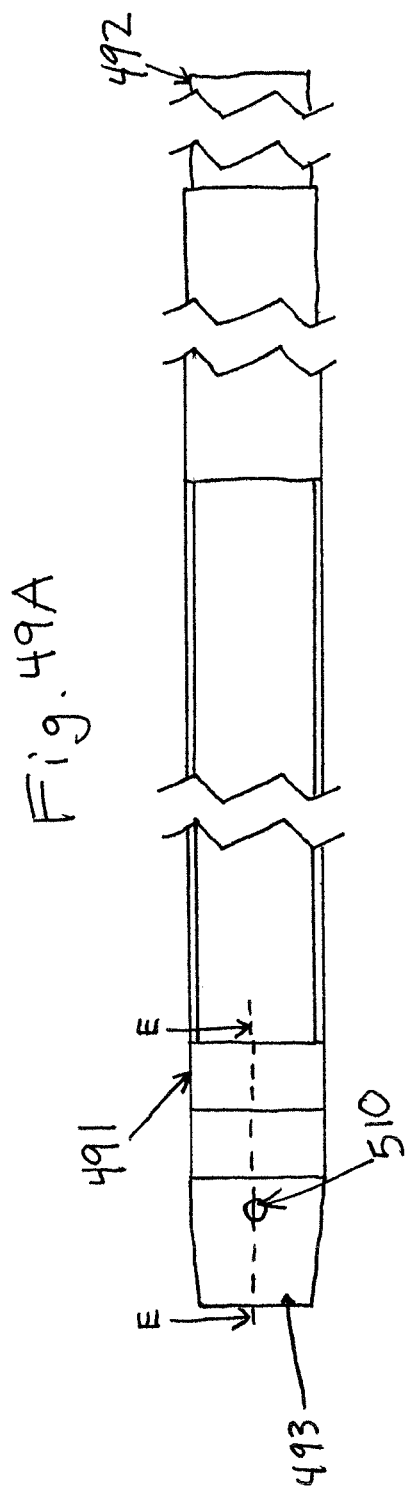
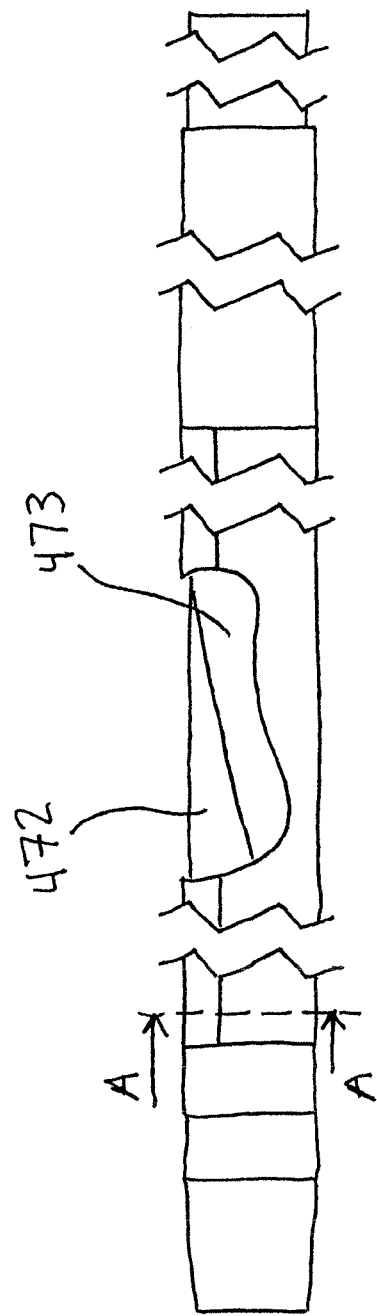
Fig. 49A
Fig. 49B

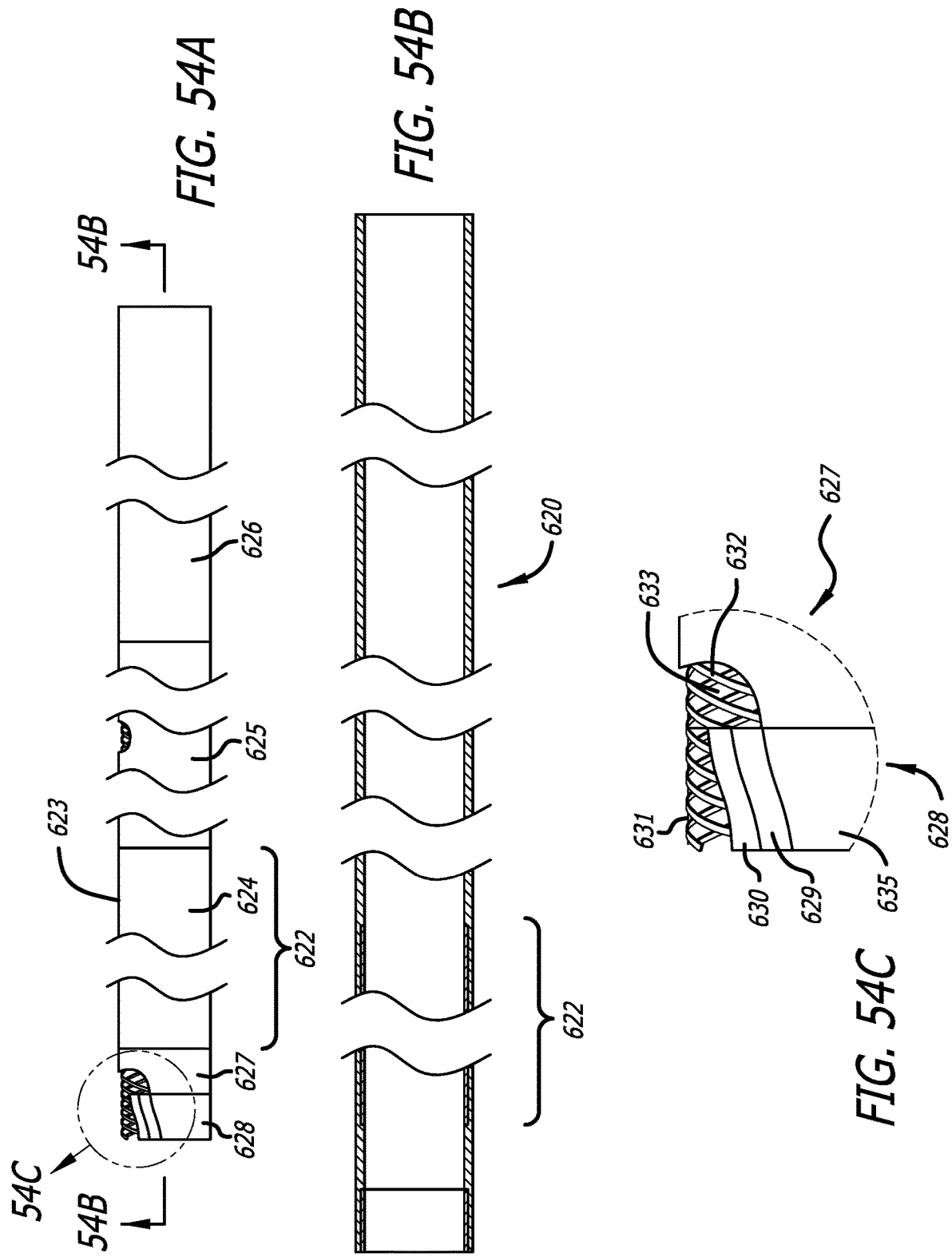

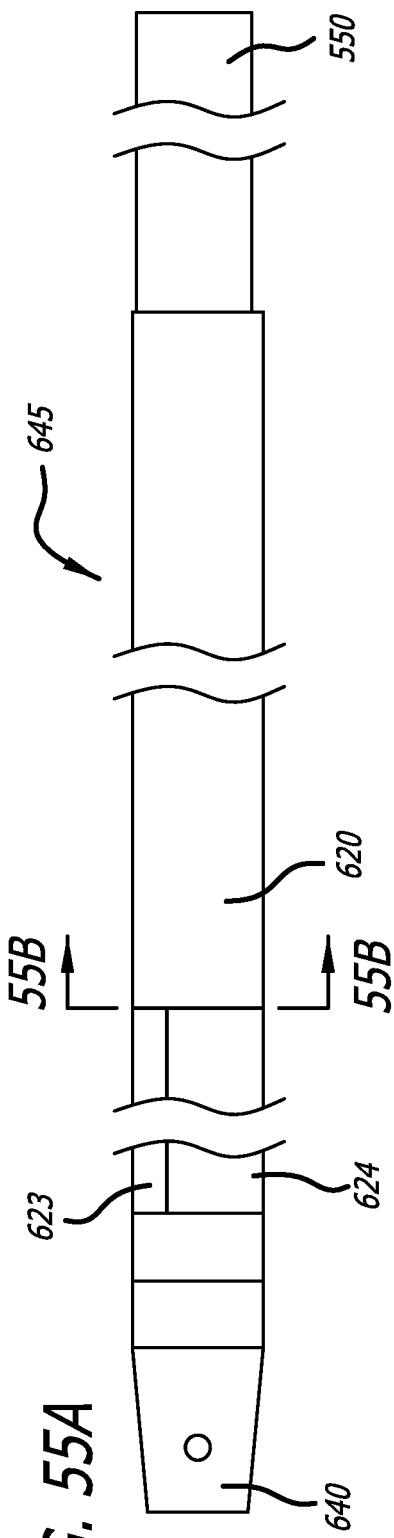
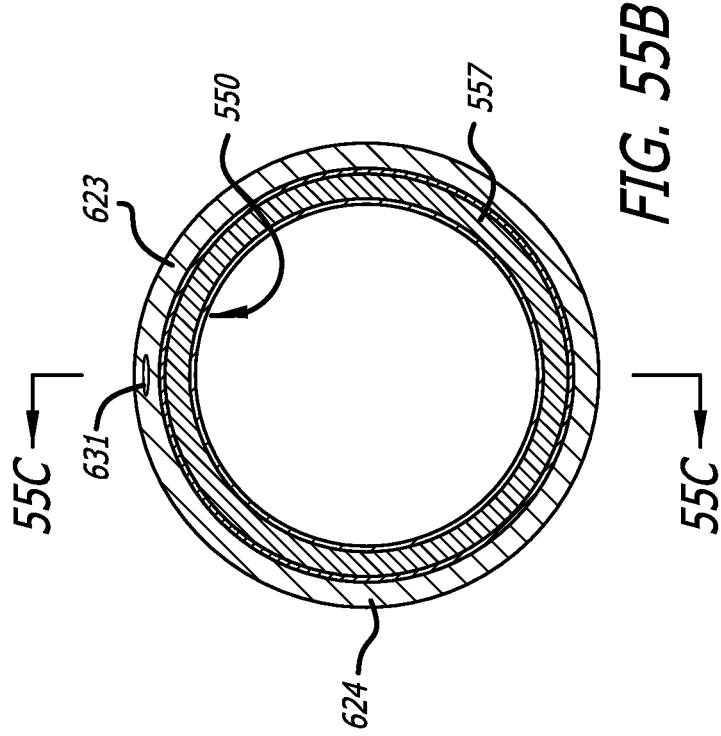

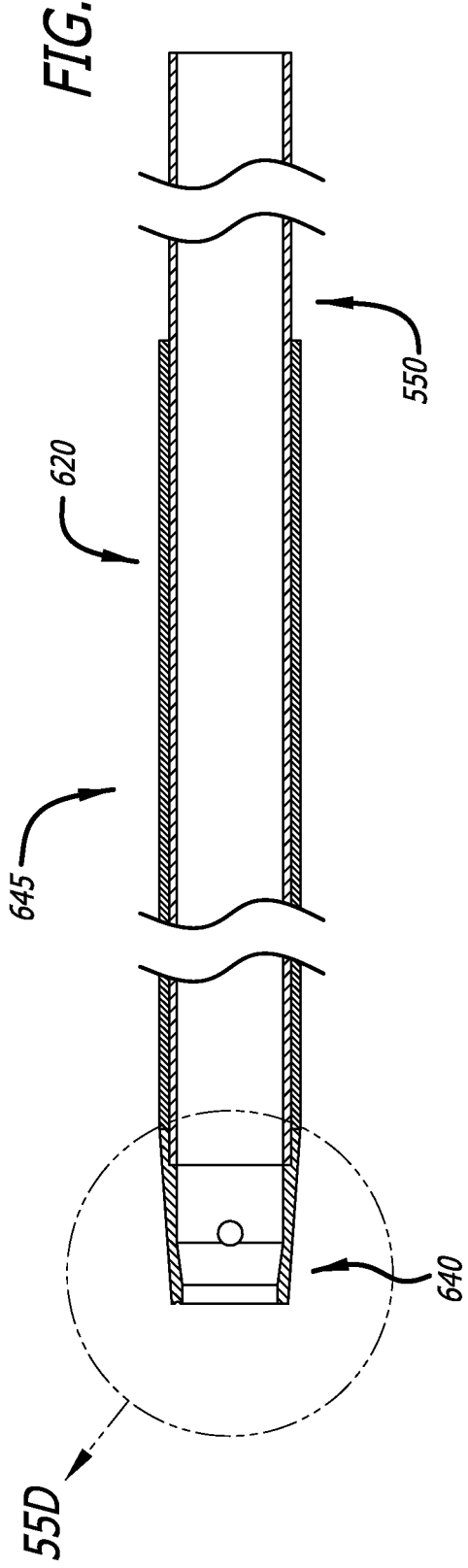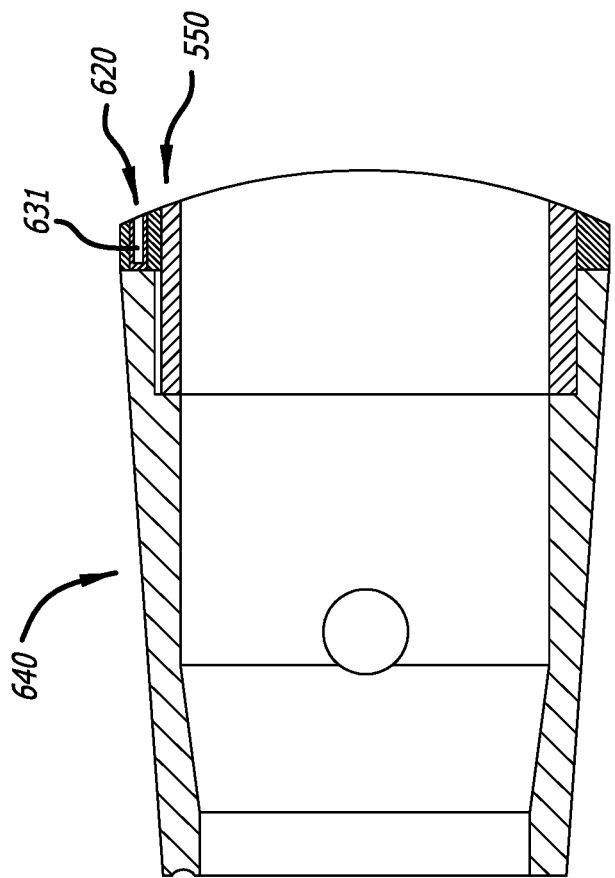
FIG. 55C
FIG. 55D

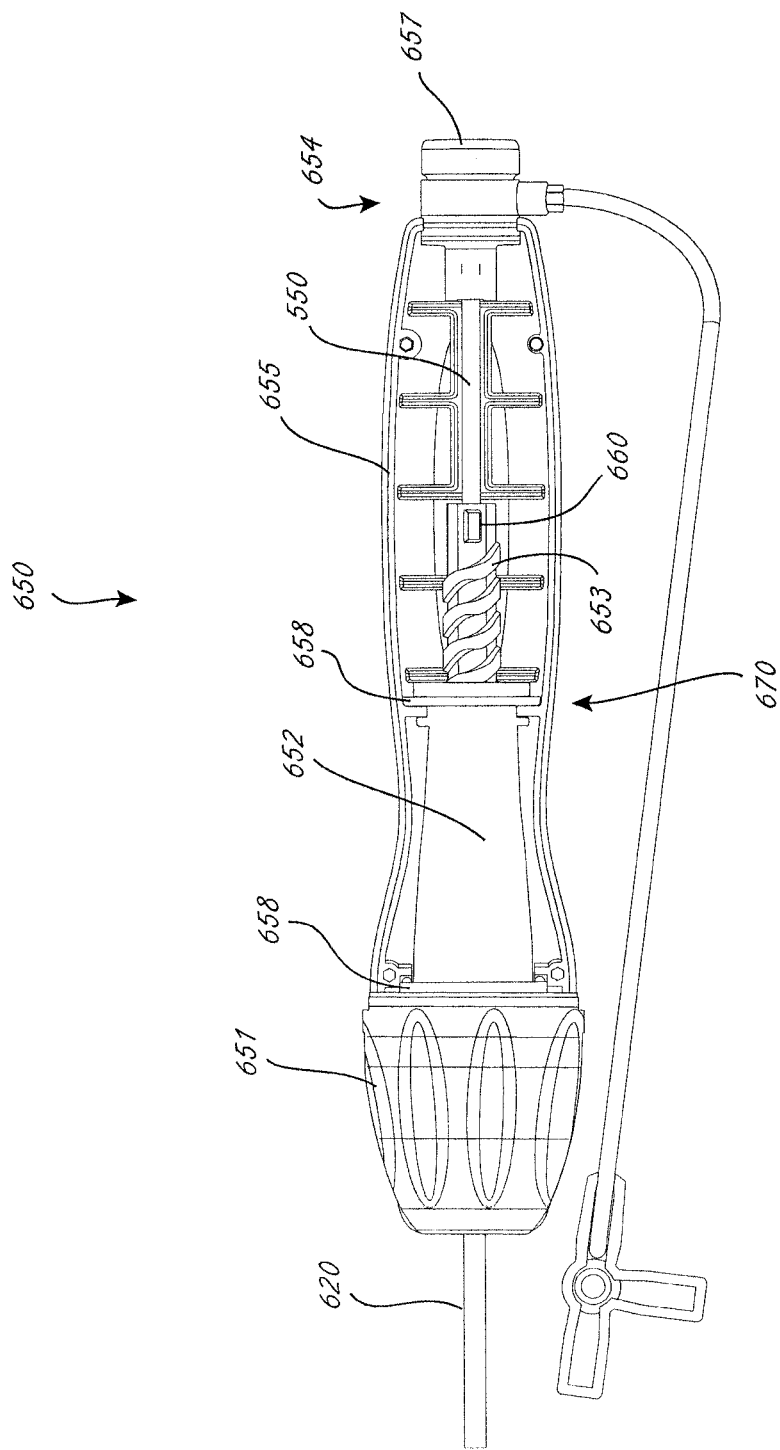

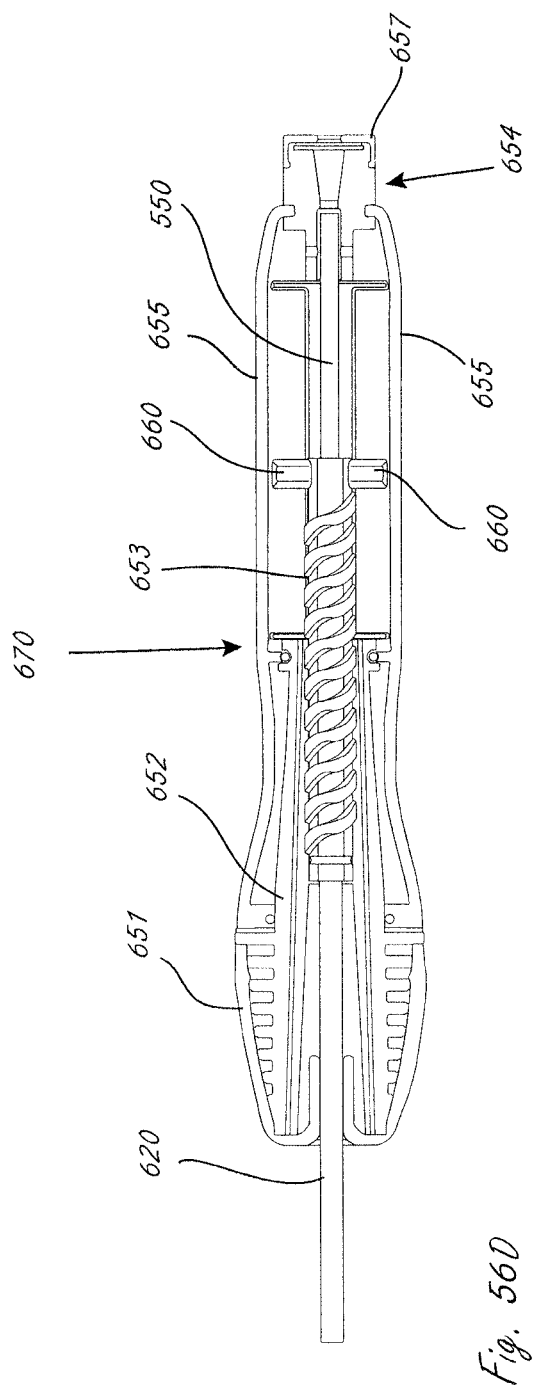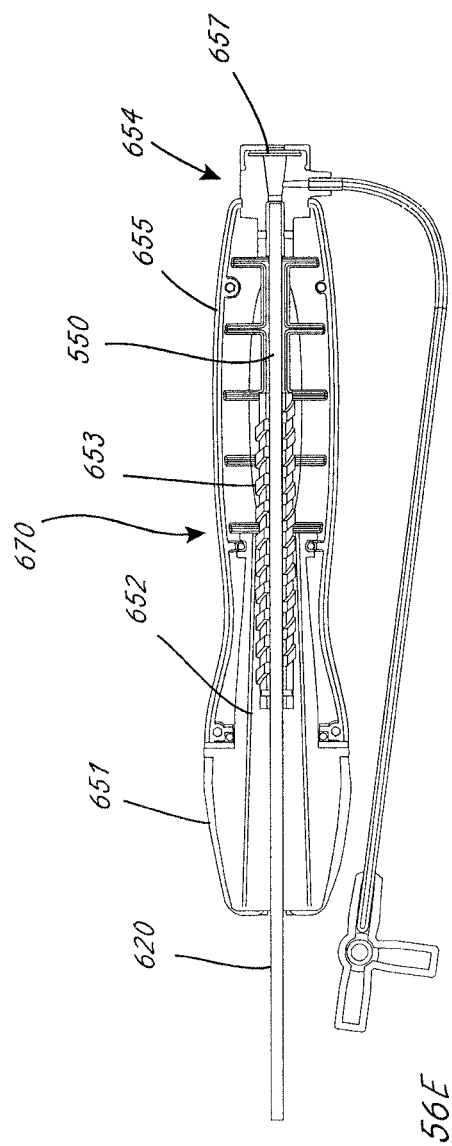
Fig. 56D
Fig. 56E

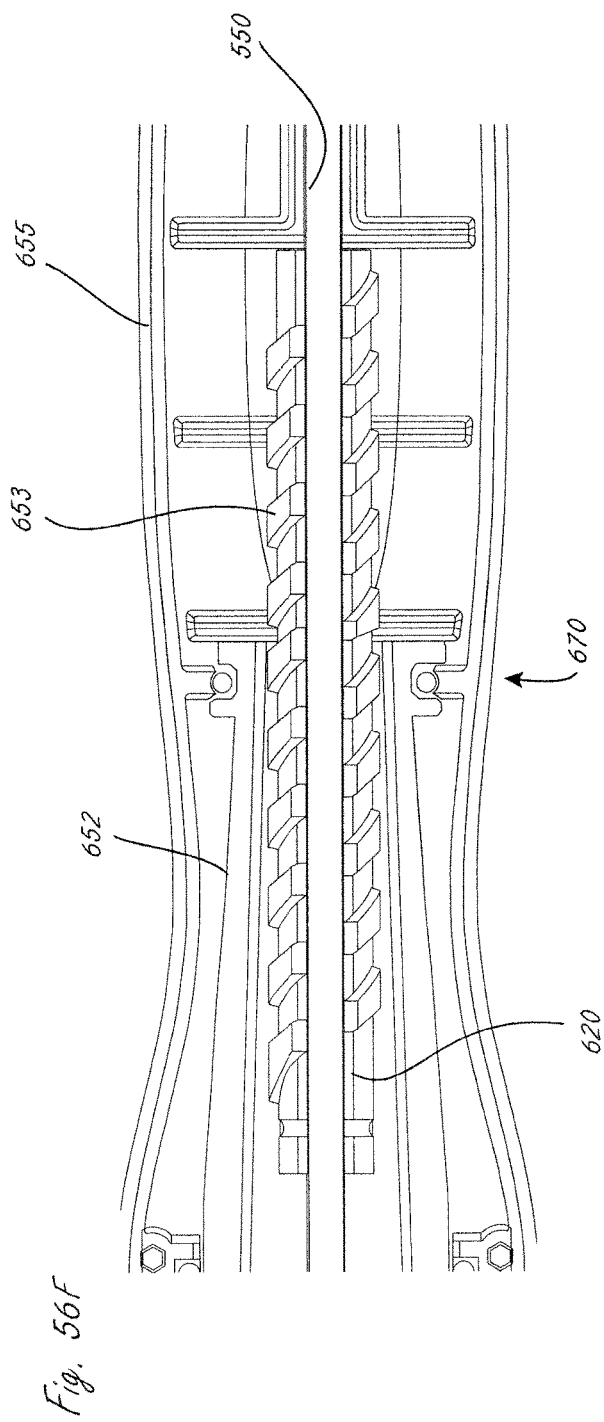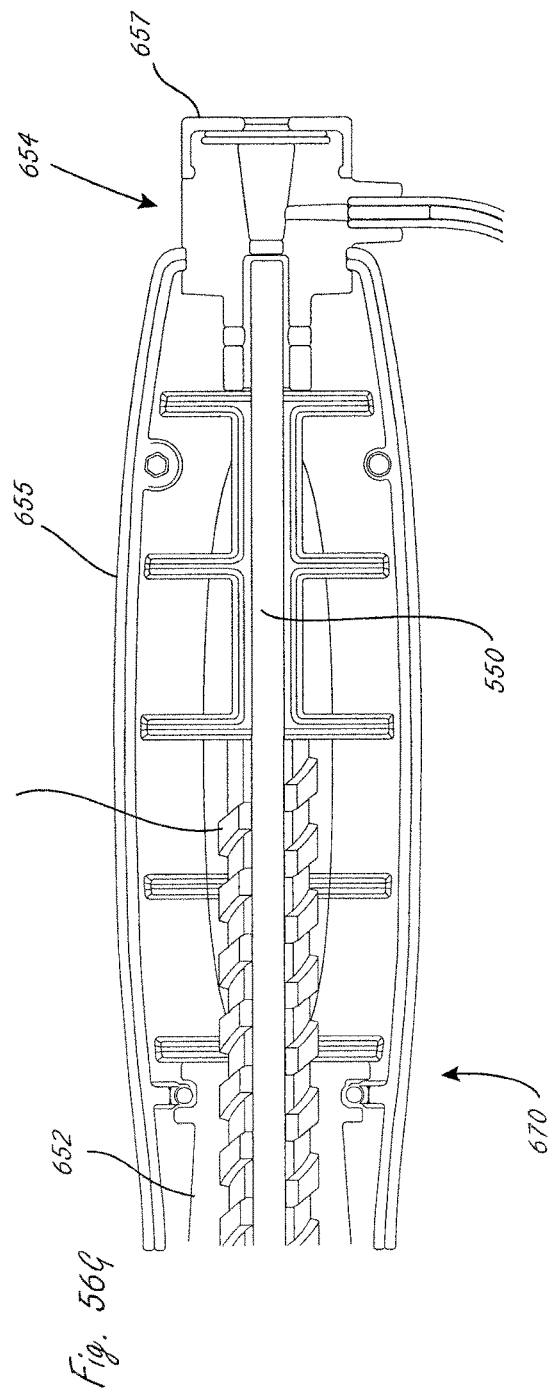

STEERABLE MEDICAL DEVICES, SYSTEMS, AND METHODS OF USE

CROSS REFERENCE TO RELATED APPLICATIONS

This application claims the priority of U.S. Provisional App. Ser. No. 62/152,741, filed Apr. 24, 2015, which is incorporated by reference herein.

INCORPORATION BY REFERENCE

All publications and patent applications mentioned in this specification are herein incorporated by reference to the same extent as if each individual publication or patent application was specifically and individually indicated to be incorporated by reference.

BACKGROUND

Steerable medical devices can be used in any application when a medical device needs to be steered, or bent. For example, steerable delivery devices can be used to deliver, or guide, medical devices or instruments to a target location within a subject. The delivery devices provide access to target locations within the body where, for example, diagnostic, therapeutic, and interventional procedures are required. Access via these devices is generally minimally invasive, and can be either percutaneous, or through natural body orifices. The access can require providing a guiding path through a body lumen, such as, for example without limitation, a blood vessel, an esophagus, a trachea and adjoining bronchia, ducts, any portion of the gastro intestinal tract, and the lymphatics. Once a delivery device has provided access to the target location, the delivery device is then used to guide the medical device or instrument to perform the diagnostic, therapeutic, or interventional procedure. An example of such a delivery device is a guide catheter, which may be delivered by steering it to its required destination, tracking it along a previously delivered guide wire, or both. The list of components being delivered for use percutaneously is large and rapidly growing.

Minimal outer dimensions of delivery devices can be important for minimizing the injury associated with delivery. Minimizing the wall thickness of a delivery device provides additional space for the medical device to be guided, while minimizing the injury associated with entry into the subject and the closure needed. Flexibility of a delivery device is important in allowing the guiding device to track or be steered to its target destination along tortuous paths while minimizing injury to the intervening tissues. A delivery device may also need to have compressive and tensile properties sufficient to support its delivery to the target site. When tracking around bends in the body, any kinks created in a guiding device can create an obstruction to the delivery of the medical device. When used as a steerable device, the distal end of a delivery device is preferably deflectable over a range of bend radii and responsive to the steering controls. A delivery device may also need to support torque transmitted from the handle to the distal region.

Once a delivery device is in place the delivery device preferably also supports torque around a distal bend such that the medical device may be rotated into position while sustaining some contact loads. Additionally, once in place the guiding device preferably is sufficiently stiff to support and guide the medical device to its target destination. A guiding device may also remain stable and not shift from one state of equilibrium to another either spontaneously or under the influence of forces being imparted to it from the delivery of the medical device or its own control mechanisms. As a delivery device often travels down fluid-filled lumens such as, for example without limitation, blood vessels, it should additionally incorporate a seal against fluids impinging upon its periphery and another at its distal end which interfaces with the medical device to maintain a seal around the delivery device.

There exists a need for improved steerable medical devices, such as steerable delivery devices.

SUMMARY OF THE DISCLOSURE

One aspect of the disclosure is a steerable medical device, comprising an inner flexible tubular member with an inner spine; an outer flexible tubular member axially fixed to the inner flexible tubular member at a fixation location distal to a steerable portion, the outer tubular member having an outer spine that is offset from the inner spine, and a linear reinforcing member extending within the outer spine; and an external controller operatively interfacing with the inner and outer flexible tubular members to put one of the inner and outer tubular members in tension and the other in compression, to steer the steerable portion.

In some embodiments the inner tubular member further comprises an inner linear reinforcing member extending within the inner spine. The linear reinforcing member and the inner linear reinforcing member can be 180 degrees away around the steerable medical device.

In some embodiments the linear reinforcing member is 180 degrees away from the inner spine around the steerable medical device.

In some embodiments the outer spine comprises a linear segment of first material extending less than 180 degrees around the outer tubular member. The first material can have a durometer greater than a second segment of material extending more than 180 degrees around the outer tubular member.

In some embodiments the outer tubular member further comprises a braided reinforcing member in the steerable portion. The linear reinforcing member can be woven into the braided reinforcing member.

In some embodiments a distal end of the linear reinforcing member is further distally than a distal end of the steerable portion. A distal end of the linear reinforcing member can extend substantially to a distal end of the outer tubular member.

In some embodiments a distal end of the linear reinforcing member extends to a location where the inner tubular member and outer tubular member are axially secured together.

One aspect of the disclosure is a steerable medical apparatus, comprising: an external controller comprising an actuator and a driving member; and an elongate steerable device including first and second tubular members axially fixed to one another at a location distal to a steerable portion, one of the first and second tubular members within the other, a proximal end of the first tubular member operatively fixed to the driving member such that axial movement of the driving member causes axial movement of a proximal end of the first tubular member, the actuator operatively interfaced with the driving member such that in response to actuation of the actuator in a first direction, the driving member moves proximally, the first tubular member is put in tension and the second tubular member is put in compression, and the steerable portion is steered in first direction, and in response to actuation of the actuator in a second direction opposite the first direction, the driving member moves distally, the first tubular member is put in compression and the second tubular member is put in tension, and the steerable portion is steered in a second direction different than the first direction.

In some embodiments the first tubular member is an outer tubular member, the second tubular member being an inner tubular member within the tubular member.

In some embodiments the actuator is coupled to a nut, and the nut interfaces the driving member.

In some embodiments the driving member comprises an external thread, the actuator operatively interfaced with the external thread. The actuator can be coupled to a nut, and wherein the nut can interface the external thread. In some embodiments the actuator operatively interfaces with the external thread at a location axially spaced from a proximal-most end and a distal-most end of the thread. The proximal end of the first tubular member can be fixed to the driving member within a lumen of the driving member. The second tubular member can be disposed within the lumen of the driving member.

In some embodiments a proximal end of the second tubular member is axially fixed to a component of the external controller that is not configured to move axially when the driving member moves axially. In some embodiments the proximal end of the second tubular member is axially fixed to a valve body.

In some embodiments the driving member interfaces a handle shell with a female and male interface that prevents rotation of the driving member in response to actuation of the actuator.

BRIEF DESCRIPTION OF THE DRAWINGS

FIGS. 16A and 16B illustrate a portion of a tubular member formed with the cut pattern from FIG. 15, while

FIGS. 42A-42G illustrate an exemplary embodiment of a portion of a steerable device that includes materials with different durometers.

FIGS. 43A-43D illustrate an exemplary embodiment of a portion of a steerable device that includes materials with different durometers.

FIGS. 44A-44C illustrate an exemplary inner tubular member. FIG. 44A is a top view. FIG. 44B is a view rotated 90 degrees relative to the FIG. 44A view, and FIG. 44C is a view rotated 180 degrees relative to the view in FIG. 44A (and 90 degrees relative to the view in FIG. 44B).

45A is a top view. FIG. 45B is a view rotated 90 degrees from the view in FIG. 45A, and FIG. 45C is a view rotated 180 degrees from the view in FIG. 45A (and 90 degrees from the view in FIG. 45B).

FIGS. 46A-46E illustrate views of an assembly including the inner and outer tubular members from FIGS. 44 and 45.

FIGS. 47A-47I illustrate an exemplary inner tubular member.

FIGS. 48A-48D illustrate an exemplary outer tubular member.

FIGS. 49A-49D illustrate a steerable device comprising the inner and outer tubular members from FIGS. 47A-47I and FIGS. 48A-48D.

FIGS. 54A, 54B, and 54C illustrate an exemplary outer tubular member.

FIGS. 55A, 55B, 55C, and 55D illustrate exemplary bonding of inner and outer tubular members.

FIGS. 56A, 56B, 56C, 56D, 56E, 56F, 56G, and 56H illustrate an exemplary handle that can impart bi-directionality to a steerable medical device.

DETAILED DESCRIPTION

The disclosure relates generally to steerable medical devices, including steerable guide devices, and their methods of use. When a steerable medical "delivery" device is described herein it is merely an example of the steerable medical devices described herein. Steerable delivery devices can be used to deliver, or guide, any type of suitable medical device or instrument therethrough to a target location within a patient's body. For example, a steerable delivery device can be used to deliver, or guide, a medical device into bodily lumens or cavities such as, for example without limitation, a blood vessel, an esophagus, a trachea and possibly adjoining bronchia, any portion of the gastrointestinal tract, an abdominal cavity, a thoracic cavity, various other ducts within the body, the lymphatics, one or more chambers of the heart, etc. Once a steerable delivery device has gained access to a target location within the subject, one or more medical devices or instruments is delivered, or guided, to the target location to carry out one or more medical interventions. In some methods of use steerable delivery device described herein are tracked along a previously positioned guide wire, the positioning of which is known in the art. In some embodiments the steerable concepts described herein can be applied to steerable medical devices such as catheters that have any diagnostic and/or therapeutic functionality, and which are advanced through a separate guide device.

Figure 1:
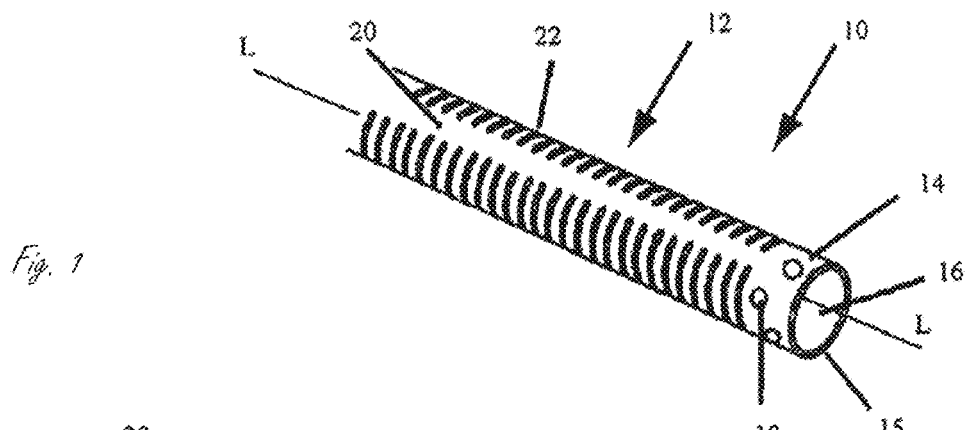
FIG. 1 is a perspective view of a steerable portion of a steerable medical device.

FIG. 1 is a perspective view of a distal portion of an exemplary steerable delivery device. Steerable device 10 includes steerable portion 12 and has distal end 15. Steerable portion 12 includes an outer tubular member 14 and inner tubular member 16. Outer tubular member 14 has an inner surface defining a lumen therein, and inner tubular member 14 is sized to be disposed within the inner lumen of outer tubular member 14. Outer tubular member 14 and inner tubular member 16 are permanently axially fixed relative to one another at fixation location 18 along the length of steerable device 10. That is, at fixation location 18, the inner and outer tubular members are not adapted to move distally or proximally relative to one another and are permanently axially fixed to one another. "Permanent" fixation as used herein generally refers to fixation that occurs during manufacture of the device such that one or more components are not adapted or intended to be disengaged from one another during use of the device. As used herein, when the tubular members or components are described as being axially fixed relative to one another at a certain location, the fixation can be permanent fixation or temporary fixation unless specifically indicated to be one or the other. Fixation location 18 is located distal to steerable portion 12. At locations proximal to fixation location 18, inner tubular member 16 and outer tubular member 14 are axially movable relative to one another. That is, along steerable portion 12, inner tubular member 16 and outer tubular member 14 are adapted to move axially relative to another, which provides for the steering of the device, described below. Outer tubular member 14 has slots 22 formed therein, which define spine 20. Spine 20 extends along a length of steerable portion 12. Slots 22 are shown substantially perpendicular to the longitudinal axis "L" of steerable portion 12, when steerable portion 12 is in a straightened configuration as shown in FIG. 1. Inner tubular member 16 also has slots formed therein (not shown) in the steerable portion, which define a spine (not shown).

Figure 2A:
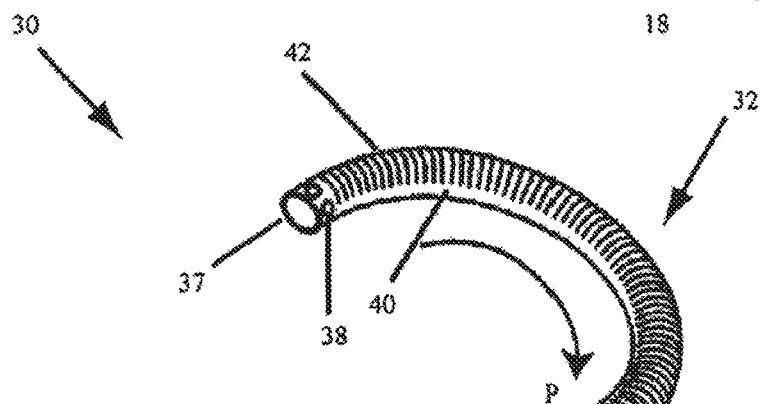
FIGS. 2A, 2B, and 2C illustrate steering of exemplary steerable portions of steerable medical devices.
Figure 2B:
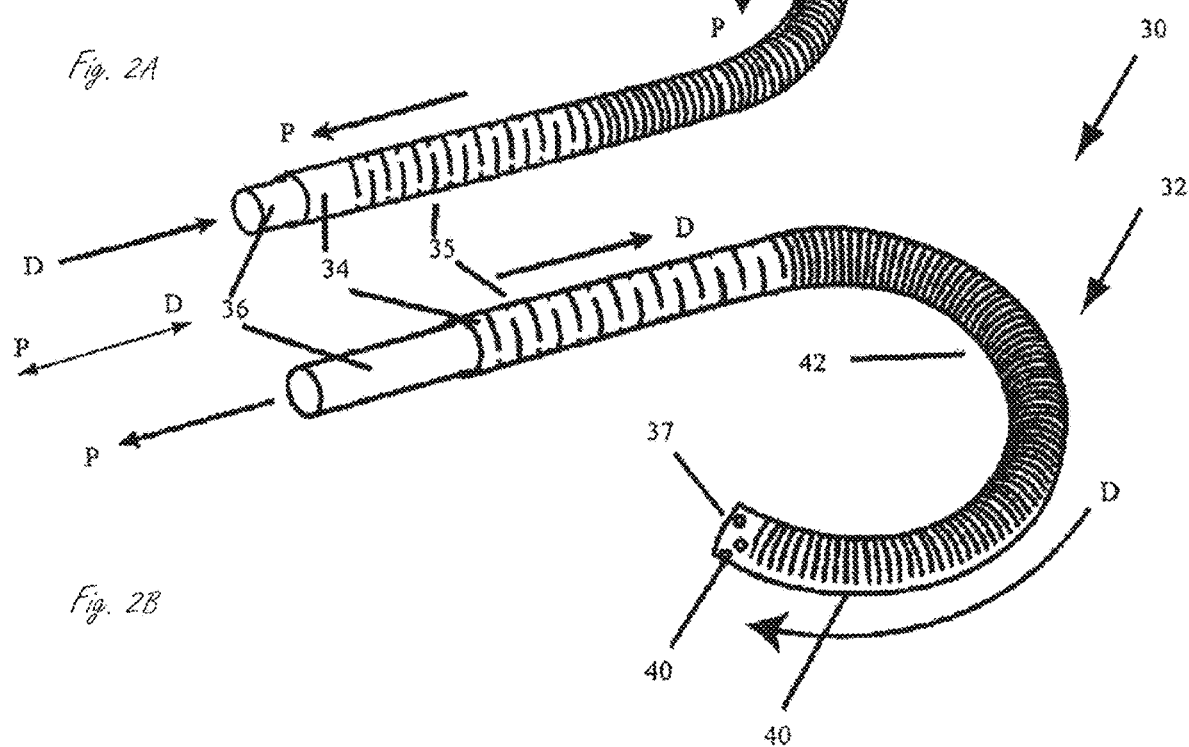

FIGS. 2A and 2B illustrate an exemplary embodiment of a steerable delivery device. Steerable device 30 has a distal end 37 and includes outer tubular element 34 and inner tubular element 36 which are axially immovable relative to one another at fixation location 38, but are axially movable proximal to fixation location 38. Outer tubular element 34 includes a plurality of slots 42 formed therein to define spine 40. Inner tubular element 36 also includes a plurality of slots formed therein (not shown) to define a spine (not shown). In FIGS. 2A and 2B, the spines are disposed substantially 180 degrees apart from one another. FIG. 2A illustrates steerable portion 32 deflected, or steered, into a first bent configuration, while FIG. 2B illustrates steerable portion 32 steered into a second bent configuration different than the first bent configuration. To steer the steerable portion into the configuration shown in FIG. 2A, a proximal portion of outer tubular member 34 is moved axially, and specifically proximally, relative to inner tubular member 36, while the tubular elements 34 and 36 are axially fixed relative to one another at fixation location 38. This can be accomplished by pulling outer tubular member 23 in a proximal "P" direction while maintaining the position of inner tubular member 36, by pushing inner tubular member 36 in a distal "D" direction while maintaining the position of outer tubular member, or by a combination thereof. The relative axial movement of the inner and outer tubular members as shown in FIG. 2A applies substantially opposing compressive and tensile forces to the spines of the tubular members, thus deflecting, or steering, the device in the direction of spine 40 of outer tubular member 34, as is shown in FIG. 2A. FIG. 2B illustrates a step of steering device 30 in the substantially opposite direction from that shown in FIG. 2A. To steer device 30 into the configuration shown in FIG. 2B, inner tubular member is moved proximally relative to outer tubular member 34. This can be performed by moving the outer tubular member distally, moving the inner tubular member proximally, or a combination thereof. This relative axial movement applies substantially opposing compressive and tensile forces to the spines in steerable portion 32 of device 30, thereby deflecting the device in a direction substantially opposite that of spine 40 of outer tubular member 34.

Figure 2C:
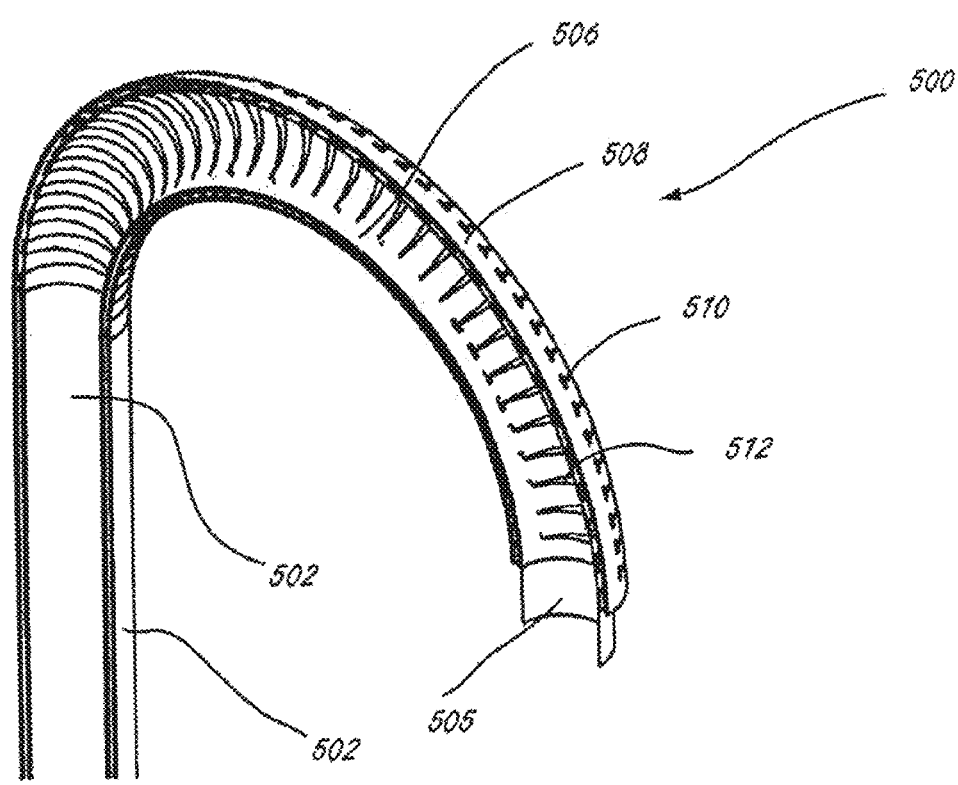

FIG. 2C shows a sectional view of the steerable portion from FIG. 2B, including optional floating tubular member 505 disposed within inner tubular member 504. Steerable portion 500 includes inner tubular member 504 and outer tubular member 502. Inner tubular member 504 has interrupted slots 512 formed therein to define spine 506. Outer tubular member 502 has interrupted slots 510 formed therein to define spine 508. The steerable portion is bent along the axis of spine 506. Spine 508 and spine 506 are substantially 180 degrees apart from one another (i.e., they are on substantially opposite sides of steerable portion 500).

To steer steerable portion 500 into the configuration shown in FIG. 2C (also shown in FIG. 2B), inner tubular member 504 is pulled in the proximal direction relative to outer tubular member 502, as is illustrated in FIG. 2B. Pulling on the inner member 504 applies a tensile force to inner spine 506. Because inner and outer tubular members 504 and 502 are axially fixed relative to one another at a location distal to the steerable portion, pulling on inner member 504 relative to outer tubular member 502 results in a compressive force applied to the distal end of the steerable portion of outer tubular member 502. The compressive force begins to compress slots 510 on outer tubular member 502. Compression of outer slots 510 causes outer tubular member to bend in the direction shown in FIG. 2C, and the bending stops when inner slots 510 are closed. Thus, outer slots 510 limit the degree of the bend of steerable portion 500. The same type of bending that is shown in FIGS. 2B and 2C would occur if outer tubular element 502 were pushed distally relative to inner tubular member 504.

If outer tubular member 502 were pulled proximally relative to inner tubular member 504 (or if inner tubular member 504 were pushed distally relative to outer tubular member 502), steerable portion 500 would bend in the manner shown in FIG. 2A. The degree of the bend would be limited by inner slots 512.

FIG. 2C illustrates an embodiment of a medical device including a floating tubular member, which may be referred to herein as a floating liner. In general, a floating liner is disposed within an outer structure. In the exemplary embodiment in FIG. 2C, the outer structure includes the inner and outer tubular members. The outer structure generally provides structural and mechanical properties for the delivery device, and the floating liner provides lubricity for a medical device or instrument to be advanced therethrough. A floating liner is generally impermeable as well. A floating liner "floats" with a portion of the outer structure. That is, the floating liner is not fixed to a portion of the outer structure in which it floats. In the exemplary embodiment in FIG. 2C, the floating liner floats within the steerable portion (i.e., is not attached to the steerable portion). In general, a floating liner is attached to the outer structure at a location proximal to the steerable or bendable portion of the device. For example, in the embodiment in FIG. 2C, the floating liner is attached to the outer structure at a location proximal to the steerable portion. A floating liner doesn't impede the ability of the outer structure to move as it is steered, bent, actuated, receives forces applied thereto, etc.

In some embodiments the floating liner is a lubricious polymer tube. In some embodiments the floating liner includes wire windings and/or axially laid wires.

The outer structure in which the floating liner floats can be any suitable tubular member. For example, the outer structure can be a catheter, guiding device, a steerable device, etc. In some embodiments the outer structure has a neutral bending preference but is not intended to be steered. In this embodiment the outer structure provides axial and radial stiffness thereby limiting the likelihood of kinks while the floating liner provides lubricity and is additionally restrained from kinking by the outer structure.

FIGS. 2A and 2B also show proximal portion 35 of device 30, which is proximal to steerable portion 32, having a substantially neutral portion designed to have no preferential bending axis while at the same time transmitting axial force and torque applied at a proximal end of the device (not shown).

In some embodiments, the inner and outer tubular members are adapted to have opposing compressive and tensile loads applied thereto to steer the steerable portion. In some embodiments at least one of the tubular members has a neutral bending axis. A neutral bending axis, as used herein, generally refers to an axis of the tubular member along which there is substantially no axial displacement in response to a compressive and/or tensile force applied thereto. Axial displacement along the neutral bending axis, in response to a compressive and/or tensile force applied thereto, is less than axial displacement of structures elsewhere in the tubular member. In particular, axial displacement along the neutral bending axis is minimal relative to axial displacement of structures elsewhere in the tubular member. Examples of a neutral bending axis include spine 382 in FIG. 21 and spines 412 and 414 in FIG. 23.

In some embodiments at least one of the tubular members is adapted to offset the neutral bending axis relative to the opposite tubular member. The neutral bending axes of the tubular members can be offset to be approximately tangent to opposite sides of the opposing members, making the neutral bending axis offset equal to the diameter of the device, thus providing the highest possible bending leverage ratio for a given device diameter.

Figure 25:
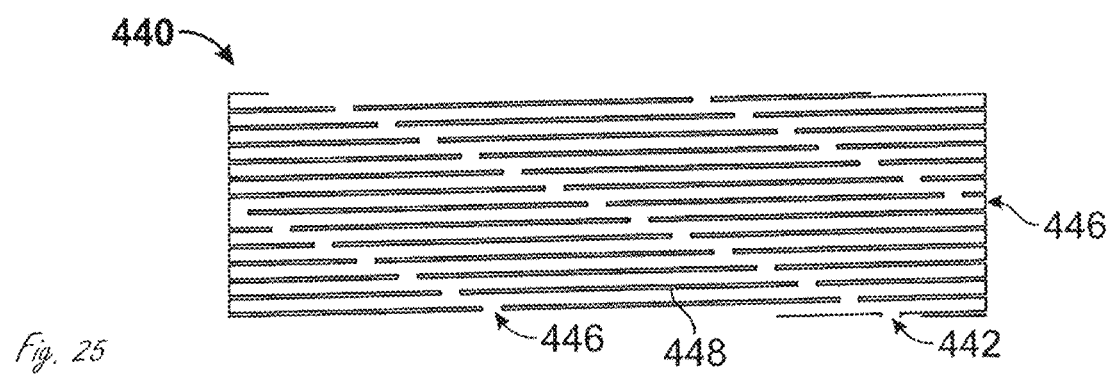
FIG. 25 illustrates a flattened portion of an exemplary tubular member. The slots create a relatively neutral pattern.

The tubular members described herein may exhibit preferential or neutral bending behavior. Neutral bending behavior implies that the displacement for a given radially applied load (from the edge of the tubular member through the longitudinal axis of the tubular member) will be independent of the radial angle from which the load was applied. In contrast, in a non-neutral structure the displacement associated with a radial load will change as a function of the radial angle. An exemplary tubular member tending towards neutral bending behavior is shown in FIG. 25 or the uninterrupted spiral pattern of FIG. 25 which is essentially a spring.

In some embodiments the inner and outer tubular elements are adapted to be rotated relative to one another to enhance the steerability of the steerable portion. The tubular elements can rotate relative to one another yet remain axially fixed relative to one another at a location distal to the steerable portion. In these embodiments, in addition to axial forces being applied to one or more tubes, one or more tubular members are also rotated with respect to each other to steer the steerable portion.

In some embodiments only one of the inner and outer tubular members has at least one slot defining a spine along the steerable portion, while the other does not have any slots along the steerable portion. For example, in FIGS. 2A and 2B, outer tubular member 34 can have a slot and a spine while inner tubular member 36 does not have a slot formed therein. Alternatively, inner tubular member 36 can have at least one slot and a spine while outer tubular member 34 does not have a slot formed therein. The steerable portion can be steered as described herein if at least one of the inner and outer tubular members is adapted to preferentially bend in a first direction.

In the embodiment in FIGS. 1 and 2 the slots in both tubular members are substantially perpendicular to the longitudinal axis of the steerable portion. The slots in one or both of the tubular members can be, however, at an angle relative to the longitudinal axis that is other than substantially 90 degrees.

In some embodiments the steerable device also includes a tubular element disposed between the inner and outer tubular members. The intermediate member can be, for example without limitation, a flexible polymeric material. The intermediate member can be encasing one or both of the tubular members, or comprising one or both of the members. The intermediate member can be adapted to provide a fluid barrier and/or a low friction surface.

Slots as described herein can be formed in a tubular member by laser machining or other machining processes. Forming the slots creates at least one spine in a tubular member. A spine as used herein can be considered a region of the steerable portion that imparts axial stiffness in compression or tension, or both, and may additionally include features that provide torsional stiffness. When a single spine is created in a tubular member, the neutral bending axis of the tubular member is moved to the spine of the tubular member.

In some embodiments, a tubular member includes at least two spines, the combination of which moves the neutral bending axis of the tubular member to an axis parallel to, or tangent to when bent, the longitudinal axis of the tubular device and passing through the spines.

In some embodiments a liner, such as a flexible polymer liner, is bonded on the inner surface of the inner tubular member. In some embodiments a flexible polymer is bonded or otherwise disposed over the outer surface of the outer tubular member. A liner can also be disposed such that it is encasing the inner tubular member.

In some embodiments the steerable portion is comprised of a first tubular member that is adapted to bend preferentially in a first direction and a second tubular member that is not adapted to bend preferentially in one direction. In some instances of these embodiments, the second tubular member is a flexible polymer material with or without a braided or wire support. In some instances, a wire or other structural support is included in the first tubular member in the deflectable area to increase compressive and tensile stiffness along one side of the tubular member, thus moving the neutral bending axis from the longitudinal axis of the tubular member to the side of the tubular member that includes the structural support. In some instances wires are laid longitudinally and distributed evenly to increase axial stiffness in tension without creating a preferential bending.

In some embodiments the device includes three tubular members, having three offset neutral bending axes approximately 120 degrees radially spaced apart, thus providing the steerable device with universal steering in any direction.

Figure 3:
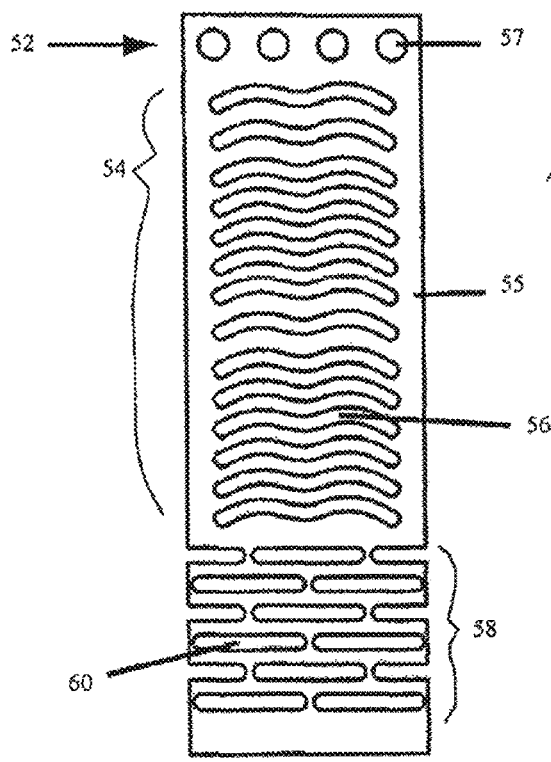
FIG. 3 illustrates a flattened view showing an exemplary slot pattern for use in a steerable portion of a device.

FIG. 3 illustrates, for ease of description, a flattened, or unrolled, portion of exemplary tubular member 50, which can be an inner or an outer tubular member. Tubular member 50 includes fixation region 52, steerable portion 54, and a proximal neutral portion 58. Steerable portion 54 includes a plurality of slots 56 formed therein to define spine 55 extending along the steerable portion. Slots 56 are sinuous-shaped slots, and spine 55 has a generally straight configuration along the length of steerable portion 54. That is, spine 55 is substantially parallel with the longitudinal axis of the tubular member. Fixation region 52 includes a plurality of holes 57 to facilitate bonding to provide for axial fixation relative to a second tubular member (not shown). Proximal portion 58 includes a plurality of multiple overlapping slots 60 to provide the desired flexibility, axial force transmission, and torque transmission characteristics.

Figure 4:
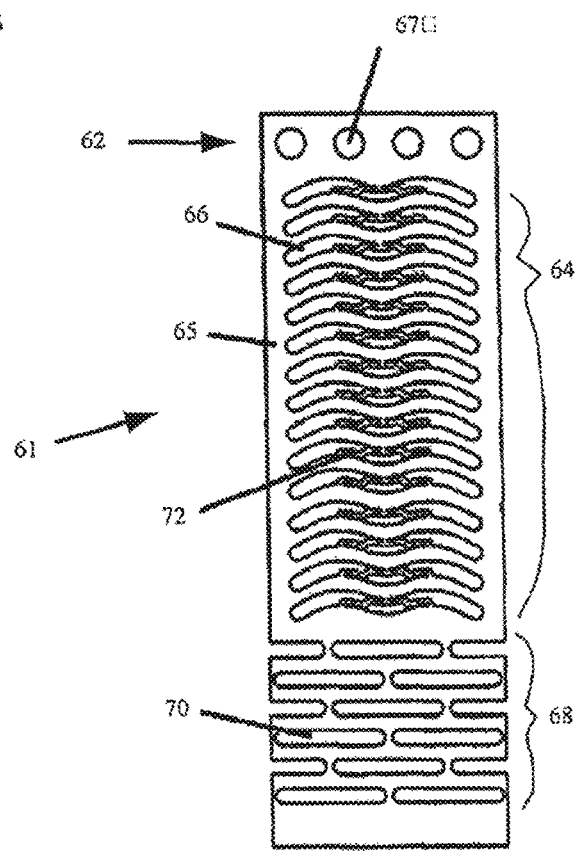
FIG. 4 illustrates a flattened view showing an exemplary slot pattern for use in a steerable portion of a device.

FIG. 4 illustrates a flattened, or unrolled, portion of exemplary tubular member 61, which can be an inner or an outer tubular member of a steerable portion. Tubular member 61 includes fixation region 62, steerable portion 64, and proximal neutral bending portion 68. Neutral bending portion 68 will exhibit minimal bending preference upon a compressive or tensile force applied thereto. Tubular member 61 is similar to tubular member 50 shown in FIG. 3, but includes linking elements 72, which can be flexible. Each linking element extends from one side of a slot to the other side. Each linking element includes two arm portions extending from one side of the slot to the other side of the slot. The two arms meet at the point at which they are connected to one side of the slot. The linking elements extend along steerable portion 64 on substantially the opposite side as spine 65. Linking elements 72 enhance and/or control torque response and bending of steerable portion 64. As steerable portion 64 is bent about spine 65, linking elements 72 bend and stretch under tension. As steerable portion 64 is twisted, or put in torque, linking elements 72 are put in compression. In torque, the gap between a given linking element and the section of the tubular member proximally adjacent to the given linking element collapses, effectively increasing the torsional stiffness of steerable portion 64.

Figure 5:
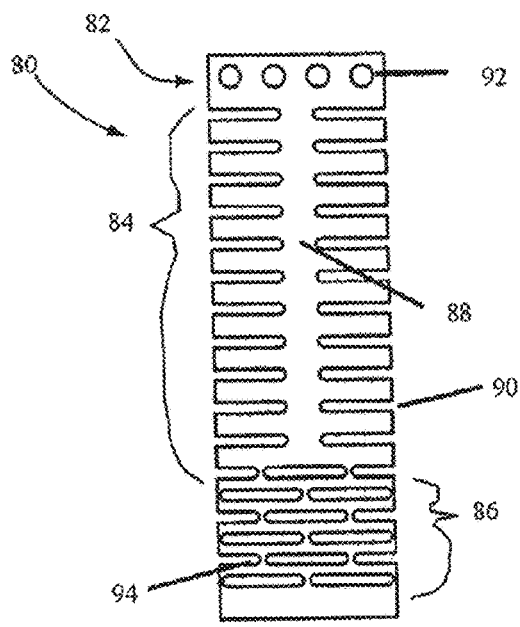
FIG. 5 illustrates a flattened view showing an exemplary slot pattern for use in a steerable portion of a device.

FIG. 5 illustrates a flattened portion of exemplary tubular member 80, including fixation portion 82, steerable portion 84, and proximal neutral portion 86. The embodiment in FIG. 5 is similar to the outer tubular member as shown in FIGS. 2A and 2B. Steerable portion 84 includes substantially straight slots 90 that are substantially perpendicular to the longitudinal axis of tubular member 80. Spine 88 is substantially straight in configuration, extending along the length of steerable portion 84 substantially parallel to the longitudinal axis of the tubular member 80. Fixation portion 82 includes holes 92 therethrough (four shown) to facilitate bonding. Proximal portion 86 has multiple overlapping slots 94 to give the desired flexibility, axial force and torque transmission.

Figure 6:
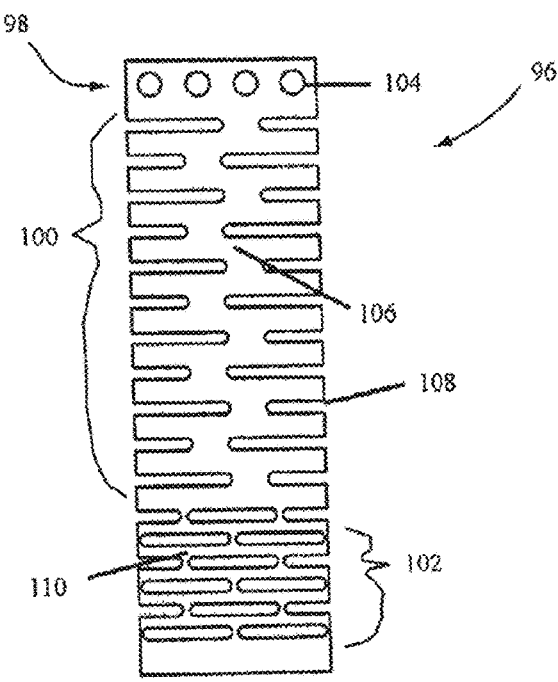
FIG. 6 illustrates a flattened view showing an exemplary slot pattern for use in a steerable portion of a device.

FIG. 6 illustrates a flattened portion of exemplary tubular member 96, including fixation portion 98, steerable portion 100, and proximal neutral portion 102. Steerable portion 100 includes substantially straight slots 108 that are substantially perpendicular to the longitudinal axis of tubular member 96, but each is offset relative to the adjacent slot so that spine 106 has a sinuous shape extending along the length of steerable portion 100. Fixation portion 98 includes holes 104 therethrough (four shown) to facilitate bonding. Proximal portion 102 includes multiple overlapping slots 110 to give the desired flexibility, axial force and torque transmission characteristics.

Figure 7A:
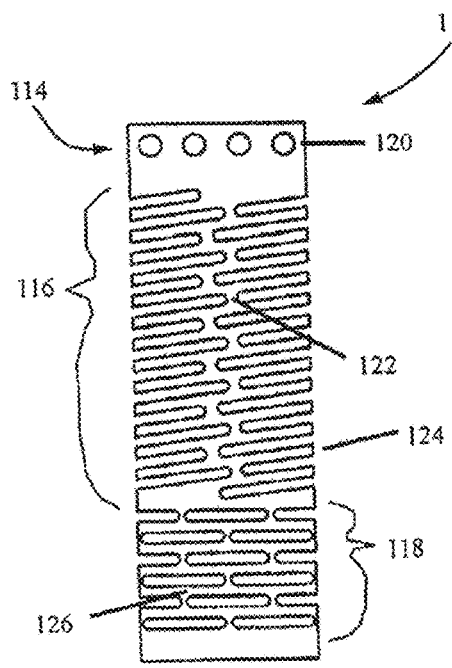
FIGS. 7A and 7B illustrate flattened views showing exemplary slot patterns for use in a steerable portion of a device.
Figure 7B:
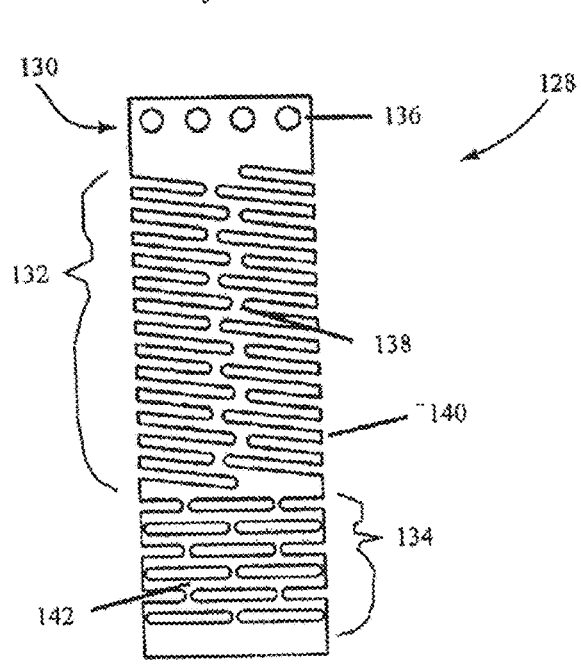

FIGS. 7A and 7B illustrate exemplary portions of flattened first and second tubular members 112 and 128. First tubular member 112 can be an inner tubular member and second tubular member 128 can be an outer tubular member, or first tubular member 112 can be an outer tubular member and second tubular member 128 can be an inner tubular member. Tubular members 112 and 128 can be assembled as part of a steerable delivery device. That is, one of the first and second tubular members can be disposed within the other. First tubular member 112 includes fixation portion 114, steerable portion 116, and proximal neutral portion 118. Fixation portion 114 includes holes 120. Steerable portion 116 has slots 124 formed therein to define spine 122. Spine 122 has a generally sinuous shape. Proximal portion 118 includes a plurality of overlapping slots 126. Second tubular member 128 includes fixation portion 130, steerable portion 132, and proximal neutral portion 134. Fixation portion 130 includes holes 136. Steerable portion 132 has slots 140 formed therein to define spine 138. Spine 138 has a generally sinuous shape. Proximal portion 134 includes a plurality of overlapping slots 142.

In FIGS. 7A and 7B, the slots in each of tubular members 112 and 128 are offset relative to the adjacent slot, interrupted, and have a general helical configuration. Spines 122 and 138 have generally sinuous configurations. The slots in the tubular members are at the same angle relative to the longitudinal axis of the tubular member, but are formed in opposite helical patterns. An advantage of having inner and outer tubular members with slots that are not in alignment (as opposed to inner and outer tubular members that have slots perpendicular to the longitudinal axis of the tubular member) is that the slots are less likely to get caught up on one another as the steerable portion is steered. The angled slots shown in FIGS. 7A and 7B also provide for an increased torque response based on a torque applied at the proximal end of the device.

Figure 8:
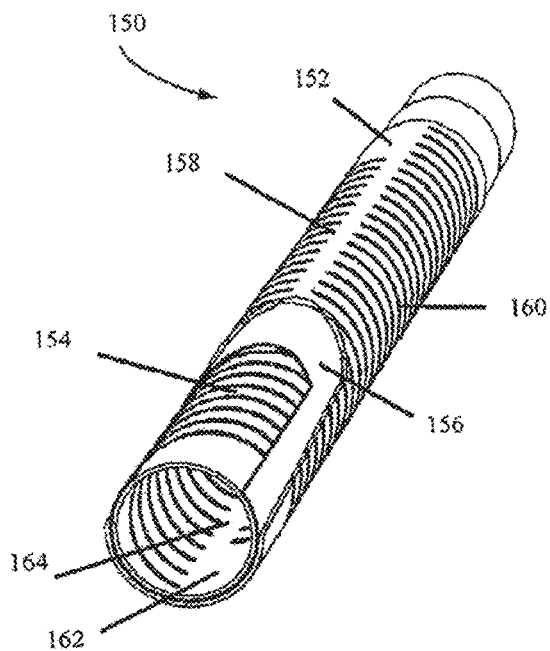
FIG. 8 illustrates an exemplary steerable portion including an outer slotted tubular member and an inner slotted tubular member, with an intermediate tubular element therebetween.

FIG. 8 illustrates a portion of an exemplary steerable delivery device. Steerable device 150 includes outer tubular member 152, inner tubular member 154, and intermediate tubular member 156. A portion of outer tubular member 152 and intermediate member 156 are cut away to show inner tubular member 154. Intermediate tubular member 156 can be a flexible polymeric tube. Inner and outer tubes 152 and 154 have slots 160, 164 formed therein to define spines 158 and 162. The spines are substantially 180 degrees apart, as shown. The slots formed in the respective tubular members are at an angle relative to the longitudinal axis of the steerable portion and are formed in opposite helical patterns.

Figure 9:
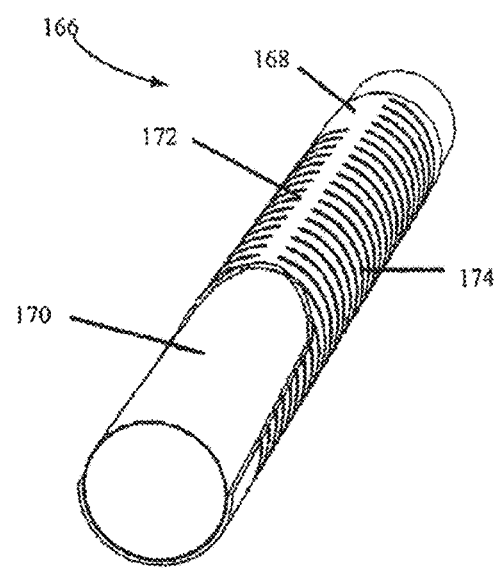
FIG. 9 illustrates an exemplary steerable portion including an outer slotted tubular member and an inner non-slotted tubular member.

FIG. 9 illustrates a portion of an exemplary steerable delivery device. Steerable device 166 includes outer tubular member 168 and inner tubular member 170. Inner tubular member 170 can be a flexible polymeric tubular element. Outer tubular member 168 has a plurality of slots 174 formed therein to define spine 172. Inner tubular member 170 has no preferential bending axis. Inner tubular member 170 could alternatively have a modified bending axis offset by having, for example, a stiffening element incorporated into the wall of inner tubular member 170 approximately 180 degrees from spine 172. In some embodiments inner tubular member 170 may incorporate wire braids and or axially-laid wires which reduce kinkability and increase axial stiffness as is common in braided catheters or other similar known tubular medical devices.

Figure 10:
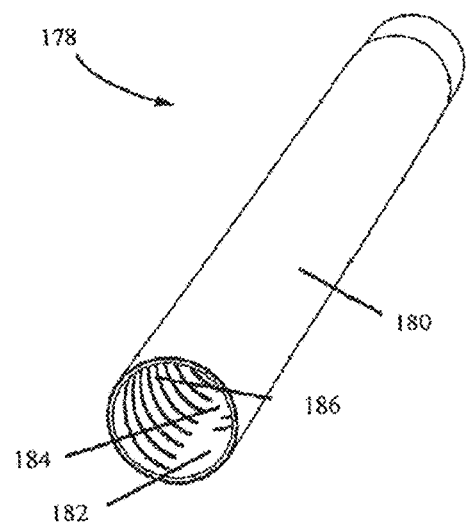
FIG. 10 illustrates an exemplary steerable portion including an inner slotted tubular member and outer non-slotted tubular member.

FIG. 10 illustrates a portion of an exemplary steerable delivery device. Steerable delivery device 178 includes outer tubular member 180 and inner tubular member 182. Outer tubular member 180 can be, for example, a flexible polymeric tubular member. Inner tubular member 182 has a plurality of slots 186 formed therein to define spine 184, which is substantially parallel to the longitudinal axis of the steerable portion. Outer tubular member 180 has no preferential bending axis. Alternatively, outer tubular member 180 can have a preferential bending axis. For example, a structural support element can be incorporated into the wall of outer tubular member 180 approximately 180 degrees from spine 184. Outer tubular member 180 can be substantially the same as inner tubular element 170 in FIG. 9, but for any lubricity enhancing feature. In some embodiments inner tubular member 170 may incorporate wire braids and or axially laid wires which reduce kinkability and increase axial stiffness as is common in braided catheter or other similar known tubular medical device.

In an alternative embodiment, the device includes inner and outer slotted tubes, and additionally includes an outermost tubular member similar to 180 shown in FIG. 10. The outermost tubular member can be, for example without limitation, a polymeric tubular member.

Figures 11A, 11B:
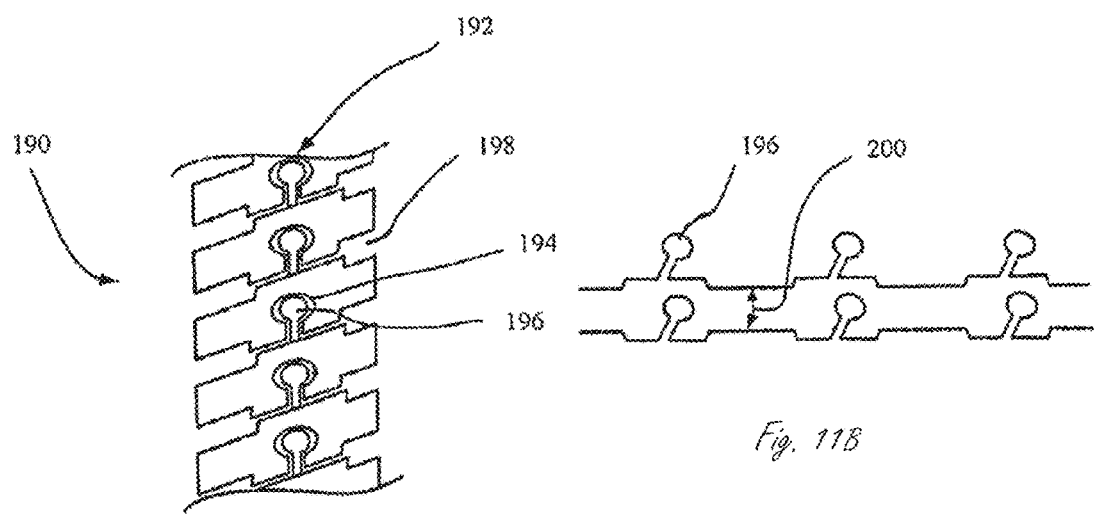
FIG. 11A is a representation of a pattern for use in a steerable portion capable of being cut from a tube or created by winding a ribbon into a tube.
FIG. 11B illustrates a section of a ribbon for use in the tube of FIG. 11A.

FIG. 11A illustrates a portion of an exemplary embodiment of a first tubular member that can be included in a steerable delivery device. Tubular member 190 is a tubular member formed from a ribbon wire. Tubular member 190 has spine 192 formed by coiling a ribbon shaped with interlocking elements 194 and 196, which together form an interlocking feature along spine 192. Interlocking elements 194 and 196 may be press-fit to interlock the two. The interlocking elements can be encased with a tubular member, such as a polymer tubular member, to secure them in place. The interlocking elements can also, or alternatively, have a polymer tubular member disposed therein to help secure them in place. In addition to the interlocking features, the ribbon wire has sections of decreased width 198 which once wound into a tubular structure create the steerable portion for flexibility. A second tubular member of the steerable delivery device can be created in a similar manner to the tubular member in FIG. 11A. FIG. 11B illustrates an embodiment of the ribbon with interlocking elements 196 and decreased width regions 200 between elements 196. The angle of interlocking elements 196 relative to the longitudinal axis of the tubular element can be varied based on the pitch of the coil. Such a pattern can additionally be fabricated by laser machining.

Figures 12A, 12B:
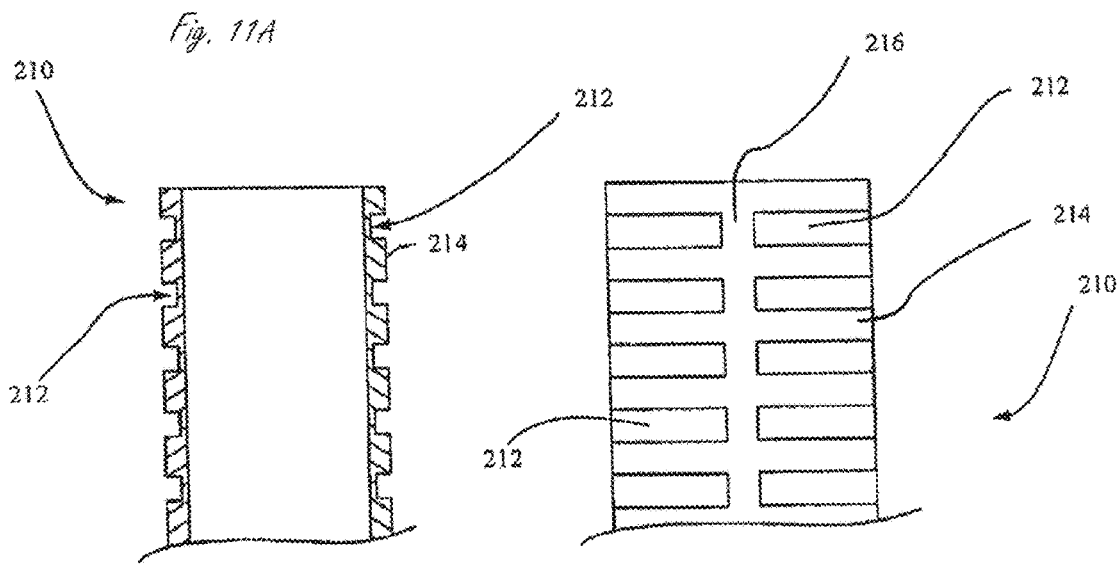
FIGS. 12A and 12B are different views of a groove pattern for use in a steerable portion.

FIGS. 12A and 12B illustrate an exemplary embodiment of a tubular member. Tubular member 210 comprises a tube 214 with grooves 212 formed therein on the outer surface of tube 214. Grooves 212 do not extend all the way through tube 214. Tubular member can be, for example, a stiff polymeric tubular member. FIG. 12A shows a sectional view of a portion of tubular 210 showing the depth of grooves 212 in the steerable portion. FIG. 12B illustrates a flattened view of tubular member 210 showing grooves 212 formed in tube 214. Grooves 212 define a single substantially straight spine 216. Grooves 212 cut into tube 214 increase flexibility of the steerable portion to allow the steerable portion to be steered. Spine 216 provides for the application of compressive and tensile forces to steer the device. Because the cut does not go all the way through the wall of the tube, it inherently creates a fluid tight barrier and a lubricious liner. In some embodiments tubular member 210 can be an inner or outer tubular member of a steerable device, and the other of the inner and outer tubular elements can also include a tubular element with grooves formed thereon. In some embodiments the steerable device can also have a polymeric sleeve to encapsulate the outer tube to create a smooth outer surface.

Figure 13A:
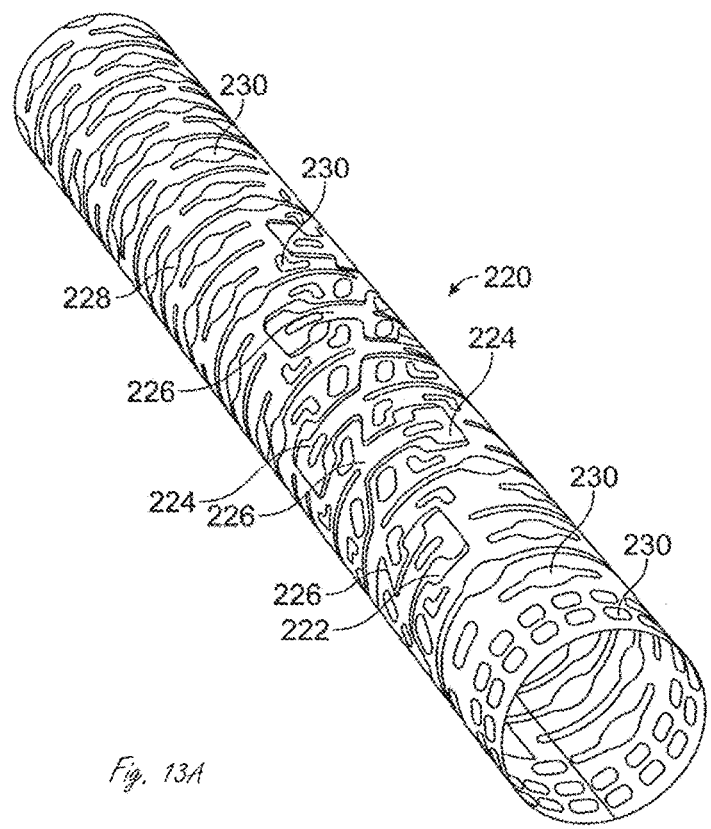
FIGS. 13A, 13B, and 13C are various views of a cut pattern for use in a guide catheter.
Figure 13B:
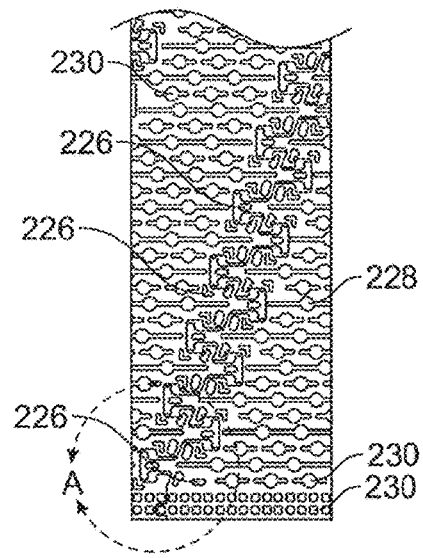
Figure 13C:
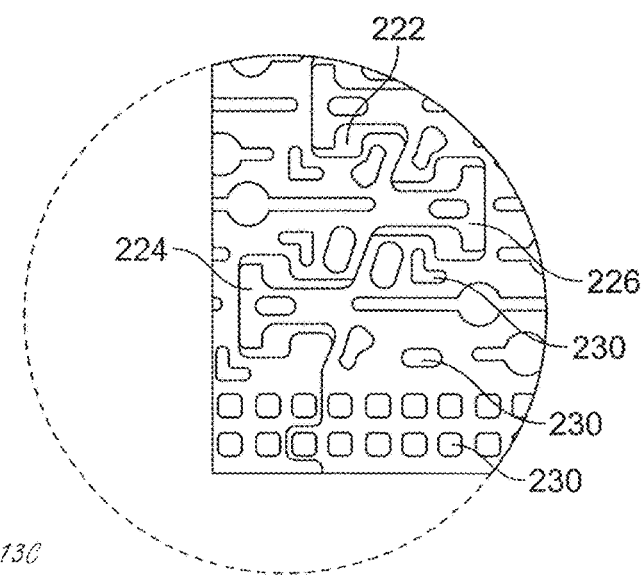

FIG. 13A illustrates a portion of an exemplary introducer sheath reinforcement member 220. Member 220 is formed by laser cutting a tubular member to slots or gaps therein. A helical slot 222 defines interlocking T-shaped patterns 224 formed in reinforcement member 220. The helical path is shown generally in helical path 226. Flexibility slots 228 are formed in member 220 to provide flexibility to member 220. Member 220 also includes bonding slots 230 formed therein to allow for bonding to one or more components of the device. FIG. 13B illustrates member 220 from FIG. 13A in a flattened pattern showing the interlocking T-shaped pattern along helical path 226, flexibility slots 228, and bonding slots 230. FIG. 13C shows a close-up of the section shown in FIG. 13B.

In some embodiments a guide catheter includes a relatively rigid metal or polymer reinforcement member (an example of which is shown in FIGS. 13A-13C) layered between an inner and an outer flexible polymer tube. The rigid reinforcement member can be laser machined or otherwise cut in a pattern in order to enhance flexibility along the longitudinal axis of the tube, to allow some limited radial compliance, and to allow bonding of the inner and outer flexible polymers. The slot pattern can include an interlocking T-shaped pattern arranged helically around the tube for flexibility and radial compliance, a slot pattern where the slots are substantially perpendicular to the tube longitudinal axis, and are patterned along the tube longitudinal axis to further enhance flexibility and bonding of said layers.

Figure 14:
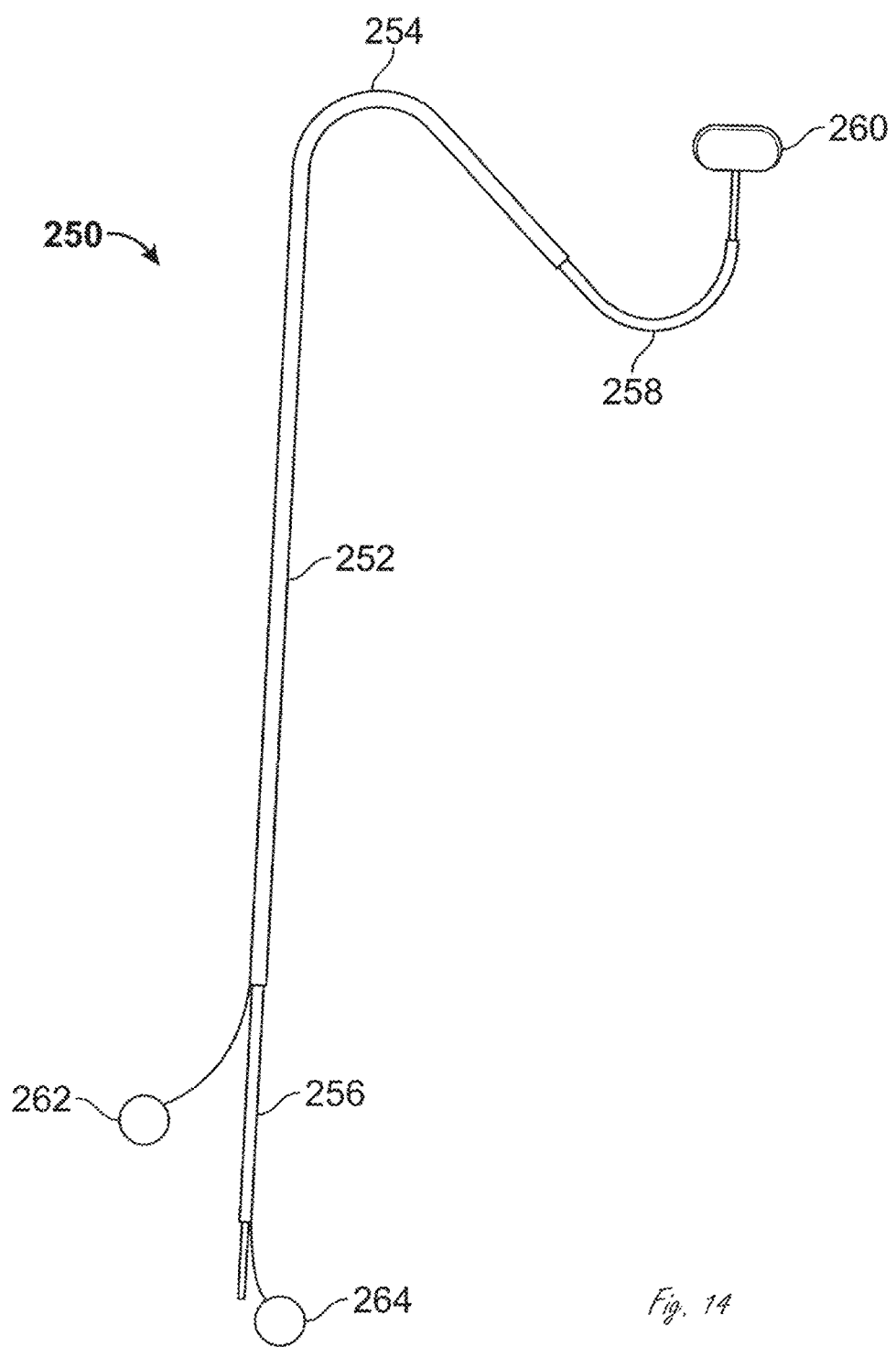
FIG. 14 illustrates an outer guide member and a steerable device therein.

FIG. 14 illustrates an exemplary embodiment of a guide system adapted to guide and deliver a therapeutic, diagnostic, interventional, or any other type of medical device 260 intraluminally to a target location within a body. Guide system 250 includes outer guide member 252 and steerable delivery device 256, a portion of which is disposed within outer guide member 250. Steerable delivery device 256 can be, for example, any of the steerable delivery devices described herein. Outer guide member 252 has a preset bend 254 that can be formed by, for example, heat setting. Steerable delivery device 256 includes steerable portion 258, which can be formed as, for example, any of the steerable portions described herein. For example, steerable delivery device can include outer and inner tubular members, wherein at least one of the tubular members is adapted to preferentially bend in a first direction. In the embodiment shown in FIG. 14, steerable portion 258 is comprised of a single steerable tubular member steered into the configuration shown in FIG. 14 by actuating pull wire 264. Alternatively, steerable delivery device 256 can be comprised of the embodiment described in FIG. 2, and steered by relative axial movement of inner and outer tubular members, as described herein.

Alternatively, outer guide member 252 can be adapted to be bent using optional pull wire 262, shown in FIG. 14. In such an embodiment bend 254 may or may not preset. Guide member 250 comprises a tubular member incorporating a pattern of slots as described for steering portions herein. When located in position pull wire 262 is tensioned and the axial and torsional stiffness of bend 254 is thereby increased. A steerable outer guide member 252 in its delivery configuration (non-bent) is generally loose and compliant, but is tensioned or compressed to reconfigure it into a pre-set shape. Its stiffness in the bent configuration is a function of the amount of tension or compression applied and the particular slot pattern chosen.

Bend 254 in outer guide member 252 is compliant enough to be straightened for delivery, for example advanced on a guide wire, but rigid enough to be able to guide steerable delivery device 256 around bend 254. Steerable delivery device 256 is steerable and transmits torque.

The structural properties of the inner and outer tubular members of the steerable delivery device will determine the manner in which they respond to force applied thereon. The structural properties of the inner and/or outer tubes will depend on the tubing material and the design, or characteristics, of the slots created in the tubular members (unless one of the inner and outer tubular members does not have any slots therein). The design of the slot pattern is therefore a function of the required structural properties of the tubular member. For example, structural properties of the tubular member that can be modified by changing the design of the slots or slot patterns include flexural stiffness, torque transmission, steerability, radius of curvature, and allowable wall thickness of the steerable assembly.

Figure 15:
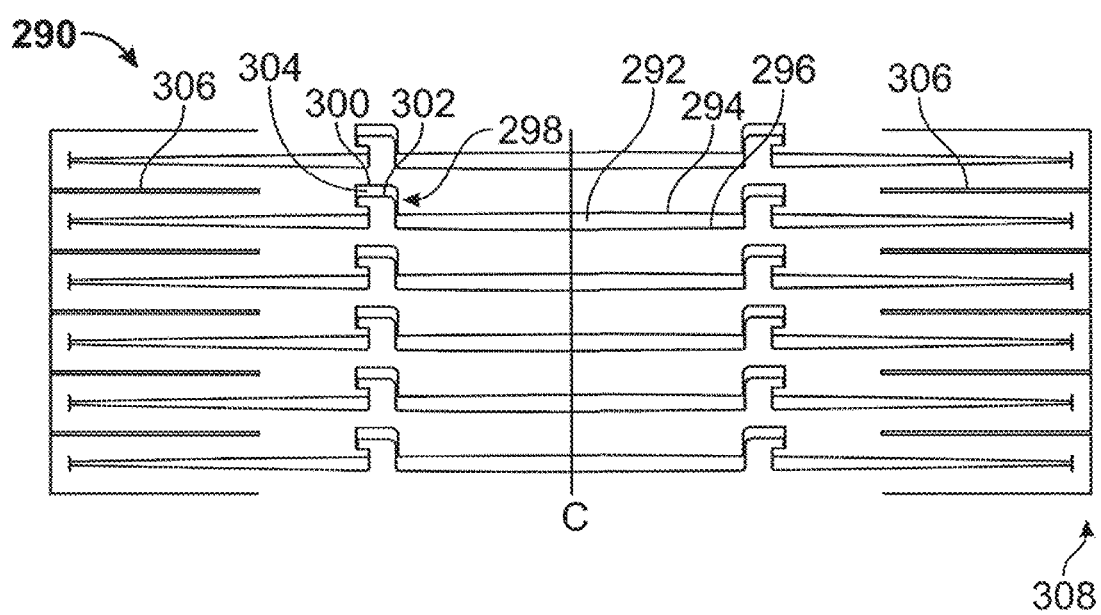
FIG. 15 illustrates a discontinuous cut pattern for use on a tubular member that is most steerable in compression.

FIG. 15 is a flattened view and illustrates a portion of an exemplary steerable portion of a tubular member. Tubular member 290 can be an inner or an outer tubular member as described herein. Steerable portion 290 is typically a laser-cut tubular member, but may in fact be fabricated by any technique capable of creating the appropriate widths of cuts required (e.g., water jet, wire EDM, etc.) wherein first cut, or slot, 292 is made, defined by first surface 294 and second surface 296. Slot 292 extends almost all the way around tubular member 290, and defines spine 308. Slots 282 are thickest, along the tubular longitudinal axis, along compression axis C which allows tubular member to be compressed along compression axis C, which changes the configuration of tubular member 290. Tubular member 290 also includes interlocking features 298 (only one of which is labeled), which include first interlocking element 300 and second interlocking element 302. Slot 292 includes slot portion 304, which is defined by the first and second interlocking elements 300 and 302 and allows for movement between the two interlocking elements 300 and 302 in the axial direction. Tubular member 290 also includes stress relief slots 306, which extend across spine 308 and provide stress relief for spine 308. Stress relief slots 306 can be considered to be axially in-between slots 292. Slots 292 are not connected with slots 306. Slots 306 are substantially thinner than slots 292. As will be described in detail below, tubular member 290 is adapted to be compressed along compression axis C, which is substantially 180 degree from spine 308.

Figures 16A, 16B:
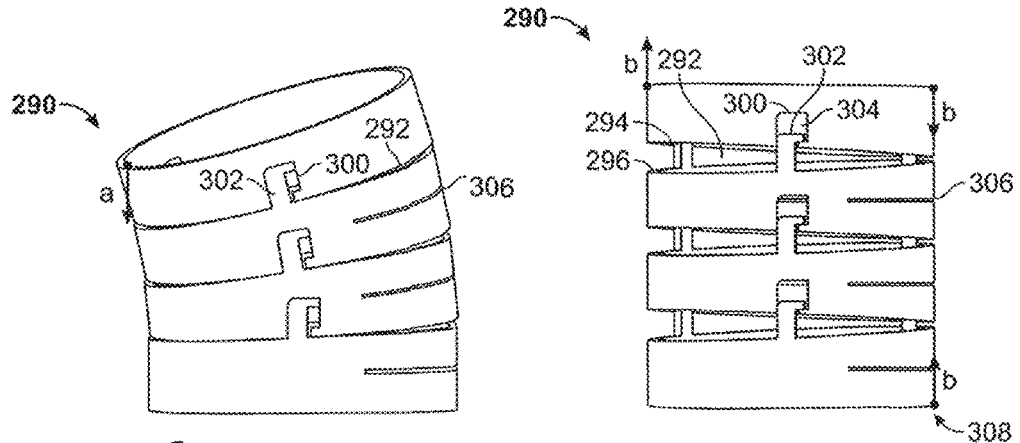

FIGS. 16A and 16B illustrate a portion of tubular member 290 shown in FIG. 15. FIG. 16B illustrates tubular member 290 with slot 292, with a greatest thickness along compression axis C. Slot 292 includes slot 304, which is defined by interlocking elements 300 and 303. Slot 292 and slot 304 allow for compression of tubular member 290, shown in FIG. 16A. When a compressive force A is applied along compressive axis C surfaces 294 and 296 are brought closer towards another, as are surfaces 300 and 302. Slots 292 and 304 therefore allow for axial compression of tubular member 290, until surfaces 294 and 296 engage one another, or until surfaces 300 and 302 engage one another, whichever happens first. Slots 292 and 304 can be designed such that the slots close at the same time. Once the surfaces engage, they behave substantially like a solid tube and can no longer be compressed along the engagement points. In this configuration, the first and second interlocking elements are adapted to prevent movement therebetween at least along a first axis, in this embodiment along compression axis C.

Upon a compressive force to tubular member 290, tubular member will therefore be steered into the configuration shown in FIG. 16A.

Figure 16C:
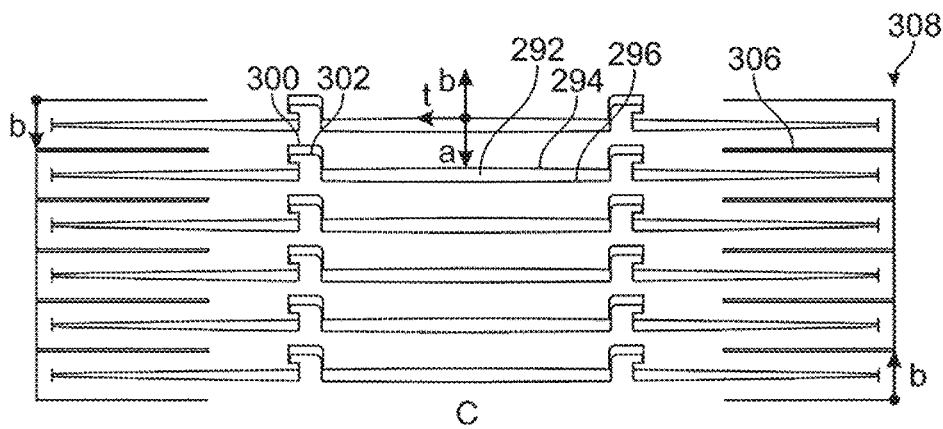
FIG. 16C illustrates compressive and tensile forces acting thereon.

Similarly, when a tensile force is applied to tubular member 290 shown in FIG. 16A, tubular member 290 will straighten to the configuration shown in FIG. 16B. Particularly, tubular member 290 will straighten until the interlocking features engage one another and prevent further movement. FIG. 16C illustrates the tubular member from FIGS. 16A and 16B and indicates points of load application including those illustrated in FIGS. 16B and 16C. Torsional force T indicates a torsional force acting on tubular member 290 upon the application of torque at a proximal end of the device. Tensile and compressive forces are listed as "a" or "b" depending on the behavior exhibited by the tubular member as described below.

Figure 17:
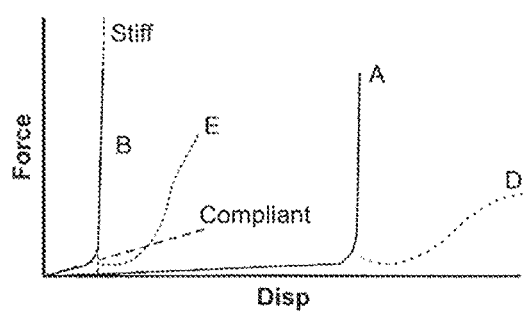
FIG. 17 is a graph illustrating Force v. Displacement behavior associated with the application of loads or displacements at various points around the tubular member shown in FIGS. 15-16C.

FIG. 17 is a graph illustrating Force v. Displacement behavior associated with the application of loads or displacements at various points around tubular member 290 shown in FIGS. 15-16C. The Force/Displacement behavior of tubular member 290 for loads applied in planes passing through the longitudinal axis of the tubular member, ranges between the lines A and B in FIG. 17. Curve A illustrates the behavior along a compliant axis on the surface of the tubular member and parallel to the longitudinal axis of the tubular member where the slots are widest, while curve B illustrates the behavior where the slots are very narrow. As the tubular member is bent about spine 308 in a fashion which closes slots 292, the forces required to bend the tubular member are low and the Force/Displacement curve has a small slope. The tubular member is compliant in this region. When the width of the slots decreases to zero the structure becomes much stiffer as indicated by the second much higher slope region of curve A. The amount of displacement associated with closing the slots is essentially indicated by point D where the slope of the Force/Displacement curve changes. Curve A indicates the behavior expected from forces applied at a point along compressive axis C, illustrating that a large amount of axial displacement follows from minimal compressive force on tubular member 290. Upon closing slots, the compressive axis becomes stiff (indicated by the large increase in Force at point D in the curve). Curve B in the graph indicates compression along the axis running through spine 308. Due to stress relief slots 306, a small amount of compressive displacement occurs before spine 308 stiffens and begins to act substantially like a solid tube, as indicated by point E in the graph. The structure will exhibit the behavior of curve B for tensional loads applied to the top of the structure on the compressive axis C as the gaps closed under this loading are very narrow. Curve B also represents the behavior of the structure to torsional loads, as the gaps impacted most by these loads are narrow.

Figure 18:
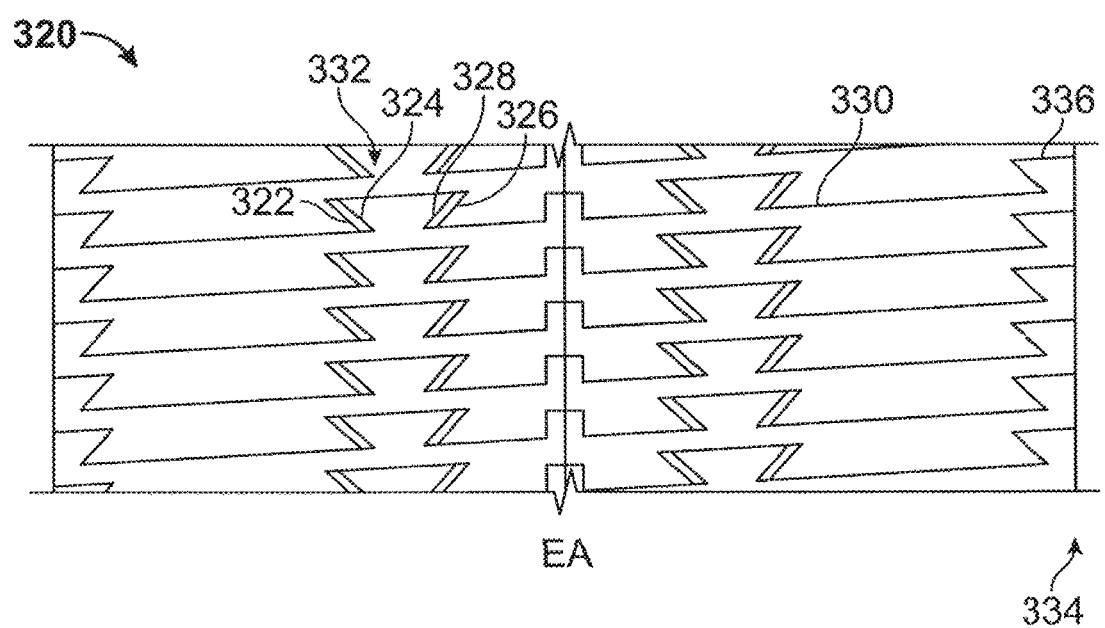
FIG. 18 illustrates a continuous cut pattern for use on a tubular member that is most steerable in tension.

FIG. 18 illustrates a flattened view of exemplary tubular member 320. Slot 330, or cut, formed therein has a spiral (also referred to herein as helical) pattern and is uninterrupted. Tubular member 320 is shown in an as-cut compressed configuration, and is adapted to be expanded the greatest amount along expansion axis EA upon the application of a tensile force thereto. Tubular member 320 includes interlocking features 332, which include surfaces 322 and 324, and surfaces 326 and 328. Slot 330 includes the slot defined by surfaces 326 and 328, and by surfaces 322 and 324. In this embodiment the slot, or gap, defined by surfaces 326 and 328 is larger than the gap defined by surfaces 322 and 324. That is, the gap that is closer to expansion axis EA is larger than the gap that is further from expansion axis EA. Tubular member 334 also includes spine 334, which is interrupted by small slots 336. As illustrated in FIG. 16C, tubular member 320, upon the application of axial loads applied thereto, will exhibit Force/Displacement curves as follows: a compressive force (downwards) applied at EA will exhibit curve B, while a tensile load at EA (upwards) will exhibit curve A. A torsional load will exhibit curve B.

Figure 19:
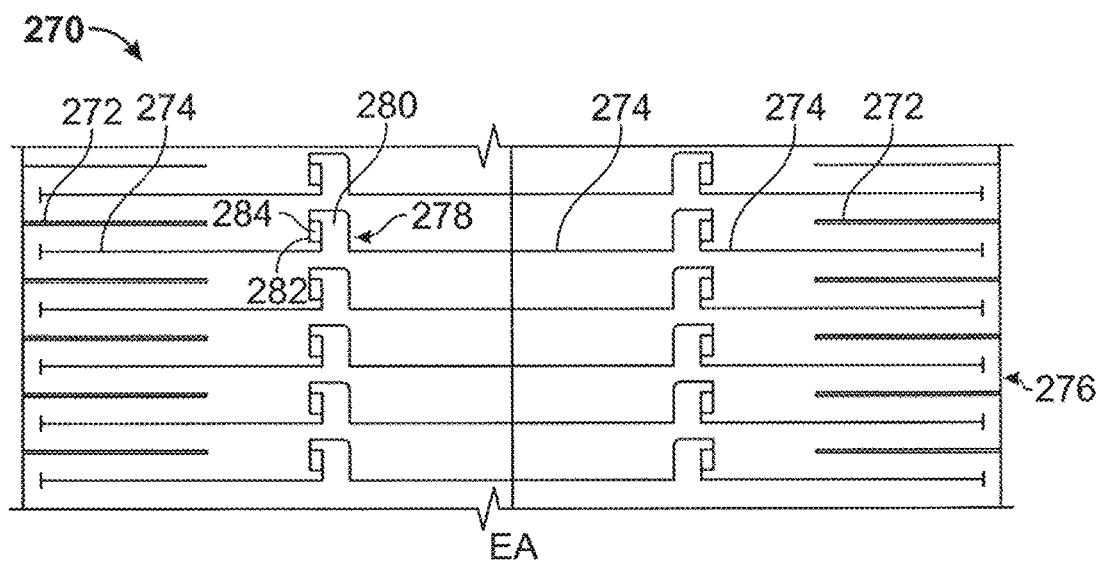
FIG. 19 illustrates a discontinuous cut pattern for use on a tubular member most steerable in tension.

FIG. 19 is a flattened view and illustrates a portion of a tubular member. Tubular member 270 can be an inner or an outer tubular member as described herein. Steerable portion 270 is a laser-cut tubular member wherein first cut, or slot, 274 is made to define spine 276. Cut 274 is made almost all the way around tubular member 270. Cut 274 also defines interlocking features 278 (only one of them is labeled), which are comprised of a first interlocking element 280 and a second interlocking element 282. Cut 274 includes cut 284, which creates the interlocking features and allows for movement between the two interlocking elements. Tubular member 270 also includes stress relief 272, which extend across spine 276 and provide stress relief for spine 276. Stress relief slots 272 can be considered to be axially in-between slots 274. Slots 274 are not connected with slots 272. Tubular member 270 is adapted to be expanded along expansion axis EA, and is adapted to be minimally compressible upon the application of compressive forces thereto. Spine 276 is substantially static. Upon the application of tensile forces to tubular member 270 along expansion axis EA, tubular member 270 will deflect from a straightened configuration into a bent configuration.

Figure 20:
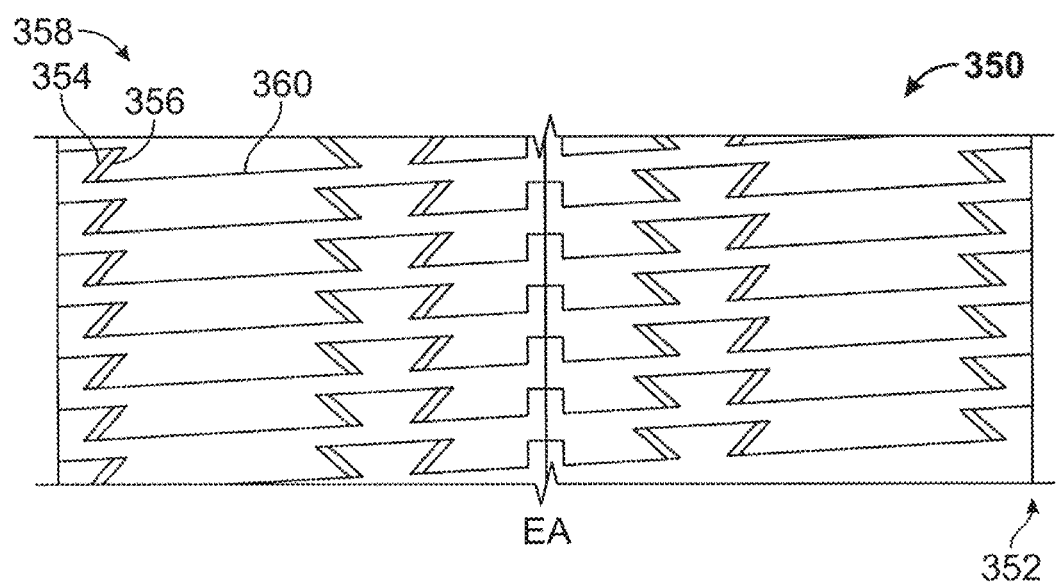
FIG. 20 illustrates a continuous cut pattern for use on a tubular member most deflectable in tension.

FIG. 20 illustrates an embodiment similar to that shown in FIG. 18 and only differences in the structure between the two will be described. All other features can be considered the same. Tubular member 350 includes interlocking features including interlocking elements 354 and 356. Slot 360 created in tubular member 350 includes the gap defined by surfaces of interlocking elements 354 and 356.

Figure 21:
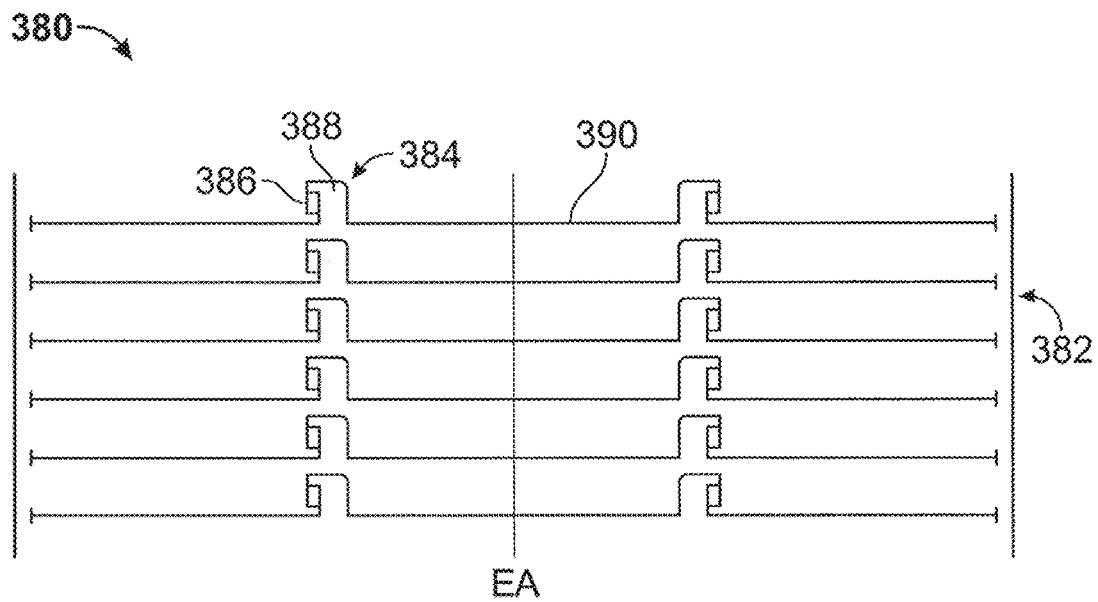
FIG. 21 illustrates a discontinuous cut pattern for use on a tubular member with a substantially straight, continuous spine.

FIG. 21 illustrates a flattened portion of an exemplary tubular member 380 including interrupted cuts 390 that define spine 382. Tubular member 380 includes interlocking features 384, which include interlocking elements 386 and 388. Interlocking features 384 allow for expansion along expansion axis EA upon the application of a tensile force thereto. Tubular member 380, like all tubular members described herein unless specifically stated otherwise, can be incorporated into a steerable portion as an inner or an outer tubular member.

Figure 22:
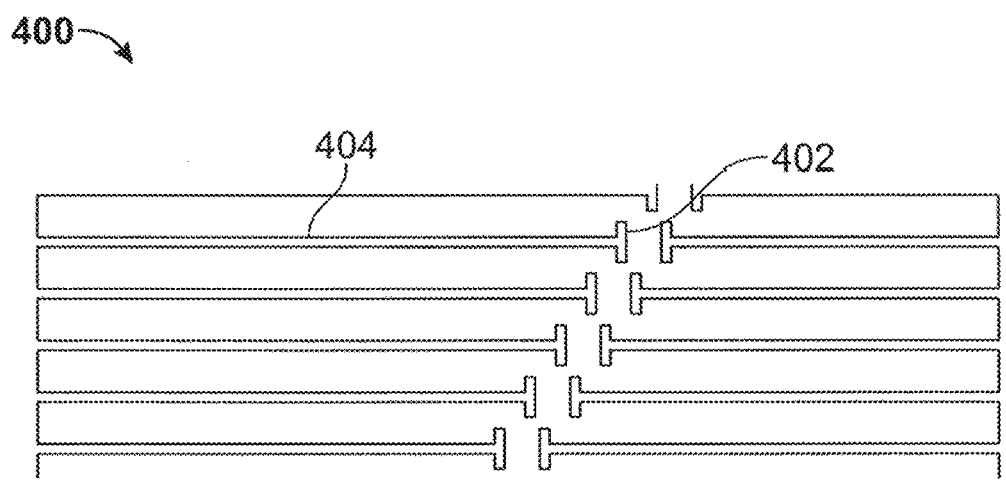
FIG. 22 illustrates a discontinuous cut pattern for use on a tubular member with a helical, continuous spine.

FIG. 22 illustrates a flattened portion of an exemplary tubular member 400. Interrupted slots 404 define spine 402, which has a spiral shape. Tubular member 400 does not have static axis.

Figure 23:
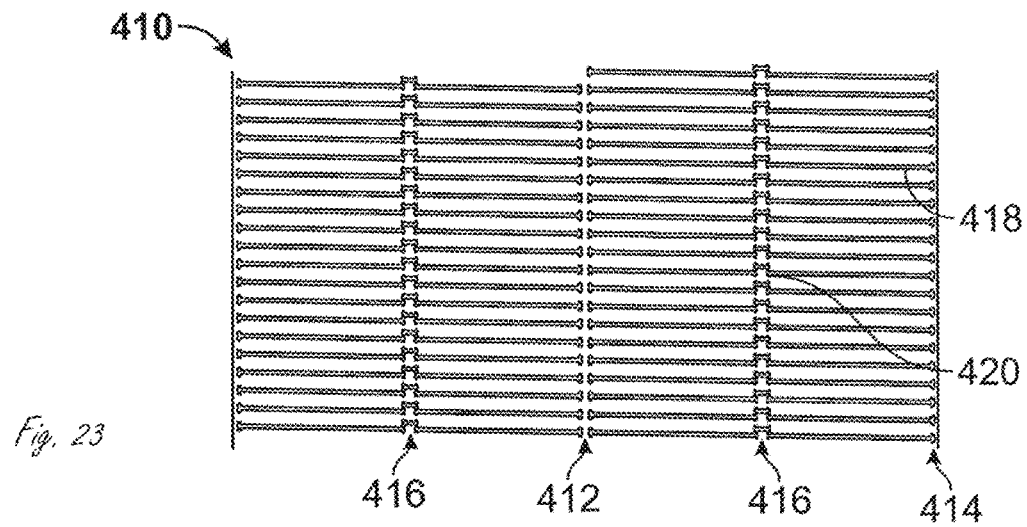
FIG. 23 is a flattened view of an exemplary tubular member with more than one spines.

FIG. 23 illustrates a flattened portion of an exemplary tubular member 410. Tubular member 410 includes interrupted helical slots 418, which define spines 412 and 414. Tubular member 410 has two spines, 180 degrees around the periphery of the device from one other. The helical cut pattern repeats itself every 180 degrees to define substantially straight spines. Tubular member 410 also includes a plurality of interlocking features 420 which provide torsional stiffness. The maximal expansion/compression is at axis 416.

Figure 24:
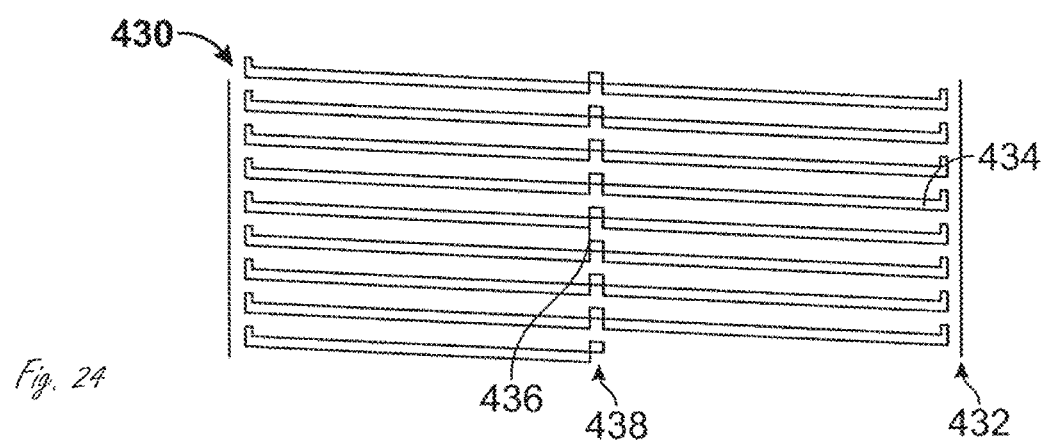
FIG. 24 is a flattened view of an exemplary member with a single substantially straight spine.

FIG. 24 illustrates a flattened portion of an exemplary tubular member 430, which is similar to the embodiment in FIG. 23 but rather than repeating every 180 degrees, the cut pattern repeats every 360 degrees. Slots 434 have an interrupted helical design, and tubular member 430 has a single spine 432. Feature 436 provides additional torsional stiffness. Tubular member 430 exhibits maximal expansion/compression along axis 438.

FIG. 25 illustrates a flattened portion of an exemplary tubular member 440. Tubular member 440 includes slots 448, which repeat every 190 degrees to define spines 442 and 446. The slots have an interrupted helical pattern, and create a relatively neutral pattern.

Figure 26:
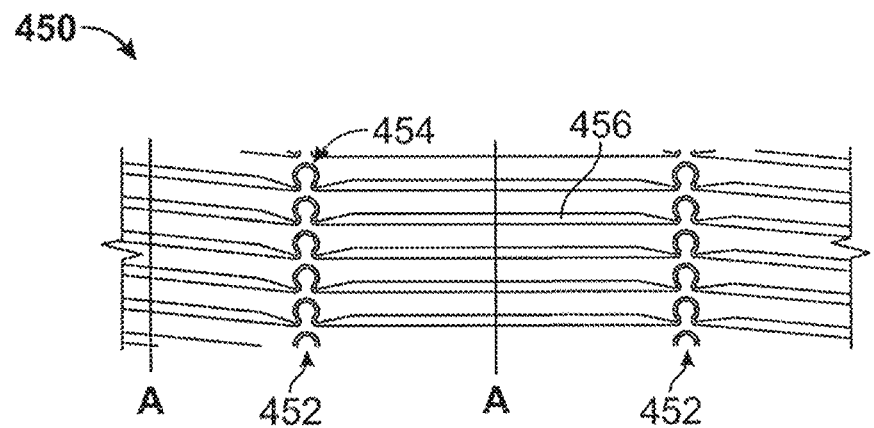
FIG. 26 illustrates a flattened portion of an exemplary tubular member including interlocking features with complimentary curved surfaces that are adapted to support rotation of the tubular member.

FIG. 26 illustrates a flattened portion of an exemplary tubular member 450. Tubular member 450 has uninterrupted slot 456 formed therein, which repeats every 360 degrees. Tubular member 450 also includes interlocking features 454 comprised of at least two interlocking elements as described herein. In this embodiment, the interlocking elements have complimentary curved surfaces and are adapted to support rotation. Slot 456 defines spines 452, while slot 456 allows compression and/or expansion along axes A.

Figure 27:
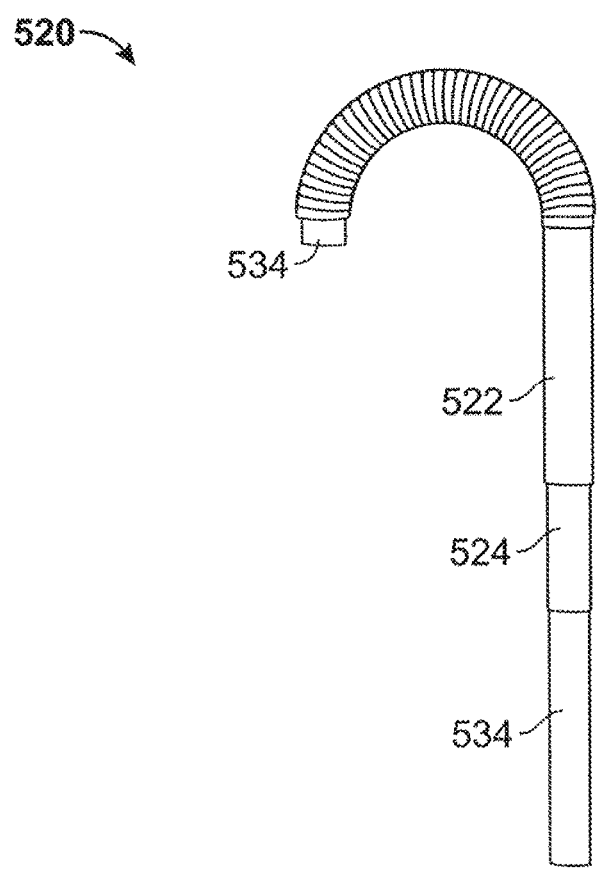
FIG. 27 illustrates an exemplary steerable delivery device including a floating tubular member disposed therein.

FIG. 27 illustrates an exemplary steerable delivery device including steerable portion 520. Steerable delivery device includes outer tubular member 522, inner tubular member 524, and floating inner member 534. Inner tubular member 524 is disposed within and coaxial to outer tubular member 522, and floating inner member 534 is disposed within and coaxial with inner tubular member 524. Floating inner member 534 is axially fixed relative to inner tubular member 524 at a location proximal to steerable portion 520. The device shown in FIG. 27 can also include a liner member disposed between the outer and inner tubular members.

Figure 28:
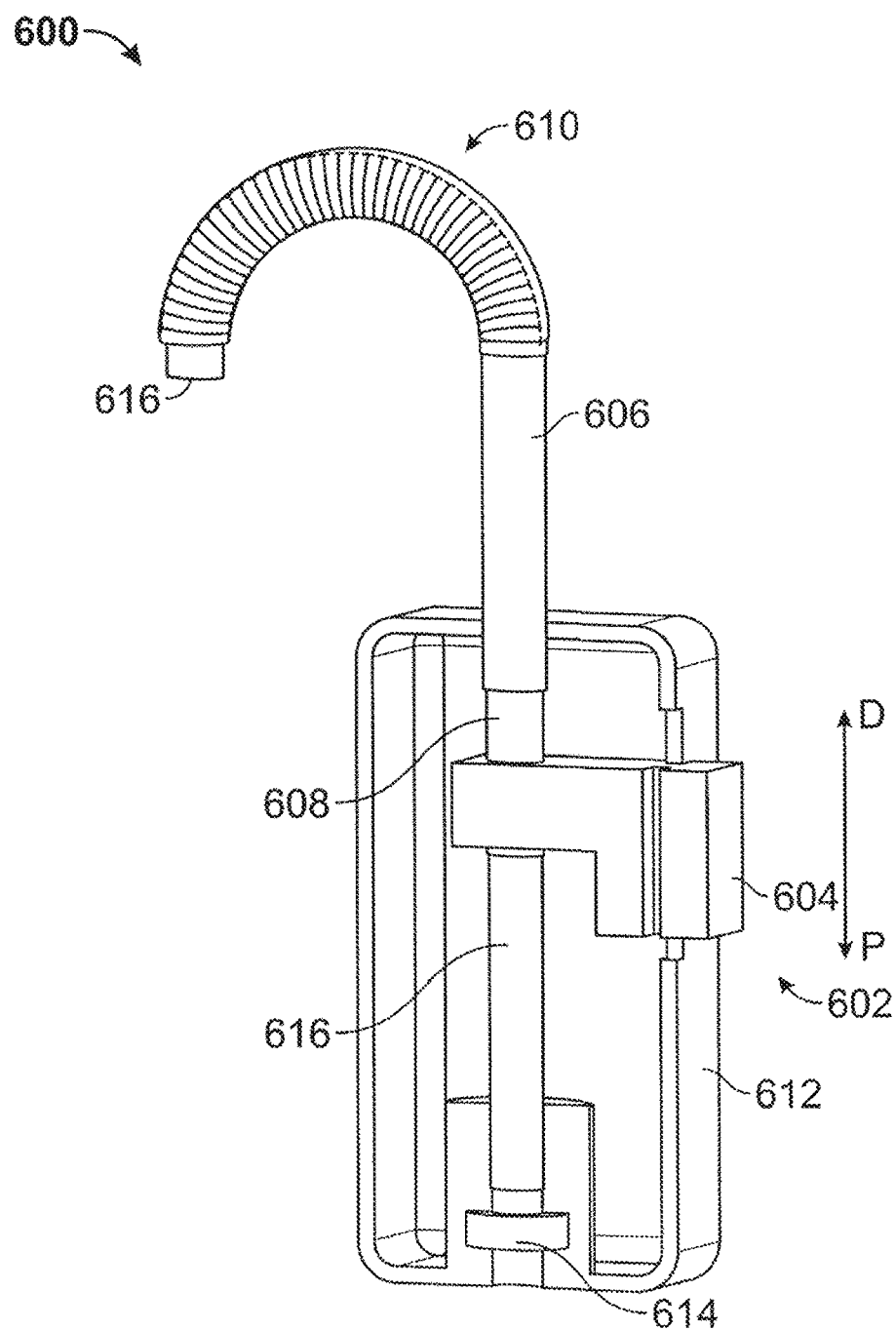
FIG. 28 illustrates an exemplary steerable medical system.

FIG. 28 illustrates an exemplary steerable delivery system 600. System 600 includes control device 602 that is adapted to steer steerable portion 610 of a steerable delivery device. The steerable delivery device includes outer tubular member 606 and inner tubular member 608 disposed within outer tubular member 606. Control device 602 includes housing 612 with a slot therein adapted to allow for movement of actuator 604. Actuator 604 is coupled to inner tubular member 608, and is adapted to be moved axially, either distally D or proximally P to control the axial movement of inner tubular member 608. Any other suitable type of actuator can also be used including actuators incorporating mechanical advantage. Actuation of actuator 604 causes inner tubular member 608 to move axially relative to outer tubular member, which causes steerable portion 610 to bend. The control device is therefore adapted to steer steerable portion 610 inside of a subject. System 600 also includes a floating liner member 616 and hemostatic valve 614.

One aspect of the disclosure is a guide device that is adapted to be maintained, or locked, in a specific configuration to provide access for a medical device or instrument to be passed therethrough, but may or may not be steerable. In FIGS. 2A-2C, steerable portion 32 is adapted to be steered or deflected into any configuration between those shown in FIGS. 2A and 2B. Steerable portion is adapted to be steered to, for example, navigate bends or turns within a bodily lumen. In that specific embodiment, compressive and/or tensile forces are applied to the inner and/or outer tubular members to steer the steerable portion. In some embodiments, once steerable portion 32 is steered into a curved configuration, the forces applied thereto (e.g., compressive, tensile, torsional) can be released, and yet a medical device or instrument can be passed through the tubular members. In some embodiments, however, the bent configuration of the steerable portion can be maintained by maintaining the application of the forces thereto. For example, in FIGS. 2A-2C, steerable portion 32 can be maintained, or locked, in the bent configurations shown by maintaining the application of the compressive and/or tensile forces. By maintaining the application of the forces to the steerable portion or locking the relative displacements of the inner and outer tubes, the inner and outer tubes are substantially axially fixed relative to one another along the length of the steerable portion.

In an exemplary method of use, multiple bend portions may be incorporated and adapted to have a locked configuration that closely mimics, or resembles, a portion of the subject's anatomy. The bend portion can be advanced through the subject (e.g., over a guide wire) to a desired location, and can then be actuated into a curved configuration, such as by the application of compressive and/or tensile forces thereto. The curved configuration can be adapted to resemble the path of the anatomical lumen in which the device is positioned. Application of the actuation force maintains, or stiffens, the bend portions in the desired curved configuration. A medical device or instrument can then be advanced through the curved portion to a target location within the subject.

The device shown in FIG. 14 can alternatively be configured to be operated in this manner. For example, steerable delivery device 256 in FIG. 14 can be actuated to have a first bend or curved region 254 and a second bend or curved region 258. The curves, or bends, form a general S-shaped portion of the device. The delivery device 256 can be maintained, or locked, in the general S-shape to guide a medical device or instrument therethrough. The S-shape of the delivery device 256 can be used if it resembles a portion of the anatomy into which it is placed, but any other type of preformed configuration can be used, depending on the anatomical requirements. In the alternative to FIG. 14, the delivery device can be actuated into the configuration shown by the application of compressive and/or tensile forces to inner and outer tubular members, as is described herein.

Figure 29:
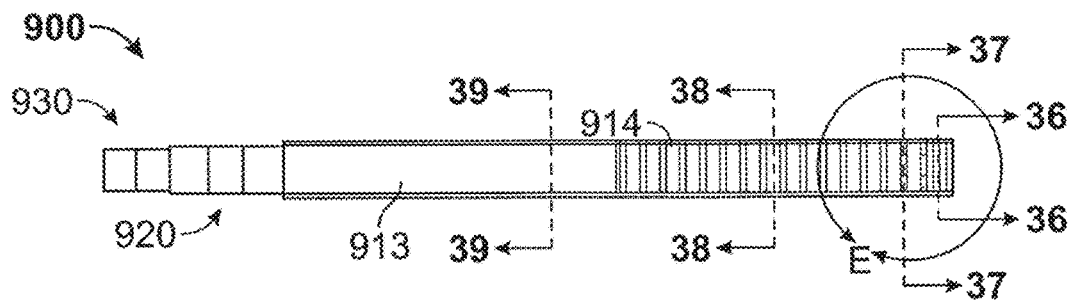
FIGS. 29, 30, 31, 32, 33 and 34 illustrate different views of an exemplary steerable medical device.
Figure 30:
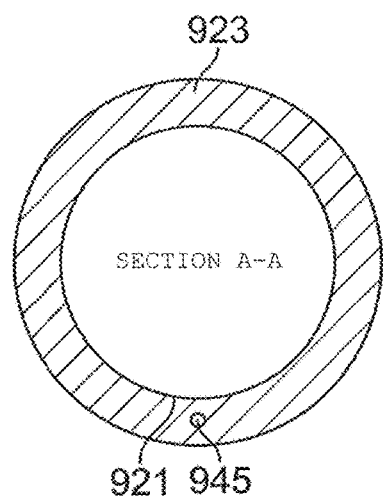
Figure 33:
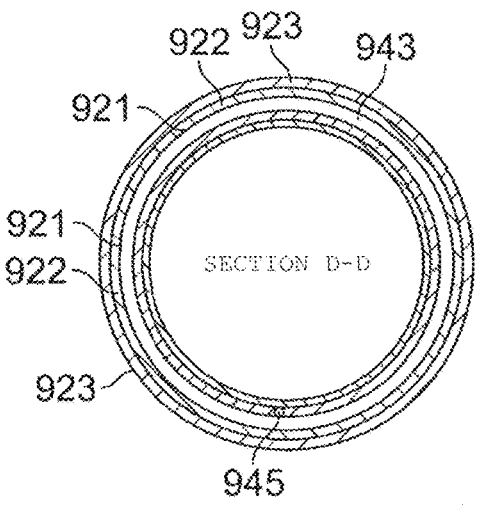
Figure 34:
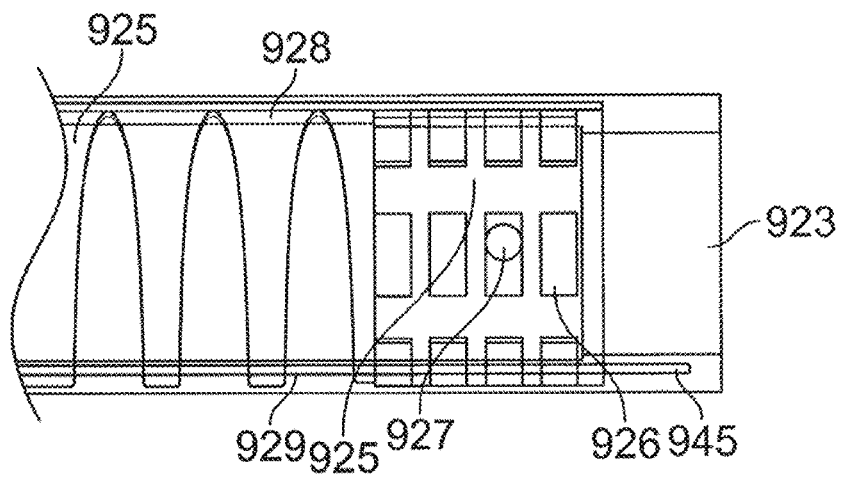

FIGS. 29-34 show an alternative embodiment of a steerable delivery device. FIGS. 29-34 illustrate steerable delivery sheath 900 capable of bending in one direction with torqueability and bend retention enhancements. FIG. 34 is an enlarged view of a distal-most portion of sheath 900. Sheath 900 includes inner tubular member 930 and outer tubular member 920, respectively. Cross sections of sheath 900 are represented in FIGS. 30-33. Locations of cross sections are indicated as sections A-A, B-B, C-C, and D-D as indicated in FIG. 29. Construction of sheath 900 in proximal portion 913, shown in cross section D-D shown in FIG. 33, is similar to the proximal portion for sheath 810. Table 1 describes component properties for an exemplary embodiment of the sheath shown in FIGS. 29-34. As in sheath 810, the distal-most portions of the inner and outer tubular members 930 and 920 are merged together, as is shown in section A-A in FIG. 30. In section A-A they are thus permanently axially fixed. Inner tubular member 930 includes three discrete components—inner layer 931, braided layer 932, and outer layer 933. In this embodiment inner layer 931 is a lubricious liner, layer 932 is a braided material embedded in PEBAX outer layer 933. Outer tubular member 920 includes inner layer 921, intermediate layer 922, and outer layer 923. In this embodiment, inner layer 921 is a lubricious liner, intermediate layer 922 is a braided material embedded in outer PEXAX layer 923.

In contrast to sheath 810, however, inner sheath 930 incorporates an additional stiffening element 945 that provides stiffness, only in tension, along the axis falling on the plane within which the distal end of the sheath bends. The proximal end of stiffening element 945 is embedded in the outer polymer layer 933 of the inner tubular member 930 at a location in a distal portion of the proximal portion 913 of the inner tubular member 930, as shown in FIG. 33. Stiffening element 945 is free floating in the annular space 943 between inner tubular member 930 and outer tubular member 920 throughout the remaining portion of proximal portion 913, as well as in distal bendable portion 914 of sheath 900 up to a point at the distal end of distal portion 914 where the distal portion of stiffening element 945 is embedded in outer polymer layer 923, which is shown in section A-A in FIG. 30. Stiffening element 945 is located in the plane through which the distal end of sheath 900 bends and is located on the inside radius of the bend. In some embodiments stiffening element 945 is a multi-stranded Kevlar line. In some embodiments the proximal end of stiffening element is secured to the outer layer of the inner tubular member at a location that is closer to the steerable portion of the device than a proximal end of the inner tubular member.

Distal portion 914 is the steerable portion of sheath 900 and is constructed as follows. In the proximal region of distal portion 914 (section C-C), the braid in layer 922 is replaced by a tubular structure with cutouts, and can be a metal tubular structure. The cutouts allow for the controlled variation in the bending stiffness of the outer tubular member in different planes which extend through the longitudinal axis. The cutout pattern may additionally incorporate features to enhance torsional stiffness.

In this embodiment element 925 is a part of the spine of pattern cut tube 922 and 927 is an aperture passing through all layers of the device.

TABLE 1

| 1-way steerable sheath | Proximal | Central/Middle | Distal |
|---|---|---|---|
| Inner sheath | | | |
| Liner | 1 to 2 mil PTFE | 1 to 2 mil PTFE | 1 to 2 mil PTFE |
| Braided Material | Diamond | Diamond | Diamond |
| PEBAX (Durometer) | 70 to 80 | 50 to 70 | 20 to 40 |
| Outer Sheath | | | |
| Liner | 1 to 2 mil PTFE | 1 to 2 mil PTFE | 1 to 2 mil PTFE |
| Braided Material | Herring | Herring | None |
| Cut Tube | None | None | Patterned |
| PEBAX (Durometer) | 70 to 80 | 50 to 70 | 20 to 40 |

Figure 35:
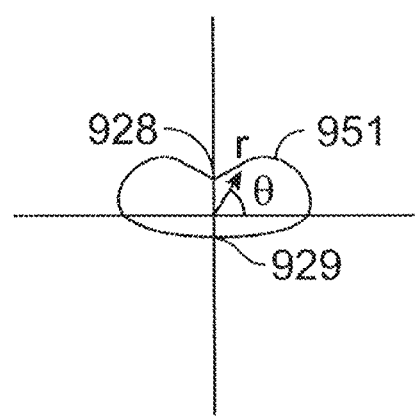
FIG. 35 illustrates a representation of the performance of the device in FIGS. 29-34.
Figure 36:
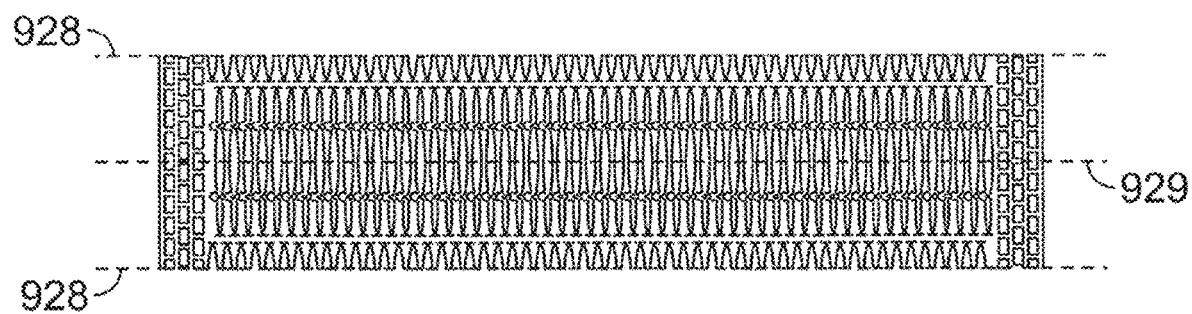
FIG. 36 illustrates an embodiment of a cut-out pattern incorporating both controlled variation in bending stiffness and features which enhance torsional stiffness.

A representation of the performance of such a tube with cutouts is depicted in FIG. 35 where curve 951 represents the stiffness in compression along axis on the periphery of the tube parallel to the longitudinal axis of the cut tube. The stiffness is represented on a polar plot where r represents the stiffness and theta the angle around the longitudinal axis pointing at the measurement axis. One embodiment of a cut-out pattern incorporating both controlled variation in bending stiffness and features which enhance torsional stiffness is represented as a flat pattern in FIG. 36.

Figure 31:
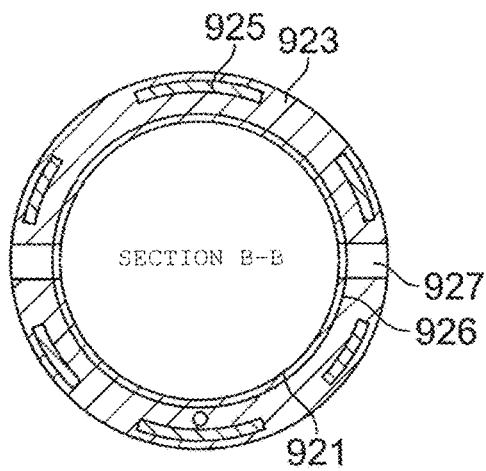
Figure 32:
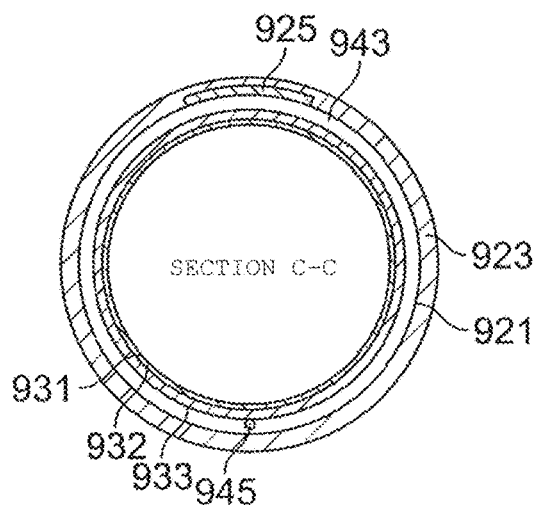

Bending in the steerable portion 914 of steerable sheath 900 occurs by axially translating the inner and outer tubular members relative to each other along the longitudinal axis. In some embodiments this is accomplished by fixing the outer sheath 920 to a handle or external controller incorporating an internal mechanism that is adapted to translate inner tubular member 930. As inner tubular member 930 is translated distally relative to outer sheath 920, compressive forces are applied to outer sheath 920. These compressive forces cause distal portion 914 of sheath 900 to bend in the direction of its most compliant axis, indicated by 929 in FIGS. 34, 35 and 36. As illustrated stiffening element 945 is adjacent to axis 929 and provides additional tensional stiffness to inner sheath 930 on this axis while allowing the opposed axis 928 to stretch. Sheath 900 in FIG. 34 additionally incorporates a radio opaque marker 927 at its distal end. 926 is a cut out in layer 922 through which polymer can pass, as shown in FIG. 31. The section with the square cutouts is completely embedded in polymer, hence all of the material is secured together at the distal end in FIG. 34 allows for the delivery of fluid from within the sheath to outside the sheath when the distal end of the sheath is plugged as might occur when the device is used to deliver a balloon which is inflated after delivery through the sheath and pulled back against the distal end.

Figure 37:
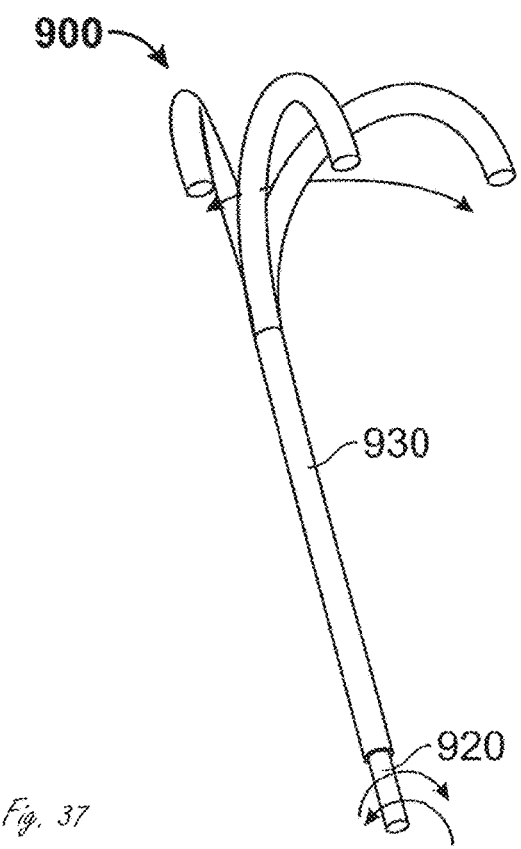
FIG. 37 illustrates inner and outer tubular members rotated relatively to one another thereby causing the bent distal end of the sheath to rotate in a generally circular arc.

In the embodiments shown in FIGS. 29-34, the inner and outer tubular members may be rotated relatively to one another, thereby causing the bent distal end of the sheath to rotate in a generally circular arc as shown in FIG. 37. This allows for more control of the distal tip by very finely torqueing just the distal end. This type of control minimizes whipping to an even greater degree.

Figure 38:
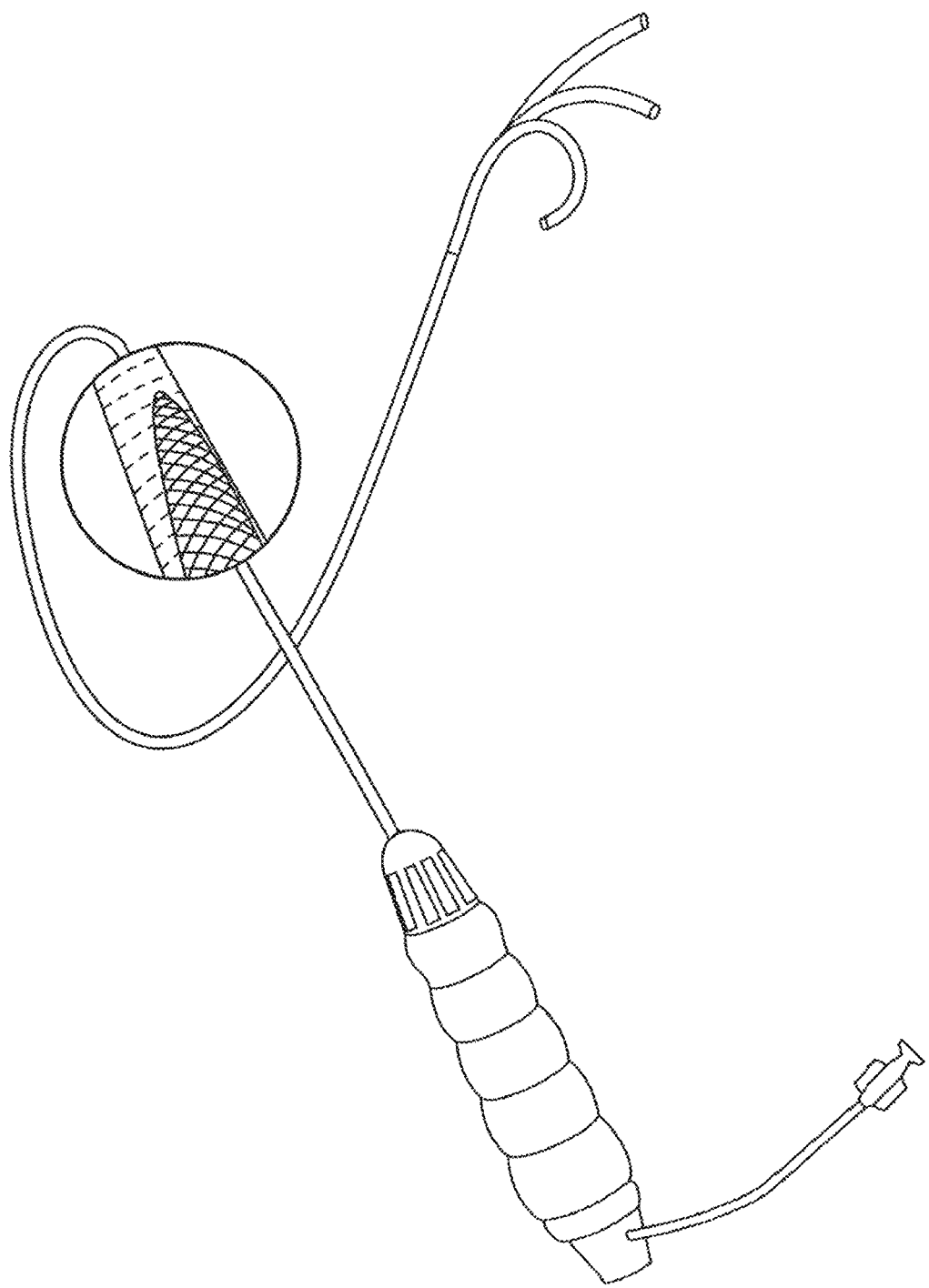
FIG. 38 illustrates an exemplary steerable device with an external actuator.

FIG. 38 illustrates an exemplary steerable device that can be controlled as described herein. The device includes an exemplary external actuatable component incorporated into a handle at its proximal end. The handle includes a first actuator at its distal end that is adapted to be actuated (e.g., rotation) to deflect, or steer, the tip as described herein. The handle also includes a second actuator at its proximal end that is adapted to be actuated (e.g., rotation) for fine tune torque adjustment as described in FIG. 37.

Figure 39:
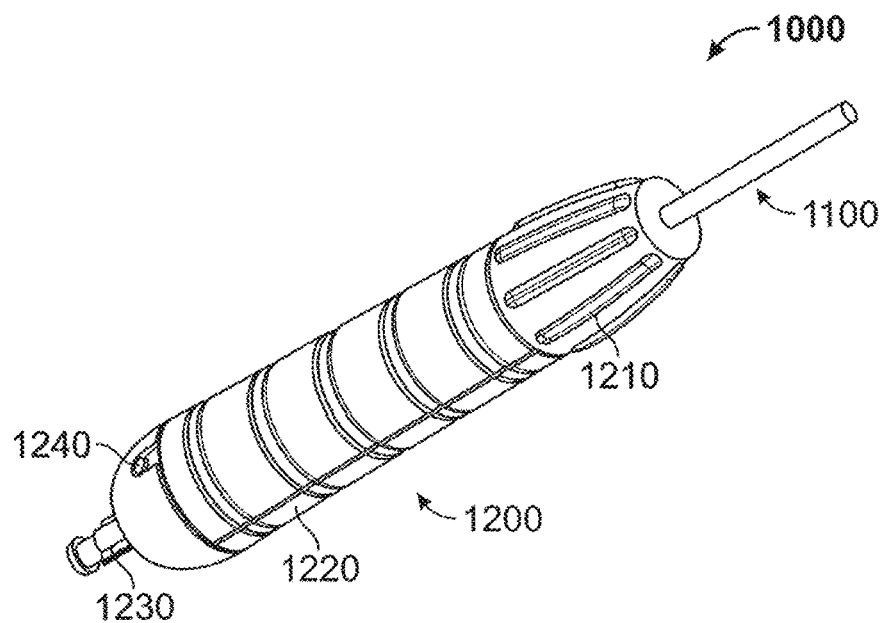
FIGS. 39, 40 and 41 illustrate different views of an exemplary external controller.
Figure 40:
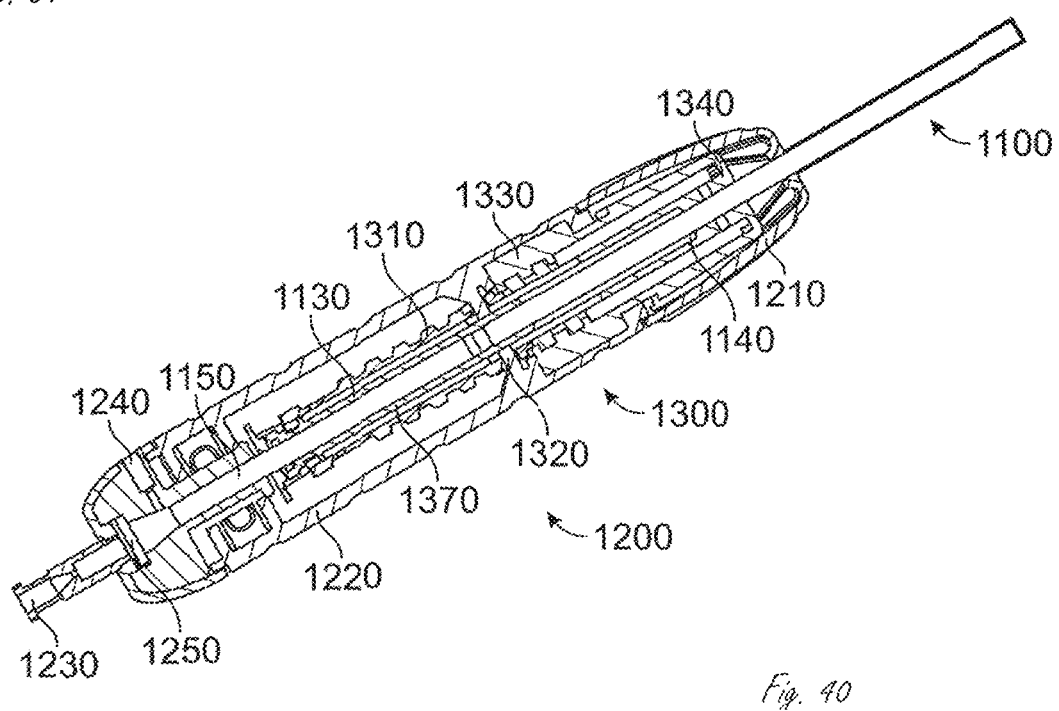
Figure 41:
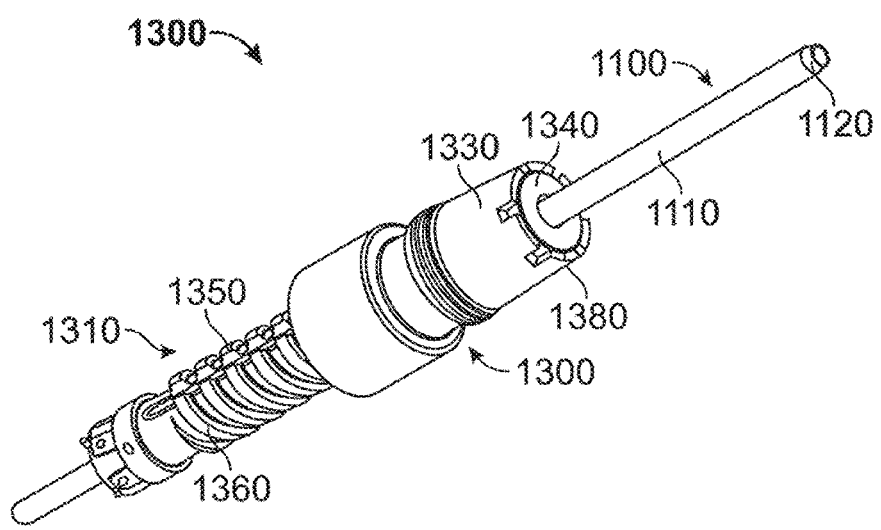

FIGS. 39-41 illustrate an exemplary external controller, in the form of a handle, that is adapted to deploy and actuate the steerable devices described herein. The external controller is adapted, or can be adapted to control other steerable devices not specifically described herein. FIGS. 39 and 40 illustrate the proximal portion of an exemplary steerable sheath system 1000 that includes steerable sheath 1100, such as those described above, and handle portion 1200 for actuating steerable sheath 1100. Handle portion 1200 includes sheath flexure adjustment knob 1210, grip 1220, guide wire port 1230, inner lumen purge port 1240 leading into central lumen 1150. Flexure, or steering, of the steerable sheath is facilitated by twisting control knob 1210 relative to handle grip 1220. The amount of flexure of the sheath is related to the amount of rotation of adjustment knob 1210. In some embodiments there will be a relatively linear correspondence between the degrees of rotation of control knob 1210 and the angle of flexure for the sheath steerable section. In such an embodiment each unit of incremental rotation of the control knob 1210 substantially equals or "maps" into a corresponding and constant unit of incremental flexure for the sheath steerable portion, independent of the starting flexure of the steerable sheath. In alternate embodiments there can be a nonlinear correspondence. For example, in an exemplary configuration when the steerable section is at minimal flexure, control knob 1210 can impart twice as much flexure as when it is at about 50% of its allowable flexure.

Other mappings are considered here although not described in detail. FIG. 40 illustrates a cross-sectional view of handle portion 1200 of FIG. 39 at a midline plane. Situated at the proximal end is guide wire pass-through 1230 which sits proximal to guide wire seal 1250 leading into central lumen 1150.

Additional features comprising the control mechanism 1330 are also shown. Control knob 1210 sits over drive nut 1330 and is constrained against rotation relative to the drive nut by drive nut feature 1380. Control knob 1210 and drive nut 1330 in turn are positioned concentrically around drive screw 1310. Outer sheath interface tube 1340 sits concentrically within the drive nut 1330.

Outer shaft 1110 is anchored to the outer sheath interface tube at 1140. Anchoring may be accomplished with adhesives, ultrasonic welding, heat staking or other suitable means. Inner shaft 1120 is anchored at 1130 to inner sheath interface tube 1370 via any of the mechanisms described for the outer sheath.

Handle housing 1220 feature 1320 passes through a proximal end of outer sheath interface tube 1340 constraining it from both rotation and axial displacement. Pins 1320 additionally ride in the drive screw stabilizing slot feature 1350 of drive screw 1310 pictures in FIG. 41. FIG. 41 depicts a portion of control mechanism 1300 with housing features removed. As control knob 1210 is rotated, drive nut 1330 is constrained to rotate with it via features 1380 and corresponding feature within the control knob, not shown. Since drive screw 1310 is constrained against rotation by the drive screw stabilizing pin 1320 riding in slot 1350, rotation of drive nut 1330 is translated into a linear motion for drive screw 1310. Drive screw thread 1360 may comprise a constant pitch or a variable pitch. Since the inner shaft is anchored to the inner sheath interface tube which in turn is constrained from moving axially relative to screw 1310, this in turn will be translated into axial motion of the inner sheath relative to the outer sheath and result in flexure, or steering, of the steerable portion of the device.

An exemplary aspect of the disclosure includes embodiments that facilitate the visualization of portions of the steerable sheath when used in a navigation system, such as the St. Jude NavX Navigation & Visualization Technology, or other impedance-based methods associated with identifying relative positions of system components within a living or deceased body.

When a steerable device includes one or more tubular members, as in the embodiments described above, the distal section of one or more of the tubular member can sometimes compress, or shorten, when it is actuated to straighten the tip of the steerable device. For example, in the embodiments above which include an inner tubular member disposed within an outer tubular member, the distal section of the inner tubular member may sometime compress, or shorten, when it is pushed in relative to the outer tubular member to straighten the steerable portion from a bent configuration towards a straighter configuration. In some of these embodiments, the proximal section of the inner tubular member has a greater durometer (e.g., 72D) than the steerable portion (e.g., 35D). The lower durometer allows the steerable portion to bend. The shortening, when it occurs, is an inefficient use of the displacement of the inner tubular member that is necessary to deflect the steerable device.

FIGS. 42A-42G illustrate an exemplary embodiment that reduces or eliminates the shortening. In this embodiment, the region of the inner tubular member disposed on the inside of the curve in the steerable portion and the distal tip has a higher durometer than the rest of the inner tubular member in the steerable portion and distal tip. FIGS. 42B-42D show cross-sections through sections A-A, B-B, and C-C as indicated in FIG. 42A. Device 1650 includes inner tubular member 1652, outer tubular member 1654, and tensioning element 1660. Outer tubular member 1654 has the same durometer along the length of the outer tubular members. In section C-C, the inner tubular member includes a first portion 1658 with a first durometer. In sections B-B and A-A, the inner tubular member includes first portion 1658 with the first durometer and a second portion 1656 with a second durometer lower than the first durometer. First portion 1658 makes up about ¼ of the inner tubular member in cross section. First portion 1658 is radially within tensioning member 1660 that is used to transfer tension from the proximal section of the tubular member to the tip of the device. The higher durometer in the portion on the inside of the curve prevents the shortening of the inner tubular member when actuated. FIG. 42G shows section G-G of the distal section indicated in FIG. 42E. First portion 1658 can be seen on the inside of the curve radially within tensioning element 1660. In one specific embodiment first portion 1658 is 72D PEBAX, and second portion 1656 is 35D PEBAX. These numbers are exemplary and are not intended to be limiting.

FIGS. 43A-43D illustrate an alternative embodiment in which device 1700 includes inner tubular member 1702 and outer tubular member 1704. Inner tubular member 1702 has first section 1708 with a first durometer and a plurality of second sections 1706 with a second durometer lower than the first durometer. In this embodiment, the steerable portion (section B-B) and distal tip (section A-A) of the inner tubular member include two higher durometer sections 1708. In this embodiment neither of the higher durometer sections 1708 is radially within tensioning member 1710, and as such neither of sections 1708 is on the inside of the curve. The two higher durometer sections 1708 are substantially opposite each other around the circumference of the inner tubular member, and are each about 90 degrees apart from tensioning element 1710.

The exemplary steerable devices described in FIGS. 44-46 are similar to those shown in FIGS. 42A-G above. In particular, the inner tubular member of the steerable devices in FIGS. 44-46 is similar to inner tubular member 1652 described in reference to FIGS. 42A-G above.

FIGS. 44A-44C illustrate exemplary inner tubular member 4100. FIG. 44A is a top view. FIG. 44B is a view rotated 90 degrees relative to the FIG. 44A view, and FIG. 44C is a view rotated 180 degrees relative to the view in FIG. 44A (and 90 degrees relative to the view in FIG. 44B).

Inner tubular member 4100 includes steerable distal section 4114 and a proximal section 4102. Proximal section 4102 includes a proximal tubular element 4116 with a first durometer. In the embodiment shown proximal tubular element 4116 has a durometer of 72D and is a Pebax/Vestamid material. Steerable distal section 4114 includes tubular element 4104 and spine 4106. Spine 4106 is similar to first portion 1658 from FIGS. 42A-G herein. Tubular element 4104 has a lower durometer than proximal tubular element 4116. In this embodiment tubular element 4104 has a durometer of 35D, and is Pebax. Spine 4106 has optional proximal and distal cuff portions that extend all the way around the device, and a spine section that extends between the two cuff portions that does not extend all the way around the device. In the spine section spine 4106 makes up about ¼ of inner tubular member 4100, and tubular element 4104 makes up about ¾ of the inner tubular member 4100. Inner tubular member 4100 also includes tensioning member 4108 that is secured to the distal end 4110 of cuff portion and to the distal end 4112 of proximal section 4102. Tensioning member 4108 is free floating in between the two points at which it is secured. Tensioning member 4108 is directly adjacent to, and in alignment with, the spine section of spine 4106 (as can be seen in FIG. 44C). In this embodiment tensioning member 4108 is a Kevlar line. Spine 4106 has a greater durometer than tubular element 4104, and in this embodiment is 72D Pebax.

As is described in more detail above, the lower durometer of tubular element 4104 relative to proximal tubular element

4116 allows the steerable distal section to bend. Spine 4106, however, due to its higher durometer, reduces shortening in compression and stretching in tension, as can occur in the distal section when it is actuated. For example, the distal section of the inner tubular member may sometimes compress, or shorten, when it is pushed in relative to the outer tubular member to straighten the steerable portion from a bent configuration towards a straighter configuration. The durometers provided are not intended to be limiting but merely illustrative.

Figures 45A, 45B, 45C:
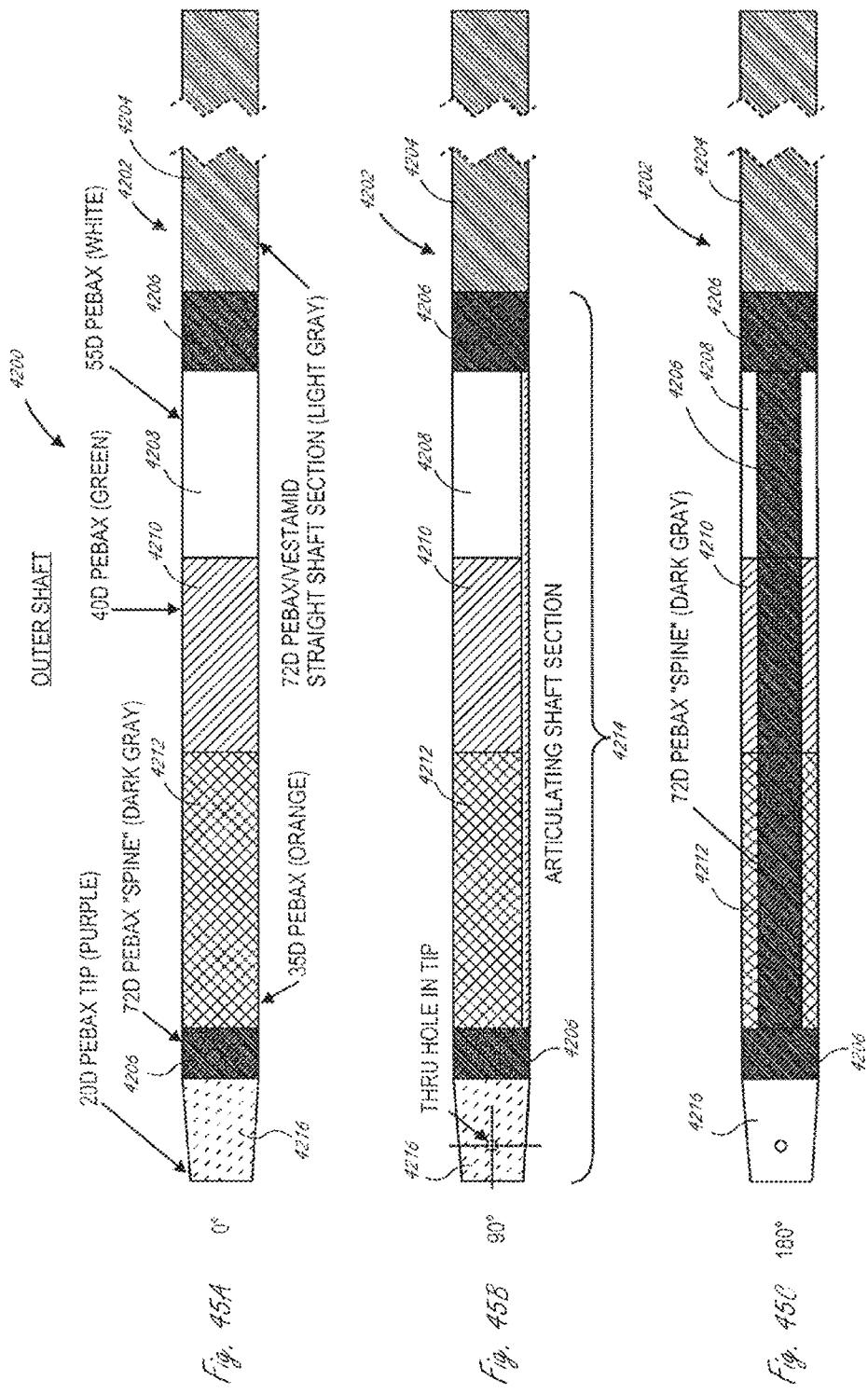
FIGS. 45A-45C illustrate an exemplary outer tubular that is part of a steerable device and is disposed outside of and around an inner tubular member from FIGS. 44A-44C. FIG.

FIGS. 45A-45C illustrate exemplary outer tubular 4200 that is part of the delivery device and is disposed outside of and around inner tubular member 4100. FIG. 45A is a top view. FIG. 45B is a view rotated 90 degrees from the view in FIG. 45A, and FIG. 45C is a view rotated 180 degrees from the view in FIG. 45A (and 90 degrees from the view in FIG. 45B).

Outer tubular member 4200 includes a proximal section 4202 and steerable, or articulating, distal section 4214. Proximal section 4202 has a proximal tubular element 4204 with a first durometer. In this embodiment proximal tubular element 4204 is a 72D Pebax/Vestamid material. Distal articulating section 4214 includes spine 4206, which is structurally the same as the spine in FIGS. 44A-44C. Spine 4206 includes distal and proximal cuffs and a spine section extending between the two optional cuff portions. In this embodiment spine 4206 is 72D Pebax. Articulating section 4214 also includes first section 4208, second section 4210, and third section 4212, all of which have different durometers. In this embodiment the durometers decrease towards the distal end of the device. In this embodiment first section 4208 is 55D Pebax, second section 4210 is 40D Pebax, and third section 4212 is 35D Pebax. The multiple sections of different durometer materials (three in this embodiment) in the outer tubular member are arranged so that, as the steerable portion is steered, the radius of curvature changes along the length of the steerable portion. In this embodiment, the radius of curvature of the steerable portion decreases along the length of the steerable portion, and thus is less in the distal region than in more proximal sections. The steerable portion has a tighter curvature in the distal region than in the proximal region. The configuration of the steerable portion can be thought of as a spiral in this embodiment. In contrast, in embodiments in which a single durometer material extends the length of the steerable portion (except for the spine), the radius of curvature of the steerable portion is substantially the same along the length of the steerable portion (i.e., regardless of the location along the length of the steerable portion). In the single durometer design the radius of curvature does decrease in response to continued external actuation, but the radius of curvature remains substantially the same along the length of the steerable portion. The curve thus becomes tighter, but it has a substantially constant radius of curvature along the steerable portion. The materials and the arrangement of the materials in the steerable portion can thus be selected depending on the desired application of the device. For example, different degrees of desired bending, or steering, may differ depending on the intended use of the device, including any intended target location within the body.

Proximal tubular element 4204 has a greater durometer than all three sections 4208, 4210, and 4212. The distal articulating section 4214 also includes distal tip 4216. In this embodiment distal tip 4216 is the lowest durometer material, and in this embodiment is 20D Pebax.

The embodiments herein with the outer spine and the multiple durometer steerable sections provides for advantages in bidirectional use. For example, less force is required to bend the multiple durometer arrangement, hence there is less foreshortening or conversely less stretching when the element is used in tension. This advantage would also hold true for unidirectional steering.

As is described in more detail in the assembly shown in FIGS. 46A-46C, the spines in the inner and outer tubular members are offset 4180 degrees from one another. Tensioning member 4108 is therefore also offset 180 degrees from the outer spine.

FIGS. 46A-46E illustrate views of assembly 4300 including the inner and outer tubular members 4100 and 4200, respectively, from FIGS. 44 and 45. As can be seen in FIGS. 46A and 46E, tensioning member 4108 is offset 180 degrees from outer spine 4206. The inner and outer spines are also offset by 180 degrees.

The assembly 4300 can be used as is described in the applications incorporated by reference herein. For example, the inner and outer tubular members can be axially moved relative to one another to steer the distal steerable section. When a spine from one tubular member is put in tension, the other spine is put in compression. The dual spine embodiment reduces shortening in one tubular member in compression and stretching in the other tubular member in tension.

In some embodiments the inner or outer tubular members are formed by positioning the different materials on a mandrel, placing shrink wrap over the different materials, and increasing the temperature, which causes the material to melt together, forming the inner or outer tubular members. The optional cuffs described above can be helpful in securing one or more components together during the manufacturing process.

Any of the inner and outer tubular members described above that comprise one or more slots or spines can be made of an elastomeric or polymeric material. For example, the tubular members shown in FIG. 2, 3, or 4 with slots and spines therein can be made from Pebax or other polymeric materials.

The embodiment in FIGS. 47-49 describes alternative designs for inner and outer shafts described herein. The assembly of the inner and outer tubular member described in FIGS. 47-49 can be actuated and thus steered in the same or similar manner as is described above. For example, the tubular members in the example in FIGS. 47-49 are axially fixed relative to one another distal to a steerable portion, and the steerable portion can be steered by actuating the inner or outer tubular member relative to the other tubular member via actuation of an external device. Actuating the external device (e.g., a handle) causes the tubular members to be axially moved relative to one another proximal to the steerable portion, which causes their relative axial movement in the steerable portion, which thereby causes the steerable portion to be steered. The amount of relative movement between the tubular members decreases as the distance from the axial fixation location decreases. Due to the axial fixation, when one tubular member is put in tension, the other is under compression. For example, if the inner shaft is moved proximally relative to the outer shaft via actuation of the external control (and the proximal end of the outer shaft is not moved proximally), the inner shaft is put in tension. Because the shafts are axially fixed and the outer shaft does not move proximally, the outer shaft will be under compression. In alternative embodiments, details of the inner and outer tubular members disclosed above may be incorporated into the tubular members described in the embodiment in FIGS. 47-49, unless this disclosure specifically indicates to the contrary.

FIGS. 47A-47I illustrate details of an exemplary inner tubular member, which may also be referred to herein as an inner shaft (or member) subassembly. FIGS. 48A-48E illustrate details of an exemplary outer tubular member, which may be referred herein as in outer shaft (or member) subassembly. FIGS. 49A-49D illustrate details of the steerable device assembly comprising the inner and outer tubular members from FIGS. 47A-47I and FIGS. 48A-48E, respectively. Additionally, the assembly in FIGS. 49A-49D illustrates a soft tip at the distal end, which can be added after the inner and outer tubular members are assembled.

Figure 47A:
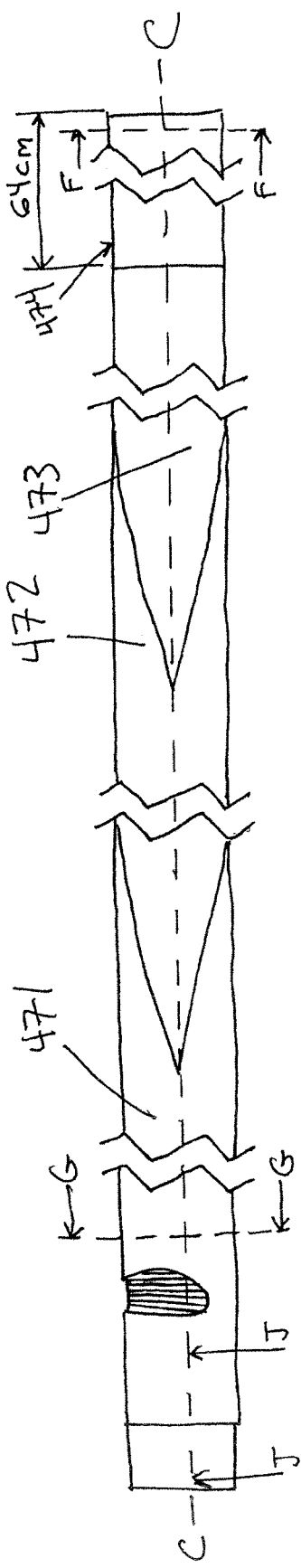
Figure 47B:
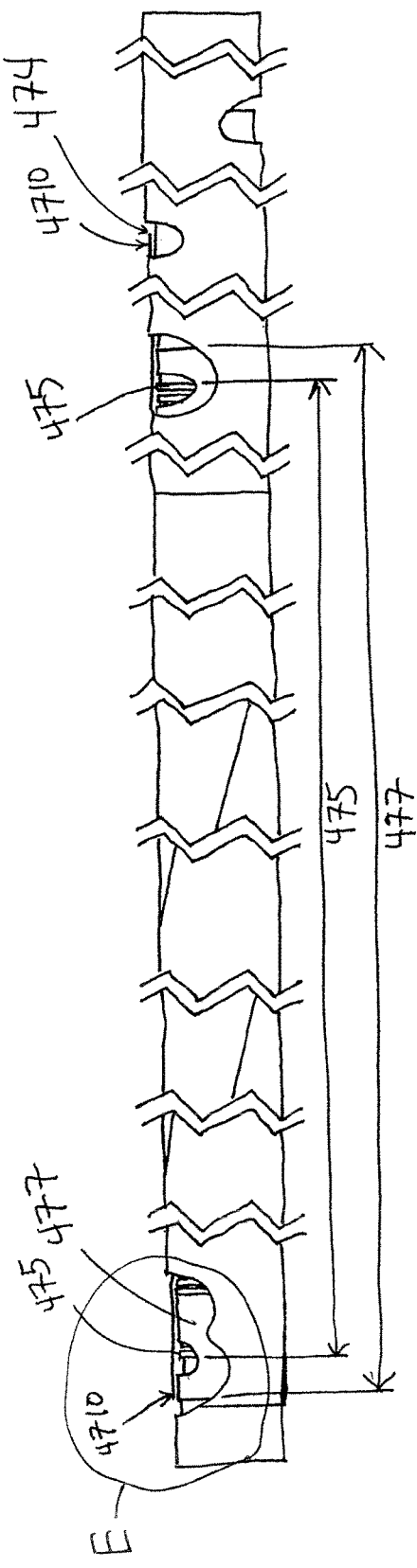

FIGS. 47A and 47B illustrate side views of the steerable portion of an exemplary inner tubular member, with select portions cut away to review additional detail. FIG. 47B is a side view that is 90 degrees around the tubular member relative to the side view in FIG. 47A. "Distal" is to the left in the figure, and "proximal" is to the right in the figure. The steerable portion of the inner tubular member includes three sections of material that are each coupled with at least one adjacent section at a seam that is not parallel to and not perpendicular to the longitudinal axis of the tubular member, and can be an angled seam. As shown in FIGS. 47A and 47B, the steerable portion includes, in a proximal-to-distal direction (right-to-left in FIGS. 47A and 47B), three different sections, the durometer of the sections decreasing in the proximal-to-distal direction. For example, as shown in FIG. 47A, the steerable portion includes section 473 (e.g., 72D Pebax), intermediate section 472 (e.g., 55D Pebax), and proximal section 471 (e.g., 35D Pebax). These durometers are merely exemplary and the other durometers can be used. In some embodiments the durometers decrease in the proximal-to-distal direction, in others the central durometer may be the greatest. The joint, or seam, between section 473 and 472 is not parallel to and not perpendicular to the longitudinal axis of the inner shaft, and in some embodiments it is an angled seam. The joint between sections 472 and 471 is also not parallel to and not perpendicular to the longitudinal axis of the inner shaft, and in some embodiments is an angled seam. The joint may, however, not form a straight line between adjacent sections and still be considered to be non-parallel and non-perpendicular to the longitudinal axis. In this embodiment the joints are non-parallel and non-perpendicular to the longitudinal axis over substantially the entire joint. "Substantially the entire joint" in this context includes joints that have end sections that are perpendicular to the longitudinal axis. "Substantially" in this context refers to joints wherein most of the joint is non-parallel and non-perpendicular to the longitudinal axis, such as at least eighty percent of its length.

In this embodiment, the varying durometers in the three sections of the inner shaft have similar functionality to those described above in the context of FIGS. 45A-45C. The multiple sections of different durometer materials (three in this embodiment) in the inner tubular member are arranged so that, as the steerable portion is steered, the radius of curvature changes along the length of the steerable portion. In this embodiment, the radius of curvature of the steerable portion decreases along the length of the steerable portion, and thus is less in the distal region than in more proximal sections. The steerable portion has a tighter curvature in the distal region than in the proximal region. The configuration of the steerable portion can be thought of as a spiral in this embodiment. In contrast, in embodiments in which a single durometer material extends the length of the steerable portion (except for the spine), the radius of curvature of the steerable portion is substantially the same along the length of the steerable portion (i.e., regardless of the location along the length of the steerable portion). In the single durometer design the radius of curvature does decrease in response to continued external actuation, but the radius of curvature remains substantially the same along the length of the steerable portion. The curve thus becomes tighter as it is steered, but it has a substantially constant radius of curvature along the steerable portion. The materials and the arrangement of the materials in the steerable portion can thus be selected depending on the desired application of the device. For example, different degrees of desired bending, or steering, may differ depending on the intended use of the device, including any intended target location within the body.

In the embodiment in FIGS. 42A-42G above, the average durometer in cross sections (perpendicular to the longitudinal axis of the shaft) throughout the inner shaft in the steerable portion remains constant. In an effort to allows for tighter bending curves in the distal direction in the steerable portion during bending, at least one of the shafts in the steerable portion can have an average durometer, in cross sections through the steerable portion, that varies along its length (i.e., is not constant along its length). The varying average durometer can be incrementally (i.e., step-wise) varying (e.g., FIG. 45), or it can be continuously varying (e.g., FIG. 47, via the non-parallel and non-perpendicular seams). Any configuration of the seams can be chosen to control the variance in the average durometer in the cross sections.

In other embodiments the outer shaft has a non-constant (i.e., varying) average durometer in cross section along its length. In some embodiments both of the shafts have varying average durometers in cross section along their lengths.

In any of the embodiments, in either shaft, there can alternatively be more than or fewer than three sections with different durometers in the steerable portion.

In this embodiment the bending plane of the inner shaft is, in FIG. 47B, the plane of the page. The bending plane in this embodiment (and others herein) is a plane that includes the spine, the longitudinal axis, and preferential bending axis. The spine extends through the top of the shaft in FIG. 47B (although the spine itself in some embodiments is not necessarily a linear "axis." For example, a spine can have a midline parallel to the longitudinal axis of the shaft that is an "axis"). The preferential bending axis is in the plane of the page and extends through the bottom of the shaft in FIG. 47B. When put under compression the shaft will bend downward in the page in the bending plane. When bent, the spine, the longitudinal axis, and the preferential bending axis remain in the bending plane. With respect to the seam between sections 473 and 472, the distal-most location of section 473 is in the spine, in the bending plane. The proximal-most location of section 472 is along the preferential bending axis. Thus, the distal-most location of the higher durometer material is along the spine, and the proximal-most location of the relatively lower durometer material is along the preferential bending axis. As discussed above, the average durometer of the shaft, in cross section perpendicular to the longitudinal axis, continuously varies from the proximal-most location of section 472 and the distal-most location of section 473.

In this embodiment the distal-most location of the seam between sections 473 and 472 is along the spine, and the proximal-most location of the seam is in the preferential bending axis.

The inner member includes a proximal portion 474 that is proximal to the steerable portion. Proximal portion 474 is generally stiffer than the steerable portion. In some embodiments proximal portion 474 is a polyamide, such as nylon or Vestamid. FIG. 47E shows cross section F-F (from FIG. 47A) through proximal portion 474.

FIG. 47C shows cross section G-G within the steerable portion from FIG. 47A. The innermost layer is liner 476, which can be a lubricious liner such as PTFE. Section G-G also shows a portion of support member 475 (in this embodiment is a helical coil) embedded in the inner member. Support member 475 can be a stainless steel wire, and in section G-G is embedded in distal section 471, which in this embodiment comprises 35D Pebax. Also embedded in distal section 471 is reinforcing member 477, which can be, for example, a Kevlar line. The length of reinforcing member 471 and coil 475 are shown in FIG. 47B.

FIGS. 47G-47I, respectively, show side views of distal section 471, intermediate section 472, and proximal section 473 before they are assembled.

Figure 47F:
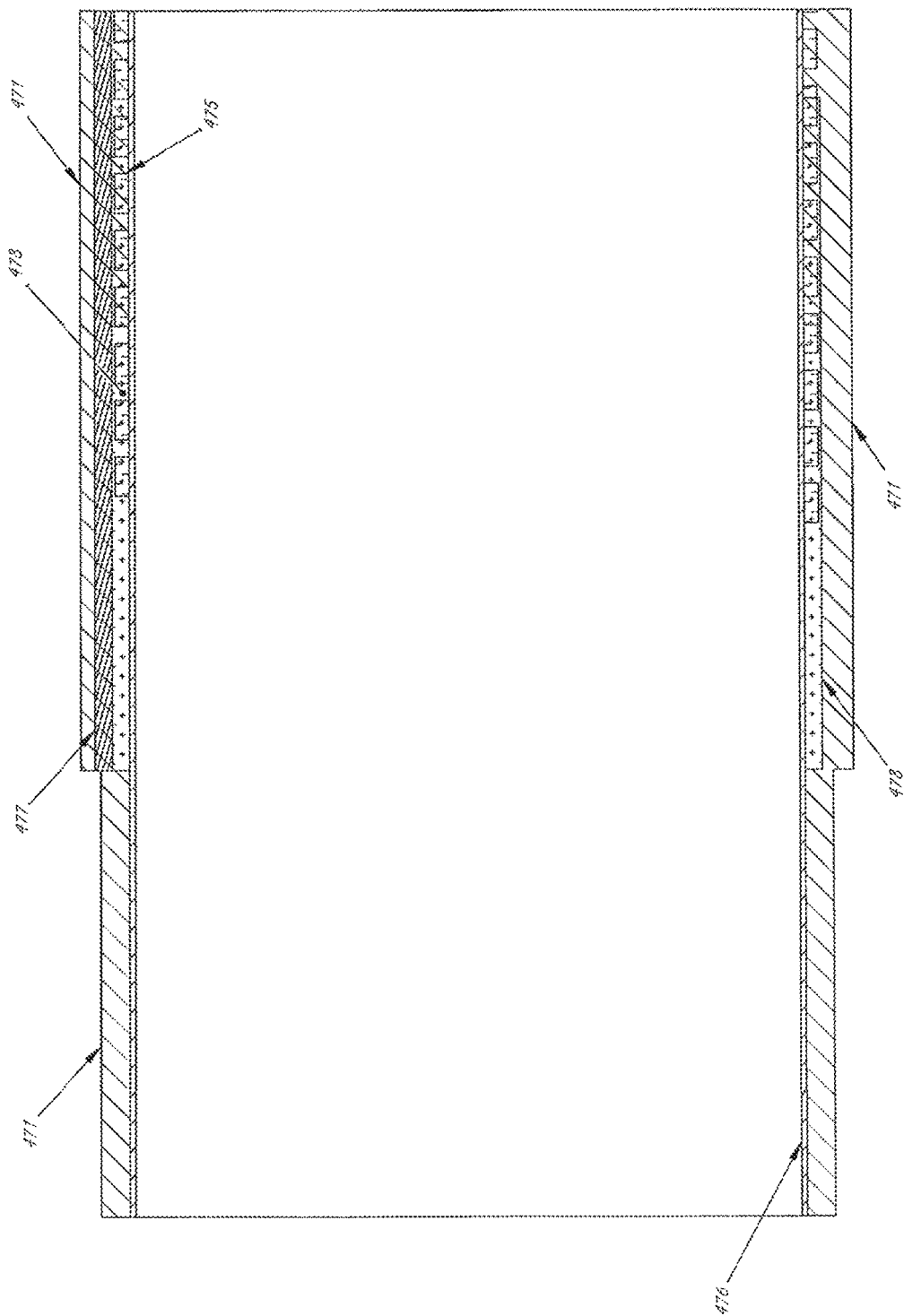

FIG. 47F shows section J-J of the distal end of the device from FIG. 47A. The ends of coil 475 are embedded in a thin polyamide such as Vestamid, and the distal of the two is labeled 478 in FIG. 47E. Reinforcing member 477 can also be seen, the distal end of which is proximal to the distal end of the device. Inner liner 476 extends all the way to the distal end of the device.

As shown in FIGS. 47G-47I, and as described above in the context of FIGS. 47A and 47B, adjacent sections in the steerable portion meet at a joint that is not parallel with and not perpendicular to the longitudinal axis of the shaft, which in some embodiments can be very slightly radially overlapped. In some embodiments it can be an angled joint. The slight overlap can help diminish flaws associated with the kitting of the two materials. In embodiments in which the joints are angled, exemplary angles for the seams are shown in FIGS. 47G-47I, but these are merely exemplary. One difference between the inner tubular member shown in FIGS. 47A-47I and the inner members in the embodiments above is that reinforcing member 477, which can be a Kevlar material, is completely embedded in the inner tubular member, as opposed to being free-floating at certain points along its length or embedded in the outer surface of the outer member. A reinforcing member can also be woven through a support member, such as a braided material. The reinforcing member and the support member would then be embedded in the inner member. In this embodiment the reinforcing member is linearly aligned with the spine of the shaft. A reinforcing member can thus be woven through a braided material, extending in a generally linear direction, and still be considered "linearly aligned" with a spine in this context.

Figure 48C:
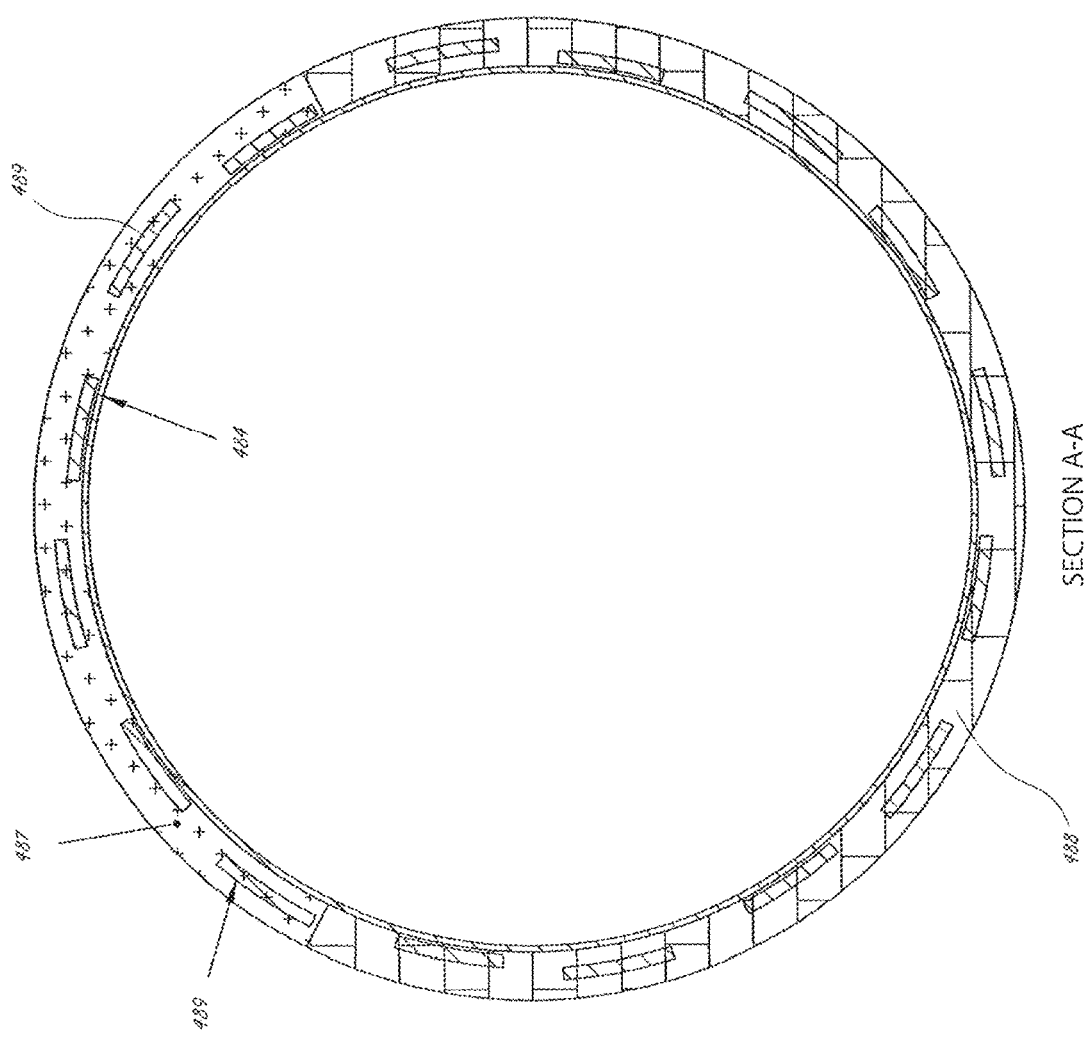
Figure 49C:
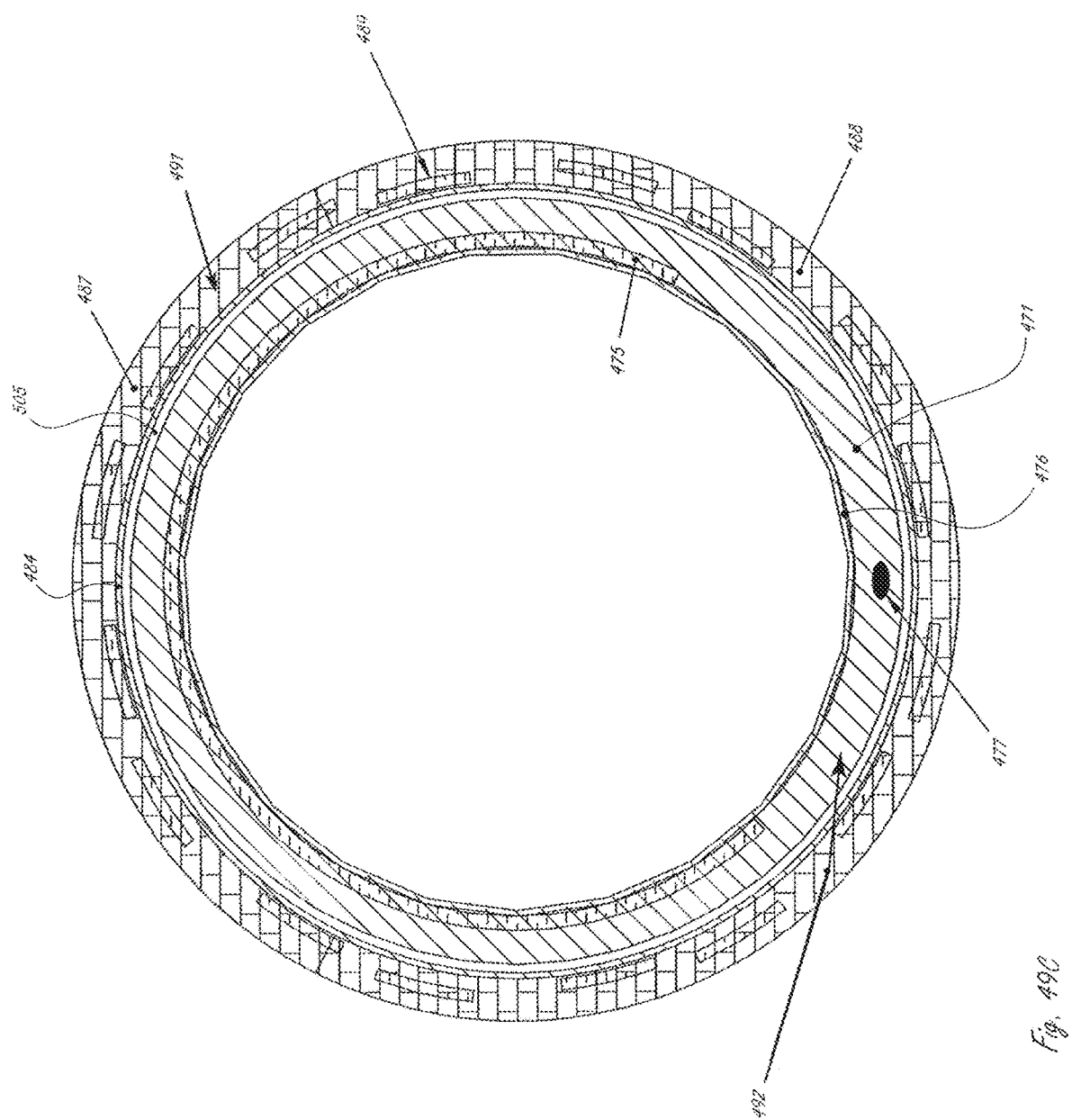

FIGS. 48A-48D illustrate an exemplary outer tubular member. FIGS. 48A and 48B are the same relative views of the outer tubular member as are the views from FIGS. 47A and 47B of the inner tubular member. The outer member includes a proximal portion 481 that is disposed proximal to steerable portion 501. In an exemplary embodiment proximal portion 481 can be a 72D Pebax material. Along steerable portion 501, the outer tubular member includes sections of material that have different durometer. In this embodiment steerable portion 501 includes first section 487 with a high durometer than a second section 488. First section 487 acts as a spine along steerable portion 501. In a merely exemplary embodiment first section 487 can be a 72D Pebax material and second section 488 can be a 35D Pebax material. First section 487 extends less than 180 degrees around the outer shaft, and second section 488 extends more than 180 degrees around the outer shaft. The joints between the two materials are parallel to the longitudinal axis (as that term is used in the art) of the outer shaft. In other embodiments, however, the joints between sections 487 and 488 can be non-parallel to the longitudinal axis of the outer tubular member, and may also be non-perpendicular to the longitudinal axis of the outer tubular member. For example, the joint between sections 487 and 488 can include an angled joint.

FIG. 48C shows section A-A shown in FIG. 48A. The outer shaft includes an inner liner 484, which can be a lubricious liner such as PTFE. Supporting member 489, in this embodiment in the form of a braided material, is disposed around liner 484. The polymeric outer shaft includes lower durometer section 488 and higher durometer section 487. As can be seen, the supporting member 489 is embedded in the polymeric tubular member.

FIG. 48D illustrates section C-C of outer shaft shown in FIG. 48A (distal end towards the left in the figure). Immediately distal to the section that includes first and second sections 487 and 488 is a section of material with higher stiffness than steerable section 501. In some embodiments section 485 can be a 72D Pebax material. Supporting member 489 extends into section 485. Liner 484 also extends into section 485. Distal to section 485 is a tip section of outer shaft, which includes an outer layer 482 and an inner layer 486. Outer layer 482 is stiffer than inner layer 486. As an example outer layer 482 can be a 72D Pebax, and inner layer 486 can be a 35D Pebax. The distal tip also include marker band 483, which is radially within outer layer 482 and radially outward relative to inner layer 486. The distal tip also includes a braided material captured, or retained, by marker band 483. Marker band 483 may be formed from a radiopaque material such that the distal tip is visible under fluoroscopy. For example, marker band 483 may be formed from a radiopaque alloy, e.g., a platinum-iridium alloy.

FIGS. 49A-49D illustrate views of an exemplary steerable device that includes outer shaft 491 (from FIGS. 48A-48D) affixed to inner shaft 492 (from FIGS. 47A-47I). The assembled steerable device also includes a soft tip 493 at the distal end that is affixed to the inner and outer shafts after they are affixed to one another.

Components from FIGS. 47A-47I and FIGS. 48A-48D are again labeled in FIGS. 49A-49D. As can be seen most clearly in FIG. 49C, reinforcing member 477 (e.g., a Kevlar line) of the inner shaft 492 is 180 degrees opposite from the midpoint of higher durometer section 487 (measure around the perimeter of device orthogonal to the longitudinal axis) in the outer shaft 491.

Figure 49D:
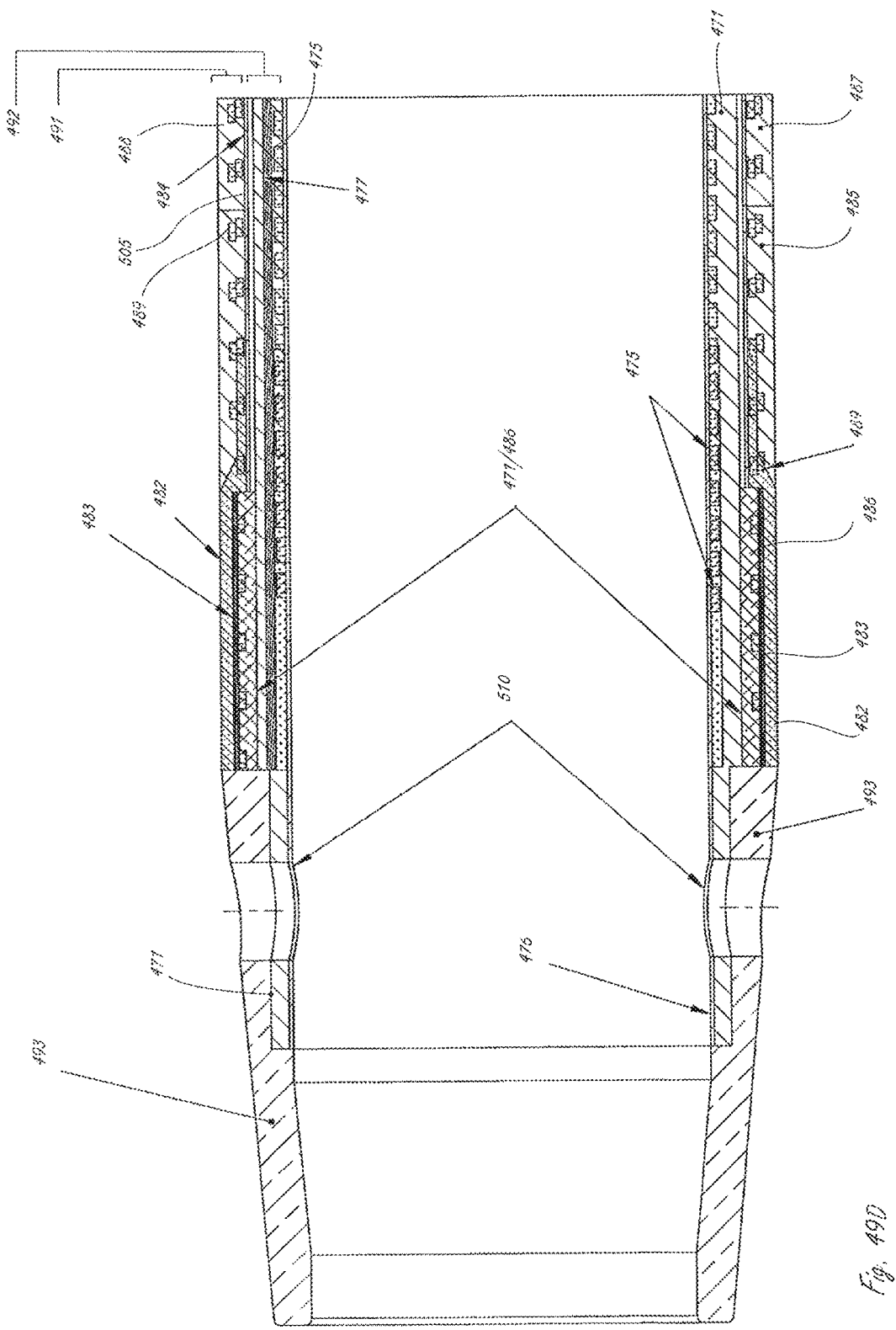

FIG. 49D shows section E-E of the device from FIG. 49A. There is a space 505 between inner shaft 492 and outer shaft 491 in the steerable portion. As can be seen in FIG. 49D, inner shaft 492 and outer shaft 491 are affixed to one another at the interface between section 471 of the inner shaft and inner layer 486 of the outer shaft (see inner layer 486 in FIG. 48D). As can be seen in FIG. 49D, inner shaft 492 extends further distally than outer shaft 491. The portion of inner shaft 492 that extends further distally than outer shaft 491 includes section 471 and inner liner 476. Soft tip 493 is disposed radially over the distal end of inner shaft 492, and is also axially interfaced with the distal end of outer shaft 491, as shown in FIG. 49D. The polymeric components are affixed to one another using known techniques. After soft tip 493 is affixed, vent holes 510 are made in the assembly, which are aligned with the reinforcing member 477 of inner shaft 492 and the spine of outer shaft 491. The steerable device can be assembled to any of the handles herein and can be actuated to steer the steerable portion in the manners described herein.

Figure 50A:
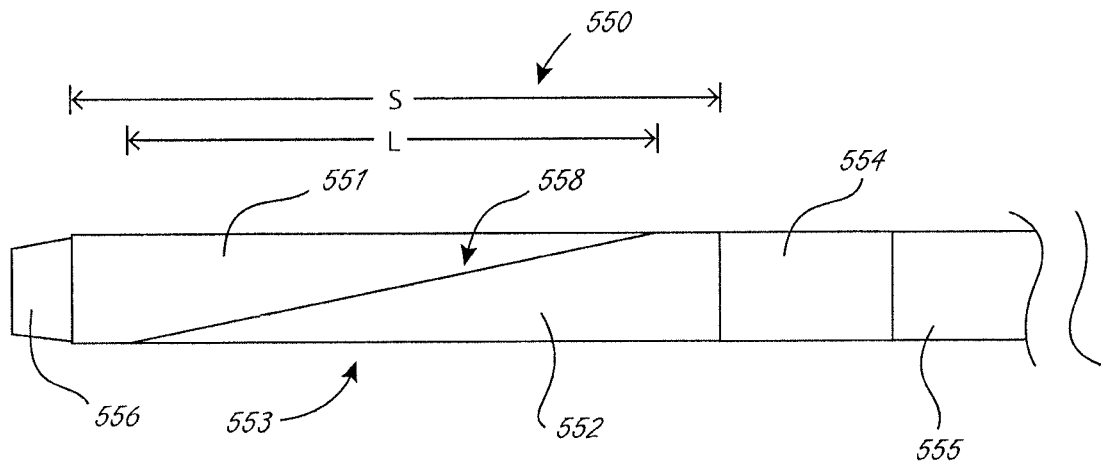
FIGS. 50A and 50B are side views of an exemplary inner tubular member, including an exemplary angled seam.
Figure 50B:
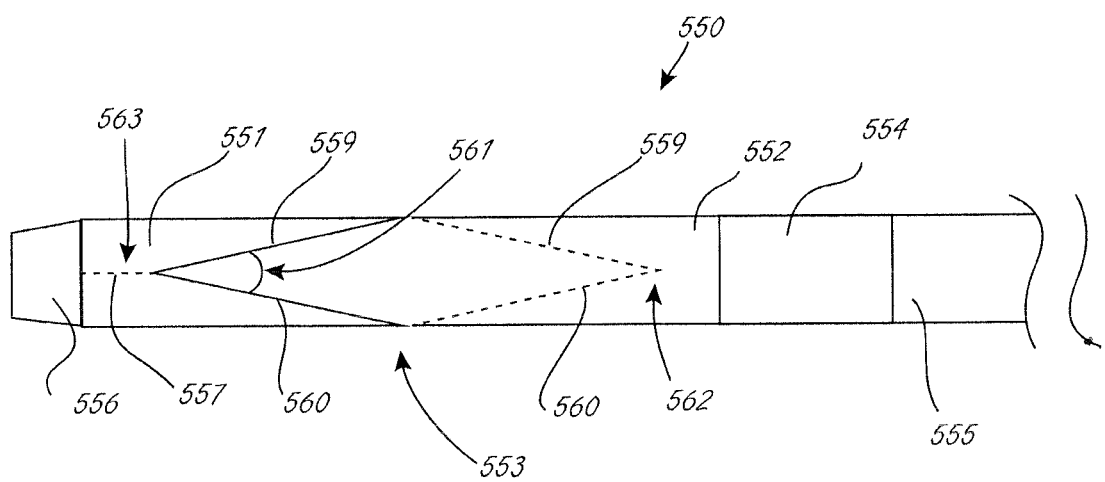

FIGS. 50A and 50B illustrate side views of a distal region of an alternative inner tubular member 550, with the views in FIGS. 50A and 50B 90 degrees relative to one another. Inner tubular member 550 can be used in combination with any of the outer tubular members herein. In this exemplary embodiment, steerable portion 553 includes first segment 551 and second segment 552 interfacing at seam 558. Steerable portion 553 is similar to the steerable portion in the embodiment in FIGS. 47A and 47B, but in steerable portion 553 there are only two segments, 551 and 552, that interface at a seam.

FIG. 50B illustrates that seam 558 comprises first and second seams 559 and 560, which meat at seam distal-most location 563 and seam proximal-most location 562.

In this exemplary embodiment, seam 558 is angled along its entire length, shown as length "L" in FIG. 50A. "Angled," when used in this manner, describes a seam that is not parallel with and not perpendicular to a longitudinal axis of the inner tubular member, which may be the same as a longitudinal axis of a steerable medical device of which the inner tubular member is a part. The seam may also be angled along substantially its entire length, such as at least 85% of its length. For example, the distal and/or the proximal-most locations of the seam may include short straight sections that are perpendicular to the longitudinal axis of the inner tubular member, and the seam can still be angled along substantially its entire length.

The angled seam 558 may also be described in terms of a comparison of cross-sectional areas of the inner tubular member in the longitudinal direction. For example, cross-sectional areas taken at different locations between distal-most point 563 and proximal-most point 562 of the steerable portion may include C-shaped segments having different material durometer that mesh to create a circular cross-section. By way of example, a first cross-section taken several millimeters proximal from the distal-most point 563 may include a first C-shaped segment having a higher durometer and having a smaller arc length, and a second C-shaped segment having a lower durometer and having a larger arc length. By contrast, a second cross-section taken several millimeters distal from the proximal-most point 562 may include a first C-shaped segment having a higher durometer and having a larger arc length, and a second C-shaped segment having a lower durometer and having a smaller arc length. In the case of seam 558 angled linearly and at a continuous angle between the distal-most point 563 and the proximal-most point 562, a third cross-section taken at a medial location between the distal-most and proximal-most points may having a first C-shaped segment having a higher durometer and a second C-shaped segment having a lower durometer, and the first and second C-shaped segments may have a same arc-length, i.e., may be semi-circular.

Seam 558 may include an angle relative to the longitudinal axis that varies over its length. For example, a seam that is angled along substantially its entire length can still include one or more relatively short perpendicular or parallel seam sections along its length. That is, seam 558 may include discrete steps, each of which includes a perpendicular and a parallel segment relative to the longitudinal axis. Thus, the stepped profile of the angled seam 558 may progress around a surface of steerable portion 553 at an angle, even though one or more segments of the seam are not directed at an angle.

Seam 558 may include other profiles that progress around the surface of steerable portion 553 at an angle. For example, the seam profile may be continuous (as opposed to a discrete profile of a stepped seam profile), but the angle of the seam may vary. In an embodiment, the variably-angled seam profile may include a wavy profile beginning at a distal-most location 563 and progressing around the surface of steerable portion in a wavy manner to a more proximal location that is circumferentially offset relative to distal-most location 563.

While inner tubular member 550 includes a seam that is angled along its entire length, inner tubular 550 is also an example of a tubular member with a seam, at least a portion of the seam being angled along its length.

First segment 551 (which can also be considered a distal segment) has a durometer less than the durometer of second segment 552 (which can also be considered a proximal segment). In some embodiments, first segment 551 has a durometer of 20D-55D, such as 25D-45D, and in a particular embodiment can be about 35D. In some embodiments second segment has a durometer of 55D-85D, such as 65D-85D, and in a particular embodiment is about 72D.

In some embodiments the inner tubular member includes a segment of tubular material 554 proximal to the steerable portion, and segment of tubular material 555 proximal to segment 554. In some exemplary embodiments section 554 can be a polyamide such as Vestamid®. In some embodiments segment 555 has a durometer between 55D-85D, such as 65D-85D, such as about 72D. In other embodiments the inner tubular member excludes section 555, and thus section 554 (e.g., a Vestamid material) extends all the way to a handle assembly.

In some embodiments the difference in durometers between the first and second segments is at least 10D, at least 15D, at least 20D, at least 25D, at least 30D, or even at least 35D. The one or more angled portions of seam 558 create one or more transitioning portions of the inner tubular member with a varying durometer along the angled seam.

The length of seam L as a percentage of the length of steerable portion "S" of inner tubular member 550 is, in this embodiment, relatively high. In this embodiment the length L is at least 80% of length S, but in some embodiment it can be at least 50%, 55%, 60%, 65%, 70%, 75%, 80%, 85%, 90%, or 95%. An exemplary advantage of angled seam 558, and its relative length, is that it can provide a more consistent, or smooth, curvature to the steerable portion of the steerable medical device during steering. The angled seam creates a continuously changing stiffness along the length of the angled seam, due to the different durometers of the two materials. For example, a stiffness of inner tubular member 550 may decrease, in a stepped or continuous manner, in a distal direction from proximal-most location 562 to distal-most location 563. Some alternative designs may have steerable portions that have a tendency to form "joints" along the steerable section during steering (i.e., a less smooth curvature), and the exemplary angled seam 558 can help reduce the likelihood of a "jointed" steerable section, if desired.

In some embodiments the length of the seam L can be between 1 cm and 8 cm, such as between 2 cm and 7 cm, or between 3 cm and 6 cm.

In some embodiments the length of the steerable portion S is from 3 cm to 9 cm, such as from 3 cm to 8 cm, or 4 cm to 7 cm, such as, without limitation, 4.5 cm, 4.6 cm, 4.7 cm, 4.8 cm, 4.9 cm, 5.0 cm, 5.1 cm, 5.2 cm, 5.3 cm, 5.4 cm, 5.5 cm, 5.6 cm, 5.7 cm, 5.8 cm, 5.9 cm, 6.0 cm, 6.1 cm, 6.2 cm, 6.3 cm, or 6.4 cm.

In some embodiments the steerable medical device includes inner tubular member 550 and, for example without limitation, the outer tubular member in FIGS. 48A-D. The lengths of the steerable portions of both the inner and outer tubular members are generally the same, such as any of the exemplary lengths herein. Inner tubular member 550 can be incorporated into the steerable medical device such that the steerable portion is steered upon actuation of an external actuator, examples of which are described herein. For example, in some embodiments the outer tubular member is axially fixed with respect to an external handle, and the inner tubular member is operatively coupled with the external actuator on the external handle such that actuation of the actuator causes relative axial movement (e.g., proximal movement) of the inner tubular member. A proximal force on the inner tubular member puts the inner tubular member in tension, and because the inner and outer tubular members are axially fixed distal to the steerable portion, the outer tubular member is put into compression, thereby steering the steerable portion.

Compression of the outer tubular member and tensioning of the inner tubular member, or vice versa, may create length changes of differing amounts on opposing sides of the respective tubular members. Taking the inner tubular member as an example, tensioning of the inner tubular member may stretch the side of the steerable portion having the lower durometer material more than the side of the steerable portion having the higher durometer material having the higher durometer material. The difference in material strain may translate into a radius of curvature of the tubular member. A similar phenomenon may occur in the outer tubular member under compression, in which the lower durometer material is compressed more than the higher durometer material. In either case, it is noted that a radius of curvature is achieved through different strain rates of material along the solid walls, i.e., non-slotted, sides of the tubular members. More particularly, the steerable portion may be curved and steered using tubular members that do not include slots, holes, or discontinuities in the walls of the tubular members over the steerable portion. In alternative embodiments, one or both of the inner and outer tubular members may include a steerable portion that does not include a solid tube of polymeric material. For example, one or both of the inner and outer tubular members may have, in the steerable portion, one or more discontinuities in the polymeric member. Discontinuities could be in the form of, for example, one or more holes of any configuration, or one or more slots of any configuration, and can extend along any desired length of the steerable portion. One exemplary function of such a discontinuity could be to act as a strain relief in one or more portions of the one or both tubular members. An exemplary method of creating a discontinuity could be to create one or more, for example, holes in the polymeric material after the tubular member has been formed.

Figure 51A:
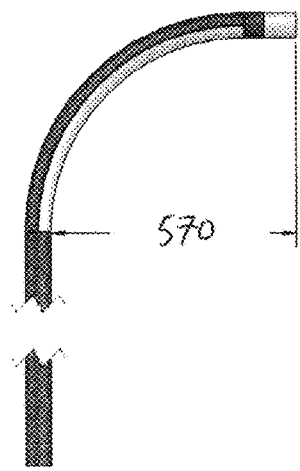
FIGS. 51A and 51B illustrate flexing, or bending, of an exemplary steerable medical device.
Figure 51B:
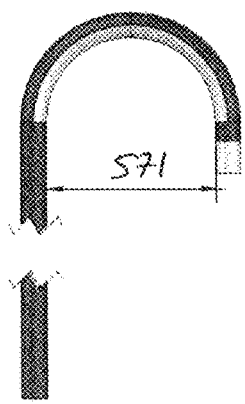

The lengths of the steerable portion of the medical device, as well as the configuration and properties of the different segments of material in the steerable portion, will, generally, influence the configuration that the steerable portion will assume when steered. The configuration includes the tightness of the curve of the steerable portion after it has been steered, or bent, to the fullest extent. The lengths of the steerable section S set forth immediately above can allow the steerable portion to achieve a curve diameter 571 of 2.0 cm-3.5 cm, the dimension of which is illustrated in FIG. 51B for an example steerable medical device. Curve diameter 571 may also be expressed in terms of a radius. For example, a reach length 570 may be a radius of curvature of the steerable portion when the steerable portion does not bend over 180 degrees or more. Exemplary reach lengths 570 shown in FIG. 51A, which is the dimension when the steerable portion is bent at 90 degrees, can be, for example without limitation, 2.7 cm-4.7 cm.

The proximal end of steerable portion 553 does not include an angled seam, and includes only second segment of material 552. Similarly, the distal end of steerable portion 553 does not include an angled seam, and includes only first segment of material 551, as can be seen in FIG. 50B. In an embodiment, however, one or more of the distal end of steerable portion 553 or the proximal end of steerable portion 553 may be coincident with distal section 556 or proximal section 554. That is, a vertex of seam 558, i.e., a point whether seam portions 559 and 560 meet, may coincide with a distal or proximal end of the steerable portion.

In some embodiments the segments 551 and 552 have the same length. The length of segments 551 and 552 will influence the location of the distal most and proximal most location of the seam.

First and second segments 551 and 552 have the same configuration, but they are offset by 180 degrees and face opposite directions. The first and second segments need not, however, have the same configurations.

FIG. 50B illustrates seam portions 559 and 560 forming acute angles (only distal angle 561 labeled) at both ends of seam 558. The length of the seam can influence the angle formed by the two seam portions 559 and 560. An "angle" as used in this context does not require two straight lines defining what is generally referred to as an angle. The general configuration of seam portions 559 and 560 can form an acute angle therebetween even if seam portions 559 and 560 are not perfectly straight lines in the side view (e.g., even if there is a slight curvature to one or both of them). Furthermore, seam portions 559 and 560 may meet at a vertex as described above, or alternatively, may terminate at a connecting segment that joins the portions 559 and 560 together. For example, linear or curved seam portions 559 and 560 may terminate at a curved segment having a radius that connects the ends of the seams together. Similarly, seam portions 559 and 560 may terminate at a circumferentially directed segment, e.g., a line running perpendicular to the longitudinal axis, that connects the ends of the seam together. Accordingly, the angular vertex illustrated in FIG. 50B is provided by way of example and not limitation.

The seams herein can be formed by interfacing different segments of material in any manner, such as butt joints, overlapping portions, non-overlapping portions, etc. The sections of the steerable portion may thus be spliced together along the seams and joined using known processes, such as welding or bonding using heat, adhesives, etc.

The distal most and proximal most locations of seam 558 are 180 degrees from another around the inner tubular member. The distal most and proximal most locations need not be defined by the intersections of two lines, but could include, for example, straight lines that are perpendicular to the longitudinal axis of the inner tubular member.

Figure 50C:
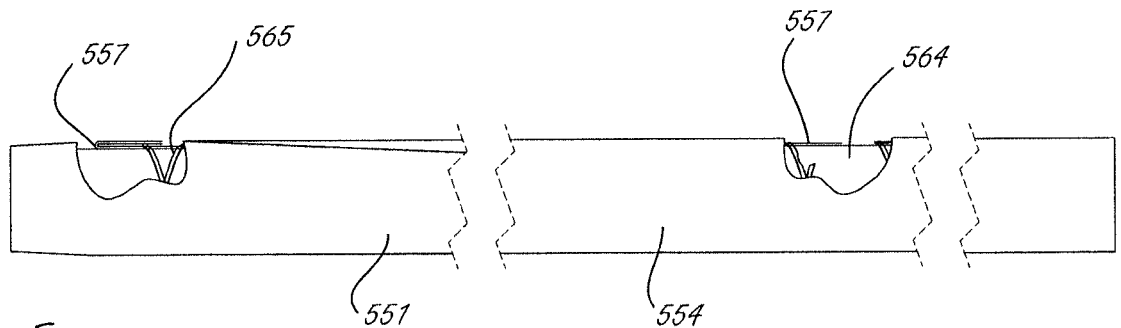
FIG. 50C is a side view of an exemplary inner tubular member, with cut out at select portions to illustrate some components of the inner tubular member.

Inner tubular member 550 also includes a reinforcing member 557 along its spine, which can be seen in FIG. 50C and shown in phantom in FIG. 50B. Reinforcing member 557 extends from a proximal end secured in section 554, to a distal end secured in steerable section 553. Reinforcing member 557 is, in this embodiment, woven in second reinforcing member 565, such as in an under-over pattern, a portion of which can be seen in FIG. 50C with select cutouts. Reinforcing member 557 can be woven in an under-over pattern such that it is changes its over-under position relative to second reinforcing member 565 every time it meets a new section of the second reinforcing member 565. In this embodiment second reinforcing member 565 is a braided material along at least a portion of its length. Reinforcing member 557 can alternatively be disposed on top of or below second reinforcing member 565. Reinforcing member 557, even when woven into (e.g., any type of over-under pattern) second reinforcing member 565, is disposed parallel to the longitudinal axis of inner tubular member 550. The distal end of reinforcing member 557 is everted, or folds back on itself, as shown in FIG. 50C. The distal end folds back and wraps around a segment of second reinforcing member 565, as shown in FIG. 50C. The distal end can fold back on top of, or below, the second reinforcing member 565, depending on the relative location of the reinforcing member 557. For example, in FIG. 50C, reinforcing member 557 extends distally from under second reinforcing member 565, and everts, or is folded back, on top of second reinforcing member 565. The everted length can be, for example, between 0.5 mm and 5 mm, such as between 1 mm and 3 mm. In some embodiments the length of the everted length is at least 0.5 mm, such as at least 1 mm. In an embodiment, the length of the everted section is a minimum of 1.5 mm. One or both ends of the reinforcing member can be everted in this manner. In some embodiments reinforcing member 557 is not woven in second reinforcing member 565 all of the way to the proximal end of reinforcing member 557. For example, reinforcing member 557 can be disposed over or under at least two braided wire portions at its proximal end.

Everting the distal end of reinforcing member 557 provides for a more secure anchoring of the reinforcing member 557 in the inner tubular member 550. Accordingly, a likelihood of movement of reinforcing member 557 relative to second reinforcing member 565, which could cause a predetermined shape of the steerable portion to be altered, may be reduced. The distal end of inner tubular member 550 is shown with a distal section 556, which is generally relatively flexible, and has a durometer less than second segment 552. Distal section 556 can have a durometer between 15D and 50D, such as between 25D and 45D, such as 35D.

Figure 50D:
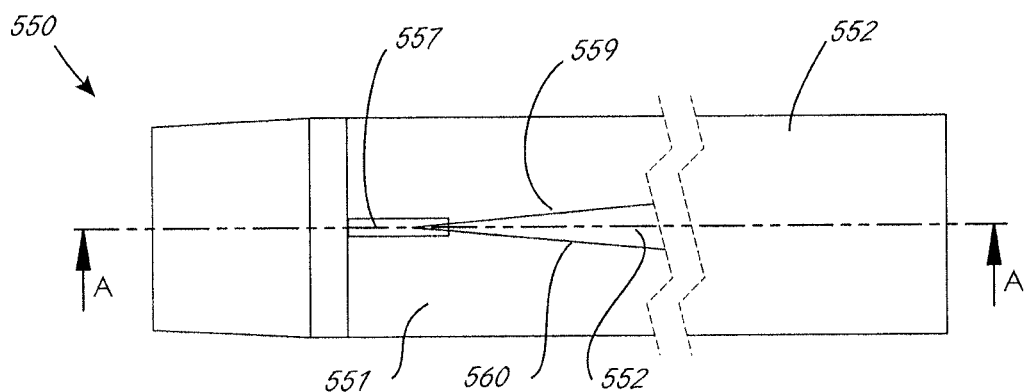
FIG. 50D is a side view of a portion of an exemplary inner tubular member.
Figure 50E:
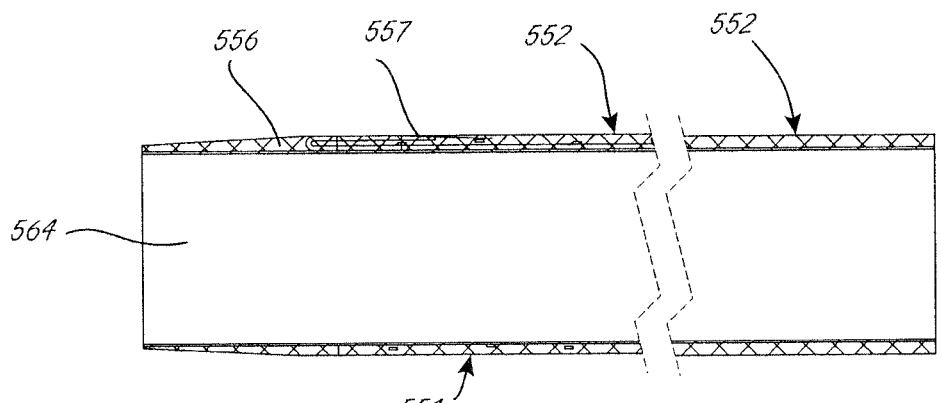
FIG. 50E is a section view of an exemplary inner tubular member shown in FIG. 50D.

FIG. 50D illustrates a distal region of inner tubular member 550, illustrating reinforcing member 557 disposed along the spine of the inner tubular member 550. Section A-A from FIG. 50D is shown in FIG. 50E, showing inner liner 564, relatively soft distal section 556, everted distal end of reinforcing member 557, and portions of first and second segments 551 and 552.

The inner and outer tubular members can be manufactured individually in a number of ways. One exemplary process is that the materials of the inner tubular member can be reflowed together on a mandrel using heat shrink tubing.

Any of the coils in the devices herein can be replaced with braided sections of material.

Figure 52A:
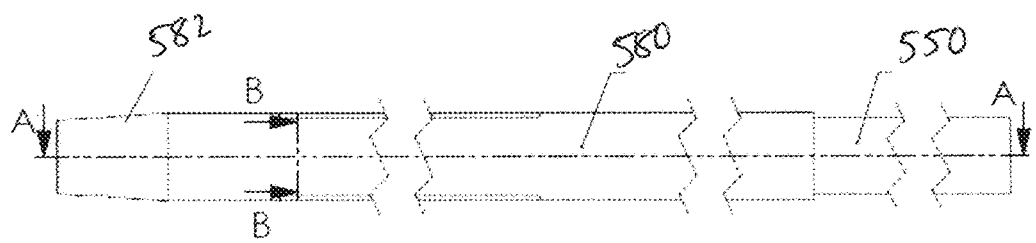
FIG. 52A is a side view showing a portion of an exemplary steerable medical device.
Figure 52B:
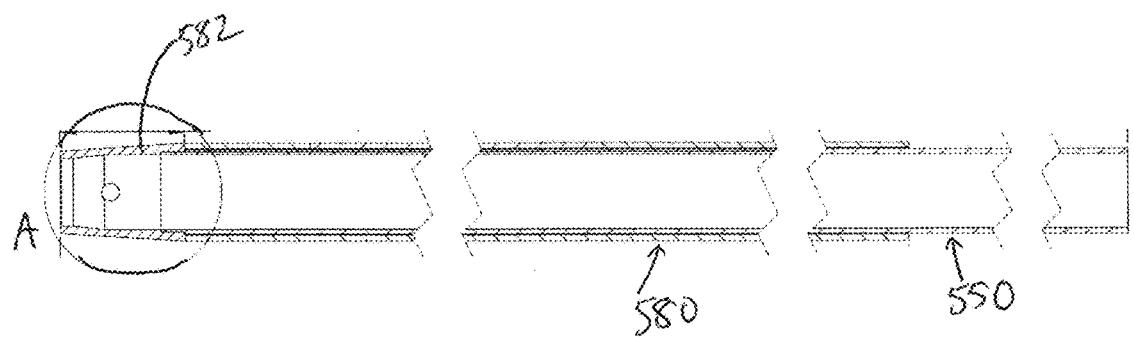
FIG. 52B is a section view of a portion of an exemplary steerable medical device shown in FIG. 52A.
Figure 52C:
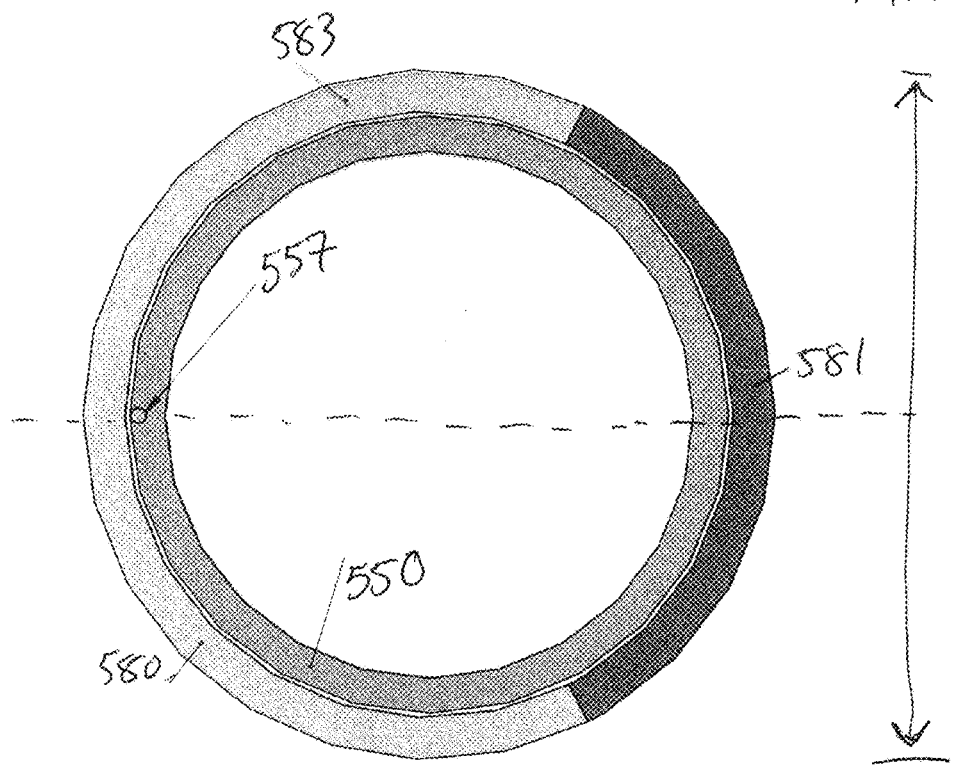
FIG. 52C is a section view of an exemplary steerable medical device shown in FIG. 52A.

FIG. 52A illustrates a portion of exemplary steerable medical device, including inner tubular member 550, outer tubular member 580, which can be the same or similar to the outer tubular member shown in FIGS. 48A-48D, and distal flexible section 582. FIGS. 52B and 52C illustrate sections A-A and B-B, respectively, shown in FIG. 52A. FIG. 52C illustrates inner tubular member 550, outer tubular member 580, and reinforcing member 557 of the inner tubular member being 180 degrees opposite the midpoint of the higher durometer segment, 581, in outer tubular member 580. In this design, and as described repeatedly throughout herein, the spines of the inner and outer tubular member are offset by 180 degrees. The relatively lower durometer material, segment 583, extends more than 180 degrees around outer tubular member.

Figure 52D:
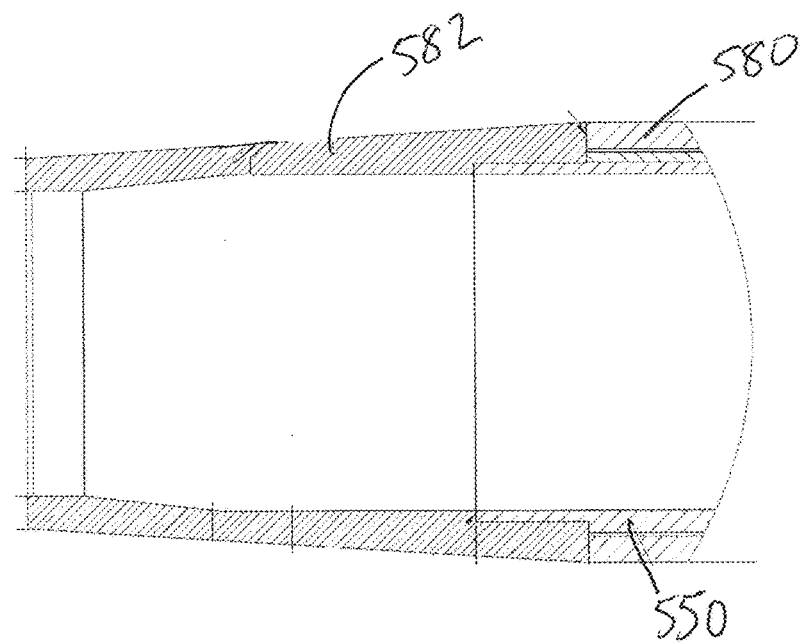
FIG. 52D shows a detail view of a distal end of an exemplary steerable medical device.

FIG. 52D shows Detail A from FIG. 52B, showing the distal end of the steerable medical device. Inner tubular member 550 extends slightly further distally than outer tubular member 580 as shown, and both engage distal flexible tip 582.

Figure 53A:
FIG. 53A is a perspective view of an exemplary steerable medical device, including a steerable sheath and an external controller.
Figure 53B:
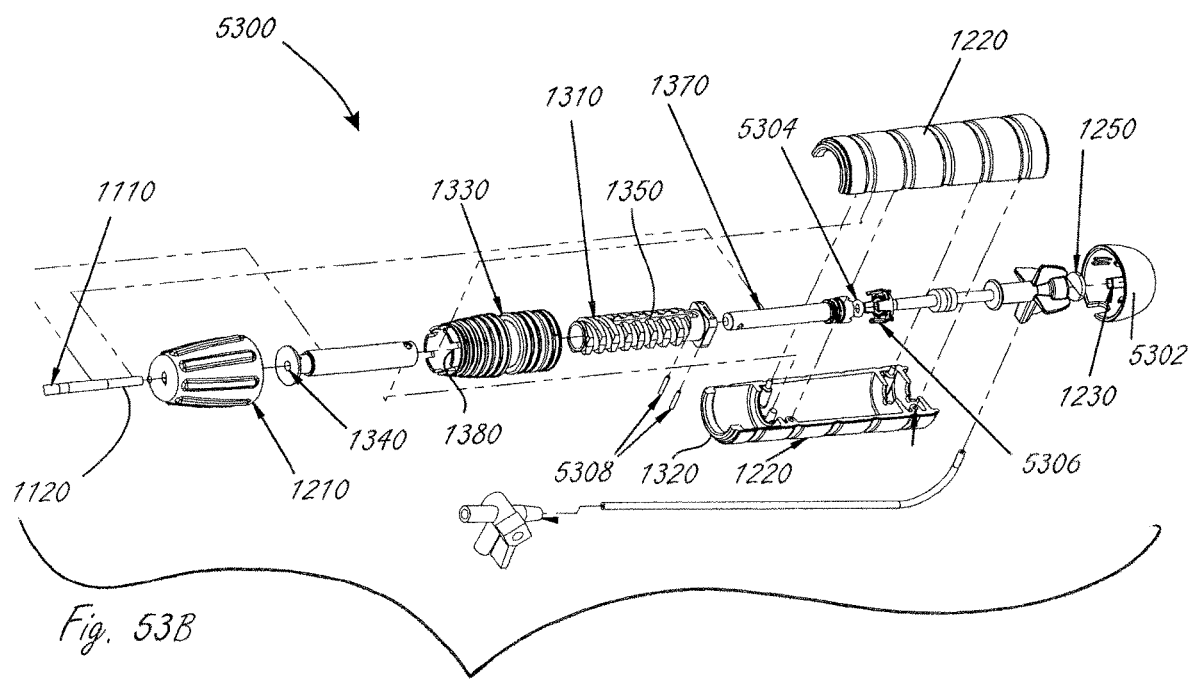
FIG. 53B is an exploded view of the exemplary external controller shown in FIG. 53A.

FIG. 53A is perspective view of an exemplary steerable medical device, including external handle and actuator. FIG. 53B is an exploded view of Detail A shown in FIG. 53A.

FIG. 53A shows, an exemplary external controller, in the form of a handle, that is adapted to deploy and actuate the steerable devices described herein. The external controller 5300 is adapted, or can be adapted to control other steerable devices not specifically described herein. In an embodiment, the external controller 5300 controls steering of an exemplary steerable sheath system 1000 that includes steerable tubular members, such as those described above. Steerable sheath system 1000 may be actuated by handle portion 1200.

Referring to FIG. 53B, an exploded view of handle portion 1200 is shown in accordance with an embodiment. Handle portion 1200 includes sheath flexure adjustment knob 1210, grip 1220, and guide wire port 1230. Portions of handle portion 1200 are indicated by similar numerals to those described above with respect to FIGS. 39-41 to indicate similar functionality of the components, however, the portions may include structural differences. For example, guide wire port 1230 may be integral to a valve cap 5302 that forms a proximal end of external controller 5300. Guide wire port 1230 may be internal to the controller, however. For example, guide wire port 1230 may include an embossed cylindrical portion extending between grip portions 1220 to direct a guidewire toward guide wire seal 1250 within handle portion 1200. Adjustment knob 1210, grip 1220, and guide wire port 1230 may form a housing to contain an actuation mechanism of external controller 5300 as described below.

Flexure, or steering, of the steerable sheath is facilitated by an actuation mechanism. More particularly, the actuation mechanism may be actuated by twisting control knob 1210 relative to handle grip 1220. Rotation of knob 1210 may in turn load portions that are respectively attached to outer shaft 1110 and inner shaft 1120 to cause relative movement between the tubular members. The method of steering the steerable medical devices herein using external controller 5300 may be similar to the methods described above with respect to FIGS. 39-41, and any suitable construction of the external controller from FIGS. 39-41, or methods of using it, may be part of external controller 5300, and its method of use.

In an embodiment, the amount of flexure of the sheath is related to the amount of rotation of adjustment knob 1210. In some embodiments there will be a relatively linear correspondence between the degrees of rotation of control knob 1210 and the angle of flexure for the sheath steerable section. In such an embodiment each unit of incremental rotation of the control knob 1210 substantially equals or "maps" into a corresponding and constant unit of incremental flexure for the sheath steerable portion, independent of the starting flexure of the steerable sheath. In alternate embodiments there can be a nonlinear correspondence. For example, in an exemplary configuration when the steerable section is at minimal flexure, control knob 1210 can impart twice as much flexure as when it is at about 50% of its allowable flexure.

A portion of external controller 5300 coupled to outer sheath 1110 may include an outer sheath interface tube 1340. Outer sheath 1110 may be anchored to the outer sheath interface tube at 1340, e.g., via adhesives, ultrasonic welding, heat staking, or other suitable ways. Outer sheath 1110 and outer sheath interface tube 1340 are, in this embodiment, axially fixed relative to grip 1220.

A portion of external controller 5300 connected to inner sheath 1120 may include an inner sheath interface tube 1370. Inner sheath 1120 may be anchored to inner sheath interface tube 1370 via any of the mechanisms described for the outer sheath. For example, the inner sheath interface tube 1370 may be adhesively bonded to inner sheath 1120 at a location proximal to a bond between outer sheath interface tube 1340 and outer shaft 1110. The inner sheath interface tube 1370 is secured to drive screw 1310. O-ring cap 5306 is secured to the proximal end of inner sheath interface tube 1370 by any suitable coupling mechanism, and with O-ring 5304 disposed therebetween. Pins 5308 are positioned inside drive screw 1310 and secure O-ring cap 5306, and thus inner sheath interface tube 1370, to drive screw 1310. The drive screw 1310, inner sheath interface tube 1370, and inner sheath 1120 therefore move axially together. Furthermore, drive screw 1310 is axially movable relative to handle grip 1220. Accordingly, in an embodiment, relative movement between outer shaft 1110 and inner shaft 1120 is effected through the movement of inner shaft 1120 relative to the handle, although handle can be modified to work in different ways to cause steering.

It will now be apparent that relative movement between shafts to effect steering may depend on relative movement between the respective portions of external controller 5300 that connect to outer shaft 1110 and inner shaft 1120. That is, relative movement between the shafts may be effected by relative linear motion between inner sheath interface tube 1370 and outer sheath interface tube 1340. In an embodiment, such relative linear motion is caused by rotation of knob actuator 1210, which causes rotation of drive nut 1330, which causes linear motion of drive screw 1310. More particularly, drive nut 1330 may engage knob 1210 such that rotation of knob 1210 produces rotation of drive nut 1330. In an embodiment, the rotation of knob 1210 and drive nut 1330 is in a 1:1 relationship, i.e., knob 1210 is fixed to drive nut 1330. Thus, control knob 1210 may sit over drive nut 1330 and may be constrained against rotation relative to the drive nut 1330. Control knob 1210 and drive nut 1330 may in turn be positioned concentrically around drive screw 1310 and inner sheath interface tube 1370, and outer sheath interface tube 1340 may sit concentrically within the drive nut 1330.

In an embodiment, drive nut 1330 may be placed in a threaded engagement with drive screw 1310. That is, an internal thread of drive nut 1330 may mesh with an external thread of drive screw 1310. Since inner sheath interface tube 1370 is axially movable relative to handle 1220, rotation of knob 1210 produces linear motion of drive nut 1330 and inner sheath interface tube 1370, and thus the inner sheath. Handle extensions 1320 (e.g., pins) ride in the drive screw slot 1350, as described above, and prevent the drive screw from rotation when the knob 1210 is rotated. The handle extensions thus cause the axial movement of drive screw 1310, which causes axial movement of the inner sheath. Axial movement of outer sheath interface tube 1340 is prevented, relative to handle grip 1220, by handle extensions 1320 (e.g., pins), which extends into an aperture in the proximal end of outer sheath interface tube 1340. The position of outer sheath interface tube 1340 and thus the outer sheath are axially fixed relative to handle grip 1220. Actuation of actuator 1210 thus, in this embodiment, axially moves the inner sheath but does not cause axial movement of the outer sheath. In some embodiments the external controller is adapted such that, upon actuation, the outer tubular member moves axially but the inner tubular member does not.

FIGS. 54A-54C illustrate an exemplary outer tubular member 620 of a steerable medical device. Outer tubular member 620 can be built into any of the steerable medical devices herein, and can be used with any of the inner tubular members herein, or any of the handle assemblies herein. In some embodiments a steerable medical device includes outer tubular member 620 and inner tubular member 550 shown in FIGS. 50A-50E. In some regards outer tubular member 620 is similar to the outer tubular member shown and described with respect to 48A-48D herein, but there are differences between the two exemplary embodiments.

Outer tubular member 620 includes a steerable portion 622, which includes first segment 623 and second segment 624. First segment 623 has a higher durometer than second segment 624. First segment 623 acts as a spine along steerable portion 624. In some embodiments first segment 623 has a durometer between 45D and 90D, such as between 55D and 85D, such as between 65D and 80D (e.g., 72D Pebax), and second segment 624 has a durometer between 20D and 50D, such as between 25D and 45D (e.g., 35D Pebax). First segment 623 extends less than 180 degrees around the outer tubular member, and second segment 624 extends more than 180 degrees around the outer tubular member. The joints between the two segments are parallel to the longitudinal axis of the outer tubular member. In other embodiments, however, the joints between segments 623 and 624 can be non-parallel to the longitudinal axis of the outer tubular member, and may also be non-perpendicular to the longitudinal axis of the outer tubular member. For example, any portion of the joint (or seam) between segments 623 and 624 can be angled as described above with respect to inner tubular member 550. Outer tubular member 620 includes a transitional proximal portion 625, which may have a durometer between about 50D and 90D, such as between 60D and 80D (e.g., 72D Pebax). Outer tubular member 620 also includes relatively longer proximal portion 626, which may extend all the way to a handle assembly, such as any of the handle assemblies described herein. More particularly, proximal portion 626 may extend to a proximal end of outer tubular member 620. In a merely exemplary embodiment proximal portion 626 is a polyamide, e.g., Vestamid, material.

FIG. 54B illustrates a view taken through Section H-H shown in FIG. 54A.

FIG. 54C shows detail F shown in FIG. 54A, which is a distal region of outer tubular member 620. Distal to steerable portion 622 is a section 627, which may be shorter than steerable portion 622, and distal to section 627 is distal tip 628. FIG. 54C also shows that outer tubular member 620 also includes optional reinforcing member 631 (in this embodiment a Kevlar strip) and second reinforcing member 632 (in this embodiment a braided material). The reinforcing strip may have a cross-sectional geometry having uniform cross-sectional dimensions or non-uniform cross-sectional dimensions. For example, the cross-sectional geometry may be circular, such that the cross-sectional dimension is a uniform diameter. Alternatively, the cross-sectional geometry may be rectangular or elliptical, such that the cross-sectional dimensions include a width greater than a height, or vice versa. Accordingly, the cross-sectional geometry may result in higher reinforcement in one direction, e.g., in the direction of a horizontal axis of the strip, than in another direction, e.g., in the direction of a vertical axis of the strip. Reinforcing member 631 is disposed within the spine of outer tubular member 620, and specifically within first segment 623. Reinforcing member 631 extends axially (parallel to a longitudinal axis of outer tubular member 620) and through a midpoint of first segment 623. Alternatively stated, a plane containing reinforcing member 631 and a central axis of outer tubular member 620 may divide first segment 623 into two hypothetical symmetrical sections. In some embodiments reinforcing member 631 is a Kevlar line.

Reinforcing member 631 can help prevent unwanted stretching of the outer tubular member spine (e.g., segment 623) if it is placed under tension during bending. For example, if outer tubular member 620 is placed under tension via a handle assembly to steer the steerable section, first segment 623 may stretch more than desired, resulting in an increase in the travel of the outer tubular member in the handle to steer the steerable section. The unwanted stretching can thus lead to inefficient steering by increasing the travel needed to steer the steerable portion to the desired configuration. Reinforcing member 631 in the spine of outer tubular member can reduce the stretching, and thus the travel, and thus can increase the efficiency of the bending. In some embodiments the steerable system may be adapted to put outer tubular member 623 only in compression, and it may not be necessary to include reinforcing member 631. Alternatively, even in systems where the inner tubular member is put under tension, it may not be necessary to include reinforcing member 631.

Reinforcing member 631 can be woven through second reinforcing member 632 (e.g., a braided material) in any desired pattern. Either of the ends of reinforcing member 631 can be everted such as described above. More particularly, either end of the reinforcing member 631 may be folded on itself, however, in this embodiment neither end is everted.

The ends of reinforcing member 631 can be disposed over or under second reinforcing member 632 along at least one wire. For example, in an embodiment, a distal end of reinforcing member 631 is woven between the braided material and coincides with a distal end of the braiding material. Furthermore, the reinforcing member 631 may extend to a distal end of the outer tubular member 620. More particularly, the distal end of the reinforcing member 631 may be located within a bonding region where the distal end of the outer tubular member 620 is bonded to the inner tubular member 550. Locating the distal end of the reinforcing member 631 within this bonding region may minimize stretching of the outer tubular member 620 in some actuation modes, and thus, may reduce the range of travel of the controller 650 required to achieve a particular steering bend.

A proximal end of reinforcing member 631 may overlap the wires of the braided material. More particularly, the proximal end portion transitions from a triaxial braid configuration to overlap either an outside surface or an inside surface of the wires. This is similar to the manner of overlap described above with respect to an embodiment of inner tubular member 550 above. More particularly, an end section of the reinforcing member 631 may overlay or underlay at least one turn of each braid wire.

The distal end of reinforcing member 631 extends into distal tip section 628 of outer tubular member 620, and can extend all the way to the end of the distal tip section 628. In some embodiments the distal end of reinforcing member 631 is in section 627. The proximal end of reinforcing member 631 is disposed proximal to steerable portion 622, and in this embodiment is disposed in transition section 625.

In this embodiment liner 633 does not extend to the distal end of outer tubular member 620. Specifically, liner 633 extends to the distal end of section 627, but not into tip section 628.

Distal tip section 628, from inside to outside, includes inner layer 630, a layer that includes both reinforcing members 631 and 632 (631 woven in 632 along at least a portion of tip section 628), marker band 629, and outer layer 635. In some embodiments inner layer 630 can have a durometer from 20D to 50D, such as 30D to 40D (e.g., 35D). In some embodiments outer layer 635 has a durometer from 40D to 70D, such as 45D to 65D (e.g., 55D).

In some embodiments the inner and outer tubular members have linear reinforcing members (e.g., Kevlar lines), and are 180 degrees apart. The reinforcing members can be aligned with spines of both inner and outer tubular members.

FIG. 55A illustrates a portion of an exemplary steerable medical device 645, including inner tubular member 550, outer tubular member 620, and flexible distal tip 640. FIG. 55B shows section W-W shown in FIG. 55A. FIG. 55C shows section Z-Z shown in FIG. 55B, and FIG. 55D shows detail A-A of the distal end shown in FIG. 55C. As shown in FIG. 55B, the reinforcing members 631 and 557 are 180 degrees from each other. Reinforcing member 557 of the inner tubular member is 180 degrees from the midpoint of the higher durometer segment, 623, in outer tubular member 620. FIG. 55C illustrates distal tip 640 secured to outer tubular member 620 and inner tubular member 550, which are also secured to one another. FIG. 55D highlights the bonded nature of inner tubular member 550 and outer tubular member 620, and flexible distal tip 640. Inner tubular member 550 extends further distally than outer tubular member 620, and both are secured to distal flexible tip 640. More particularly, inner tubular member 550, outer tubular member 620, and distal flexible tip 640 may be fused together using, e.g., a heat fusing process, to form steerable medical device 645.

A distal end of reinforcing member 631 may coincide with a distal end of outer tubular member 620. For example, the distal end of reinforcing member 631 can have a same axial location or extent as a distal end of outer tubular member 620. In an embodiment, the distal end of reinforcing member 631 is within the bond region formed by fusing the inner tubular member 550, the outer tubular member 620, and the distal flexible tip 640.

FIGS. 56A-H illustrate an exemplary external controller 650 that is adapted to steer a steerable medical device, optionally any of the steerable devices herein that include first and second tubular members, such as steerable medical device 645 that includes outer tubular member 620 and inner tubular member 550. The steerable medical device can include any of the inner and outer tubular members herein, including any combination thereof.

Figure 56A:
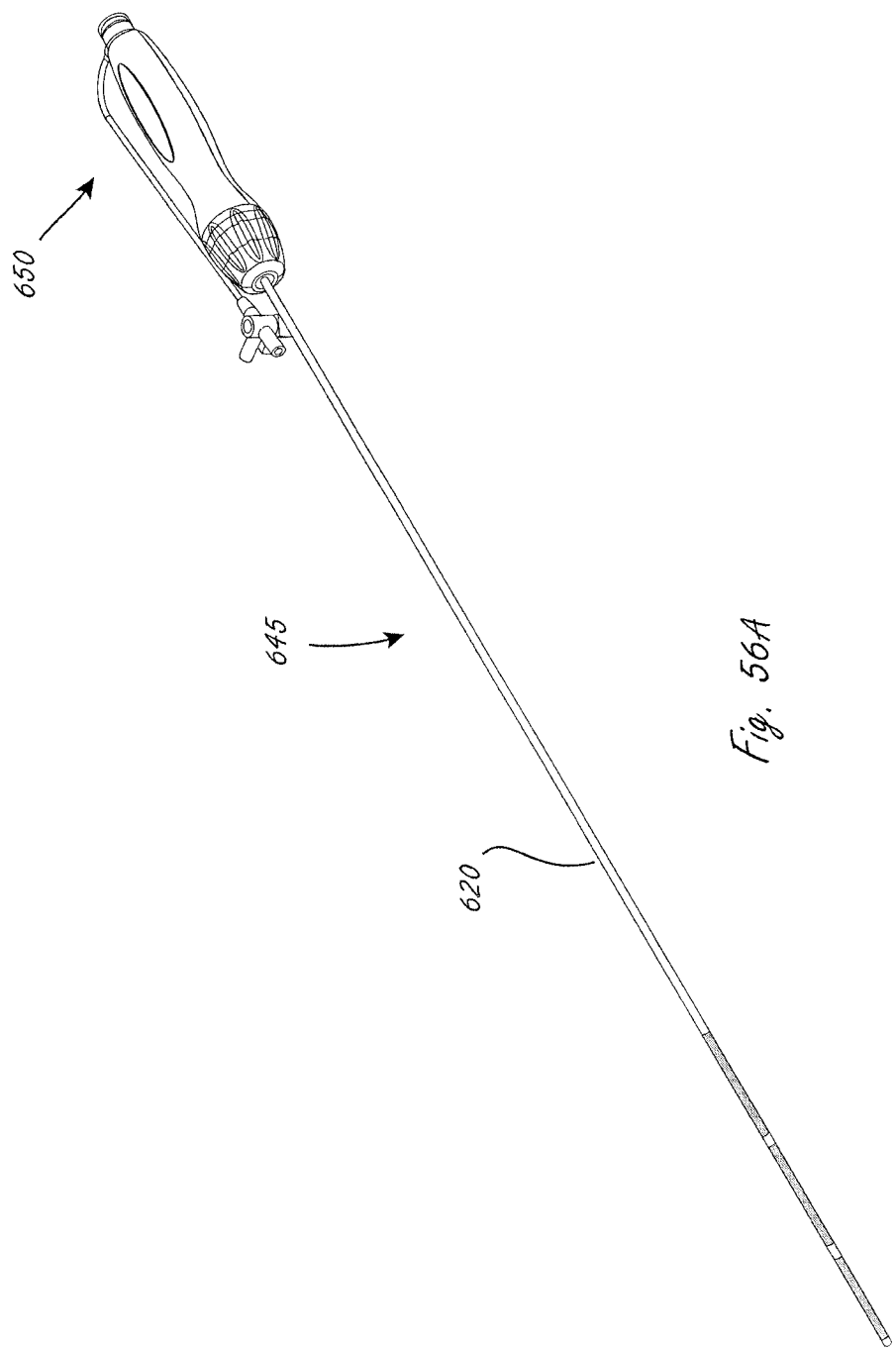
Figure 56B:
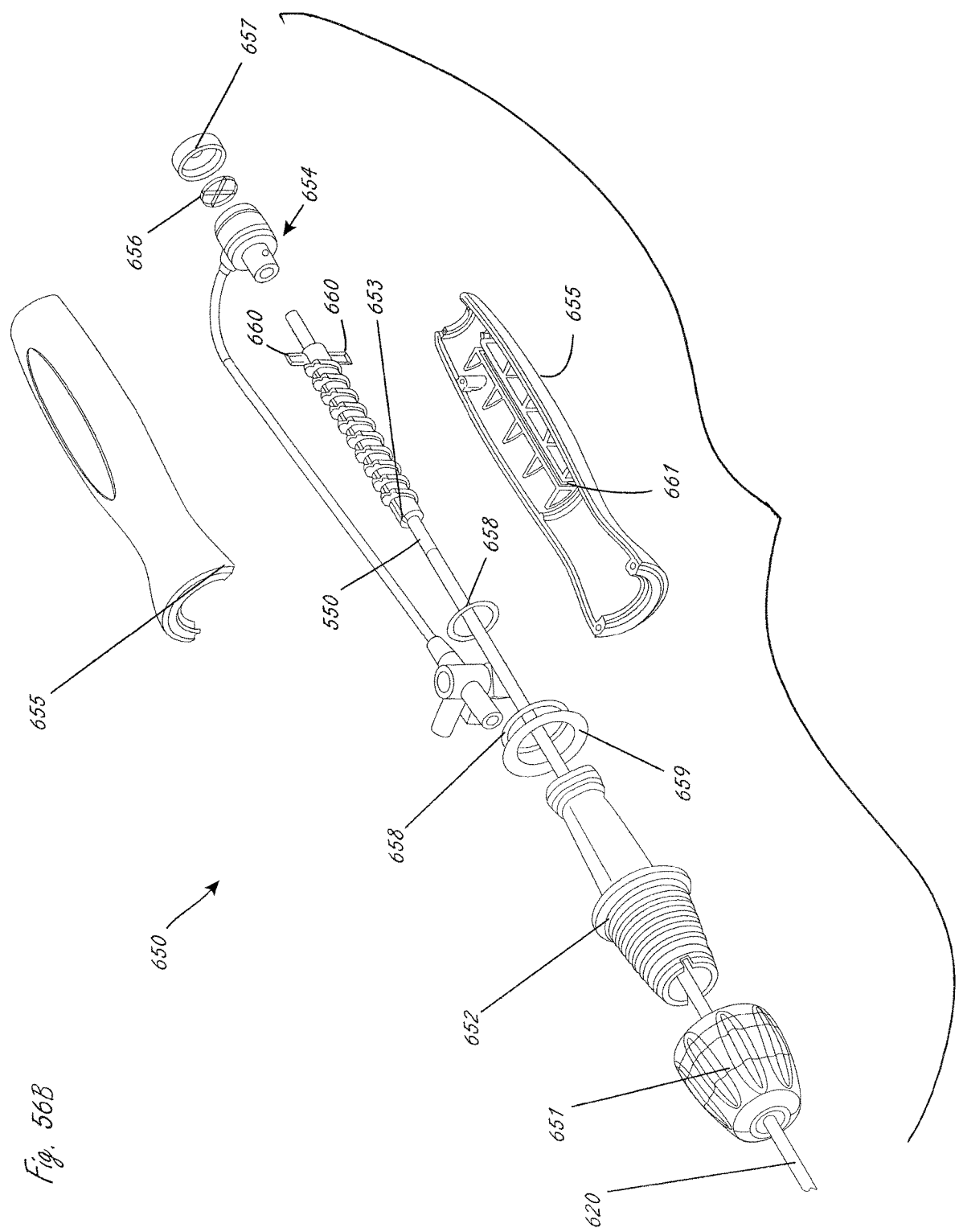

FIG. 56A is a perspective view showing the assembled assembly, including external controller 650 secured to steerable device 645. FIG. 56B shows an exploded view of external controller, which includes an actuator grip 651 (e.g., rotatable knob), actuator nut 652, drive screw 653 including two wings 660 extending radially from the screw, valve body 654 (and optionally a stopcock tethered to the valve body 654 and placed in fluid communication with the valve body 654 by a tubular flush line), handle shells or grips 655 each including a slot 661, valve 656, valve cap 657, friction members 658, and bearing 659. Also shown are outer tubular member 620 and inner tubular member 550.

Figure 56H:
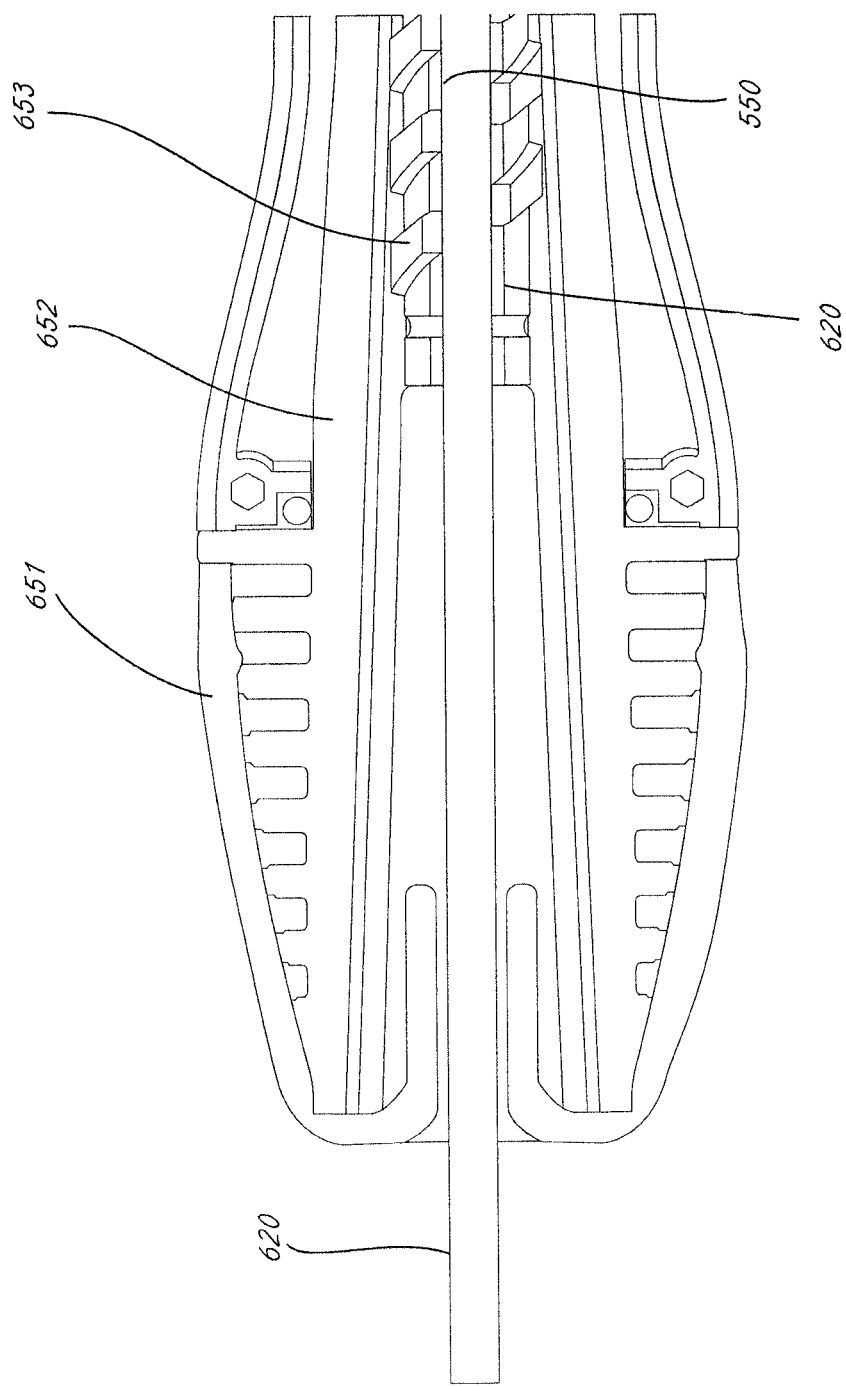

FIG. 56C shows an assembled view of controller but with one handle shell removed, and compared to FIG. 56B would be considered a bottom view with bottom handle shell 655 removed. FIG. 56D shows a sectional view 90 degrees relative to the view in 56C. FIG. 56E is a sectional view of the view from 56C. FIGS. 56F-H show highlighted views of portions of the controller from the sectional view from FIG. 56E. FIG. 56F shows a central region, FIG. 56G shows a proximal region, and FIG. 56H shows a distal region of external controller.

In this embodiment the proximal end of inner tubular member 550 is secured directly to valve body inside a channel in valve body 654. Outer tubular member 620 is secured within a distal region of drive screw 653. Distal movement of drive screw 653 pushes on outer tubular member and puts it in compression, and because the tubular members are axially fixed distal to the steerable portion, inner tubular member is put under tension. Proximal movement of drive screw 653 pulls on outer tubular member 620, putting it in tension, which puts the inner tubular member in compression. Distal movement of drive screw 653 causes the steerable device 645 to steer in a first direction, while proximal movement of drive screw 653 causes the steerable device 645 to bend in a second direction. In embodiments in which the tubular members have spines that are 180 degrees apart (such as with tubular members 550 and 620), the two bending directions are in the same plane, 180 degrees apart. Inner tubular member 550 is disposed within drive screw 653 and drive screw 653 can move axially relative to inner tubular member 550.

In an embodiment, drive screw 653 extends proximally from outer tubular member 620 and surrounds at least a portion of inner tubular member 550 between a proximal end of outer tubular member 620 and valve body 654. As such, drive screw 653 provides column support to inner tubular member 550 by limiting transverse deflection of inner tubular member 550. More particularly, when inner tubular member 550 is placed in compression, it may have a tendency to buckle, however, drive screw 653 around inner tubular member 550 may prevent such buckling. Thus, drive screw 653 may serve dual functions as both a force transmission element to convert rotational motion of the actuator nut 652 into axial motion of outer tubular member 620, and an anti-buckling element to prevent buckling of inner tubular member 550 during steering.

In this embodiment axial movement of drive screw 653 is caused by actuation of actuator grip 651, and in this embodiment, rotation of actuator grip 651. Actuator grip 651 is secured to nut 652, such that rotation of actuator grip 651 causes nut 652 to rotate as well. Actuator grip 651 is a gripping element that facilitates the rotation of nut 652. Nut 652 has an internal interfacing element that interfaces with the outer thread of drive screw 653. In an embodiment, the internal interfacing element of nut 652 is a single thread, i.e., a thread having a single turn, to engage the thread of drive screw 653. Thus, the length of threaded contact between nut 652 and drive screw 653 is fewer than ten turns, e.g., fewer than five turns, in an embodiment. In an embodiment, the threaded interface occurs at a central region 670 of drive screw 653. Additionally, drive screw 653 includes two wings 660 (or pins) that are 180 degrees part, each of which extends radially from the body of the screw and rides in a separate slot 661 of handle grips 655. The interface between the wings and the slots prevents the drive screw 653 from rotating when actuator grip 651 is rotated. When actuator grip 651 is rotated, the internal interfacing element of nut 652 rotates relative to the thread of drive screw 653, the interface between wings 660 and slots 661 prevents the drive screw from rotating, and the drive screw 653 will move axially, either proximally or distally, depending on the direction of rotation of actuator grip 651. The ability to bend the steerable device 645 in two directions is referred to generally herein as bi-directional steerability, which external controller 650 provides.

The interfacing location 670 between the nut 652 and drive screw 653 is relevant to the bi-directional steerability. Because the interface is in a central region of the thread (i.e., not at an extreme end of the thread of the drive screw), rotation of actuator grip 651 in both directions causes axial movement of drive screw 653 (either distally or axially depending on the direction or rotation). This puts the outer tubular member in either compression or tension (depending on the direction of rotation), which puts the inner tubular member in the other of compression and tension, and under either scenario the steerable device is steered, but not necessarily in the same direction, e.g., in opposite directions.

By allowing the drive screw to move in both directions (such as by interfacing the thread at a central region), bi-directionality can be achieved. Interfacing the thread at the extreme distal or proximal end may allow the drive screw to travel in only one direction, and would thus remove the bi-directionality of the device. As long as the interface is at a location that allows for some axial movement in both directions (even if just very little axial movement in one direction), bi-directionality can be achieved. By changing the location 670 of the interface between drive screw 653 and nut 652 (away from exact center of thread of the drive screw), a bias can be put in the steerable device, such that it can be steered more in one direction than the other. For example, if range of travel of drive screw 653 is greater in a certain axial direction, i.e., either distally or proximally, a range of steering may be greater in a corresponding direction, e.g., steerable device 645 may curve more in one direction than another. If there is a bias, however, bi-directionality would still be achieved.

In an embodiment, a direction of steering may be aligned with the flush line extending from the valve body 654. Steering may be within a plane containing a central axis of the steerable device 645. That is, deflection of steerable device 645 may result in steering within the plane to one side or another of the central axis. Since such steering ordinarily occurs while the steerable device 645 is located in a patient anatomy, however, it may difficult for a physician to ascertain the orientation of the steerable device 645 relative to the controller 650 outside of the patient anatomy. To compensate for this, the flush line may extend laterally from a side wall of the valve body 654 in a direction within the plane of steering. Thus, the physician may determine a relative orientation between the flush line outside of the anatomy and the distal end of steerable device 645 inside the anatomy to predict a direction of steering inside the anatomy.

In some embodiments the actuator grip 651 and nut 652 could be integral, such that they can be considered the same part (e.g., together an "actuator"). For example, actuator grip 651 may be a rubber component overmolded on the nut 652 to form an integrated, two-part body.

Controller 650 also includes valve 656, which is held in place when valve cap 657 is secured to valve body 654. More particularly, valve 656 may be compressed between valve cap 657 and valve body 654. Valve 656 may, for example, include a slit diaphragm, and thus, such compression may maintain an integrity of the slit diaphragm to prevent leaking. For example, the compressed diaphragm may prevent blood from leaking through valve 656, and thus, valve 656 may maintain hemostasis of the controller 650. Nonetheless, the slit diaphragm of valve 656 may permit passage of a working device, e.g., a guidewire, through valve 656, controller 650, and steerable device 645. Actuator grip 651 and nut 652 can be secured together using any number of known techniques. Actuator grip 651 can be a soft material such as rubber that slides over nut 652, with internal features on the inside of actuator grip 651 that interface with external features of nut 652 (see FIG. 56H). When actuator grip 651 and nut 652 are not integral (such as in this embodiment), torque may be transmitted from actuator grip 651 to nut 652. Distal end of nut 652 has a plurality of female components (see FIG. 56B) that interface with male components on the inside of actuator grip 651, and the interface transmits torque. For example, the male components may include radial fins extending laterally from an inner surface of actuator grip 651, and the fins may engage corresponding slots formed through an outer wall of nut 652. Accordingly, the keyed relationship between the fins and the slots may allow for rotation of actuator grip 651 to transmit a rotational force from the fins to the slots to cause a corresponding rotation of nut 652.

Bearing 659 may include a flattened ring, such as a washer profile, to prevent contact between nut 652 and shells 655. Accordingly, bearing 659 may reduce friction between nut 652 and handle shells 655. This provides for ease of rotation of actuator grip 651 and smooth actuation of steerable device 645.

Friction members 658 may be o-rings that act as frictional elements to provide smooth friction, and are disposed in slots in the handle shells. More particularly, the friction members 658 may include an outer surface to slide against handle shells 655 and an inner surface to slide against nut 652 to provide an increased and repeatable surface contact and frictional force between those elements. Accordingly, friction members 658 can reduce or prevent backlash.

In some embodiments the proximal end of outer tubular member is disposed inside the drive screw less than 2 inches from the distal end of the drive screw, and can be secured in place relative to the drive screw with glue injected into a glue port or a glue hole in the drive screw. In some embodiment the proximal end of the inner tubular member 550 extends 1 mm to 200 mm further proximally that the proximal end of the outer tubular member 620.

What is claimed is:

1. A steerable medical device, comprising:
    an inner flexible tubular member with a polymeric inner spine of a first material extending along a length of a steerable portion and having a durometer greater than a second segment material extending along the length of the steerable portion;
    an outer flexible tubular member axially fixed to the inner flexible tubular member at a fixation location distal to the steerable portion, the outer tubular member having a polymeric outer spine that is offset from the inner spine having a linear segment of a first material extending less than 180 degrees around the outer tubular member and having a durometer greater than a second segment material extending more than 180 degrees around the outer tubular member,
    a linear reinforcing member extending within at least one of the first material of a greater durometer of said polymeric inner spine or the first material of a greater durometer of said polymeric outer spine; and
    an external controller operatively interfacing with the inner and outer flexible tubular members to put one of the inner and outer tubular members in tension and the other in compression, to steer the steerable portion.

2. The steerable medical device of claim 1 wherein the linear reinforcing member is respectively extending within both the polymeric inner spine and the polymeric outer spine.

3. The steerable medical device of claim 1 wherein linear reinforcing member is 180 degrees away from the polymeric inner spine around the steerable medical device.

4. The steerable medical device of claim 1 wherein the outer tubular member further comprises a braided reinforcing member in the steerable portion.

5. The steerable medical device of claim 1 wherein a distal end of the linear reinforcing member is further distally than a distal end of the steerable portion.

6. The steerable medical device of claim 1 wherein a distal end of the linear reinforcing member extends to a location where the inner tubular member and outer tubular member are axially secure together.

7. The steerable medical device of claim 2 wherein the linear reinforcing member of the polymeric outer spine and the linear reinforcing member of the polymeric inner spine are 180 degrees away from each other around the steerable medical device.

8. The steerable medical device of claim 4 wherein the linear reinforcing member is woven into the braided reinforcing member.

9. The steerable medical device of claim 5 wherein a distal end of the linear reinforcing member extends substantially to a distal end of the outer tubular member.

* * * * *